(12) United States Patent
Roecker et al.

(10) Patent No.: US 10,442,778 B2
(45) Date of Patent: Oct. 15, 2019

(54) N1-PHENYLPROPANE-1,2-DIAMINE COMPOUNDS WITH SELECTIVE ACTIVITY IN VOLTAGE-GATED SODIUM CHANNELS

(71) Applicant: Merck Sharp & Dohme Corp., Kenilworth, NJ (US)

(72) Inventors: Anthony J. Roecker, Harleysville, PA (US); Mark E. Layton, Harleysville, PA (US); Thomas J. Greshock, Collegeville, PA (US); Joseph E. Pero, Harleysville, PA (US); Michael J. Kelly, III, Paoli, PA (US); Ting Zhang, Princeton Junction, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/086,654

(22) PCT Filed: Mar. 17, 2017

(86) PCT No.: PCT/US2017/022863
§ 371 (c)(1),
(2) Date: Sep. 20, 2018

(87) PCT Pub. No.: WO2017/165204
PCT Pub. Date: Sep. 28, 2017

(65) Prior Publication Data
US 2019/0092738 A1 Mar. 28, 2019

Related U.S. Application Data

(60) Provisional application No. 62/311,650, filed on Mar. 22, 2016.

(51) Int. Cl.
| | | |
|---|---|---|
| *C07D 277/52* | (2006.01) |
| *C07D 285/08* | (2006.01) |
| *A61K 31/635* | (2006.01) |
| *A61K 45/06* | (2006.01) |
| *A61K 31/18* | (2006.01) |
| *A61K 31/427* | (2006.01) |
| *A61K 31/426* | (2006.01) |
| *A61K 31/433* | (2006.01) |
| *C07F 7/08* | (2006.01) |

(52) U.S. Cl.
CPC ............ *C07D 277/52* (2013.01); *A61K 31/18* (2013.01); *A61K 31/426* (2013.01); *A61K 31/427* (2013.01); *A61K 31/433* (2013.01); *A61K 31/635* (2013.01); *A61K 45/06* (2013.01); *C07D 285/08* (2013.01); *C07F 7/0812* (2013.01)

(58) Field of Classification Search
None
See application file for complete search history.

(56) References Cited

U.S. PATENT DOCUMENTS

| | | |
|---|---|---|
| 2002/0143033 A1 | 10/2002 | Gregory et al. |
| 2010/0004300 A1 | 1/2010 | Zimmermann et al. |

FOREIGN PATENT DOCUMENTS

| | | |
|---|---|---|
| WO | 2010079443 A1 | 7/2010 |
| WO | 2015077905 A1 | 6/2015 |
| WO | 2015080988 A1 | 6/2015 |
| WO | 2017/106409 A1 | 6/2017 |

OTHER PUBLICATIONS

International Search Report and Written Opinion for PCT/US2017/022863 dated Jun. 9, 2017; 9 pages.
European Search Report for Application No. 17770855.9-1116/3484464 dated Aug. 1, 2019, 7 pages.

*Primary Examiner* — Kamal A Saeed
(74) *Attorney, Agent, or Firm* — Patricia A. Shatynski; John C. Todaro

(57) ABSTRACT

Disclosed are compounds of Formula A-1, or a salt thereof: Formula A-1, where J, K, Q and R1 are as defined herein, which compounds have properties for inhibiting sodium ion channels found in peripheral and sympathetic neurons. Also described are pharmaceutical formulations comprising the compounds of Formula A-1 or their salts, and methods of treating pain (e.g. chronic pain), or cough or itch disorders using the same.

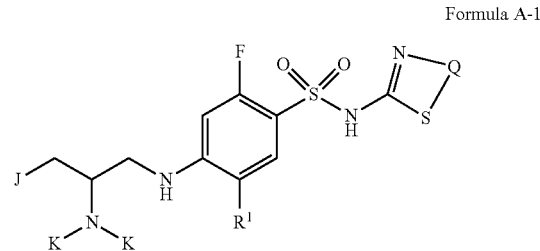

Formula A-1

18 Claims, No Drawings

N1-PHENYLPROPANE-1,2-DIAMINE COMPOUNDS WITH SELECTIVE ACTIVITY IN VOLTAGE-GATED SODIUM CHANNELS

CROSS-REFERENCE TO RELATED APPLICATIONS

This application is a U.S. National Phase application under 35 U.S.C. § 371 of PCT Application No. PCT/US2017/022863. Filed Mar. 17, 2017, which claims the priority of U.S. Provisional Application Ser. No. 62/311,650 filed Mar. 22, 2016, which application is incorporated herein by reference.

BACKGROUND

Voltage-gated sodium channels play a central role in initiating and propagating action potentials in electrically excitable cells such as neurons and muscle, see for example Yu and Catterall, Genome Biology 4:207 (2003) and references therein. Voltage-gated sodium channels are multimeric complexes characterized by an Alpha-subunit which encompasses an ion-conducting aqueous pore, and is the site of the essential features of the channel, and at least one Beta-subunit that modifies the kinetics and voltage-dependence of the channel gating. These structures are ubiquitous in the central and peripheral nervous system where they play a central role in the initiation and propagation of action potentials, and also in skeletal and cardiac muscle where the action potential triggers cellular contraction. (see Goldin, Ann NY Acad Sci. 30; 868:38-50 (1999)).

Sensory neurons are also responsible for conveying information from the periphery e.g. skin, muscle and joints to the central nervous system (spinal cord). Sodium channels are integral to this process as sodium channel activity is required for initiation and propogation of action potentials triggered by noxious stimuli (thermal, mechanical and chemical) activating peripheral nociceptors.

Nine different Alpha-subunits have been identified and characterized in mammalian voltage-gated sodium channels. These structures are designated $Na_v$ 1.X sodium channels (X=1 to 9) in accordance with currently accepted nomenclature practice, designating their ion selectivity (Na), the physiological regulator ('v', potential, i.e. voltage), and the gene subfamily encoding them (1), with the number designator X (1 to 9) being assigned for the alpha subunit present in the structure (see Aoldin et al., Neuron, 28:365-368 (2000)). $Na_v$1.7 voltage-gated sodium ion channels (herein designated "Nav 1.7 channels" in some instances for convenience) are expressed primarily in sensory and sympathetic neurons, are believed to play a role in various maladies, for example, nociception, cough, and itch, and in particular have a central role in inflammatory pain perception, (see Wood et al. J. Neurobiol. 61: pp 55-71 (2004), Nassar et al., *Proc. Nat. Acad. Sci.* 101(34): pp 12706-12711 (2004), Klinger et. al., Molecular Pain, 8:69 (2012), see Devigili et. al., Pain, 155(9); pp 1702-7 (2014), Lee et. al., Cell, 157:1-12 (2014), Muroi et. al., Lung, 192:15-20 (2014), Muroi et. al., Am J Physiol Regul Integr Comp Physiol 304:R1017-R1023 (2013)).

Loss of function mutations in $Na_v$ 1.7 lead to Cogenital Insensitivity to Pain (CIP), where patients exhibit a lack of pain sensation for a variety of noxious stimuli (Goldberg et al., Clinical Genetics, 71(4): 311-319 (2007)). Gain of function mutations in $Na_v$ 1.7, $Na_v$1.8, and $Na_v$ 1.9 manifest in a variety of pain syndromes where patients experience pain without an external stimulus (Fischer and Waxman, Annals of the New York Academy of Sciences, 1184:196-207 (2010), Faber et al., PNAS 109(47): 19444-19449) (2012), Zhang et al., American Journal of Human Genetics, 93(5):957-966 (2013)).

Accordingly, it is believed that identification and administration of agents which interact to block $Na_v$ 1.7 voltage-gated sodium ion channels represents a rational approach which may provide treatment or therapy for disorders involving $Na_v$1.7 receptors, for example, but not limited to, acute pain, preoperative pain, perioperative pain, post-operative pain, neuropathic pain, cough, or itch disorders, as well as those stemming specifically from dysfunction of $Na_v$1.7 voltage-gated sodium ion channels, see Clare et al., Drug Discovery Today, 5: pp 506-520 (2000)).

It has been shown in human patients as well as in animal models of neuropathic pain that damage to primary afferent sensory neurons can lead to neuroma formation and spontaneous activity, as well as evoked activity in response to normally innocuous stimuli. [Carter, G. T. and Galer, B. S., Advances in the Management of Neuropathic Pain, Physical Medicine and Rehabilitation Clinics of North America, 2001, 12(2): pp 447 to 459]. Injuries of the peripheral nervous system often result in neuropathic pain persisting long after an initial injury resolves. Examples of neuropathic pain include, for example, post herpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias. The ectopic activity of normally silent sensory neurons is thought to contribute to the generation and maintenance of neuropathic pain, which is generally assumed to be associated with an increase in sodium channel activity in the injured nerve. [Baker, M. D. and Wood, J. N., Involvement of Na Channels in Pain Pathways, TRENDS is Pharmacological Sciences, 2001, 22(1): pp 27 to 31].

Nociception is essential for survival and often serves a protective function. However, the pain associated with surgical procedures and current therapies to relieve that pain, can delay recovery after surgery and increase the length of hospital stays. As many as 80% of surgical patients experience post-operative pain, which arises as a result of tissue damage, including damage to peripheral nerves and subsequent inflammation). Furthermore, 10-50% of surgical patients will develop chronic pain after surgery often because the nerve damage results in lasting neuropathic pain once the wound has healed (Meissner et al., Current Medical Research and Opinion, 31(11):2131-2143 (2015)).

Cough is one of the most prevalent symptoms for which patients seek the attention of their primary care physicians; chronic cough for example is estimated to affect approximately 40% of the population. The fundamental mechanisms of the cough reflex are complex and involve an array of events initiated by the activation of airway sensory nerves that physically results in a forced expiration of the airways. This protective reflex is necessary to remove foreign material and secretions from the airways, however, chronic, non-protective cough results in a dramatic negative impact on quality of life (see Nasra et. al., Pharmacology & Therapeutics, 124(3):354-375 (2009)).

Cough symptoms can arise from the common cold, allergic and vasomotor rhinitis, acute and chronic bacterial sinusitis, exacerbation of chronic obstructive pulmonary disease, *Bordetella pertussis* infection, asthma, postnasal-drip syndromes, gastroesophageal reflux disease, eosinophilic and chronic bronchitis, and angiotensin-converting-enzyme inhibitors, cough is categorically described as acute, subacute, or chronic, respectively lasting less than three weeks, three to eight weeks, and more than eight weeks in duration (see Irwin et. al., The New England Journal of Medicine, 343(23):1715-1721 (2000)).

Current standard of care for the treatment of cough consists of centrally and peripherally acting suppresents such as opioids and local anaesthetics respectively, both of which are dose-limited by side-effects (see Cox et. al., Best Practice & Research Clinical Anaesthesiology, 117(1):111-136 (2003) and Benyamin et. al., Pain Physician, 11:S105-S120 (2008)). Opioids primarily act on t-opioid receptors of the central nervous system, and in some reports, also on peripheral afferents of the cough reflex arc—they exhibit varied degrees of efficacy and are limited by side-effects such as sedation, physical dependence, and gastrointestinal problems; morphine has shown to be an effective treatment for chronic cough (see Morice et. al., Am J Respir Crit Care Med 175:312-315 (2007) and Takahama et. al., Cough 3:8 (2007)), but is generally restricted to patients with terminal illness such as lung cancer. Codeine, found in some cough syrups, and also administered systemically, was found no more effective than placebo (see Smith et. al., Journal of Allergy and Clinical Immunology, 117:831-835 (2006). Local anesthetics act peripherally by reducing the generation of action potentials in sensory nerves of the airway as a result of non-selectively inhibiting all voltage gated sodium channel subtypes and have demonstrated varied degrees of efficacy in treating cough. These compounds are often found in over-the-counter lozenges and have been shown to relieve cough when administered via nebulisation (see Nasra et. al., Pharmacology & Therapeutics, 124(3):354-375 (2009) and Hansson et. al., Thorax, 49(11): 1166-1168 (1994)). However, in a study with chronic obstructive pulminary disease patients, lidocaine was not effective (see Chong et. al., Emerg Med J, 22(6):429-32 (2005)).

In pre-clinical animals, $Na_v1.7$, $Na_v1.8$, and $Na_v1.9$ were determined to be the primary voltage-gated sodium channels expressed in the afferent nerves of the respiratory tract (see Muroi et. al., Lung, 192:15-20 (2014)) and in animal models of cough, suppression of $Na_v1.7$ function resulted in a marked decrease in number of coughs (see Muroi et. al., Am J Physiol Regul integr Comp Physiol, 304:R1017-R0123 (2013)), thus, combined with previous evidence that local anesthetics can be effective antitussive agents, the targeted blockade of $Na_v1.7$ channels is believed to represent a rational approach for the treatment of cough with a preferential side-effect profile as compared to local anesthetics. Local anesthetics undesirably inhibit all voltage gated sodium channels, such as $Na_v1.5$ channels which are found in heart muscle (see Rook et. al., Cardiovascular Research 93:12-23 (2012)).

Pruritus, also commonly known as itch, affects approximately 4% of the global population (see Flaxman et. al., Lancet, 380:2163-2196 (2012)) and is "an unpleasant sensation that elicits the desire or reflex to scratch" and is regarded as closely related to pain. Theories on the origin of itch implicate the subtle, low-frequency activation of nociceptors (pain-sensing neurons), however, it has been described that some afferents preferentially respond to histamine, which induces itch (see Schmelz et. al., J Neuroscience, 17(20):8003-8008 (1997)). At the same time, it has been found that histamine-responding neurons also respond to capsaicin which produces pain (see McMahon et. al., Trends. Neurosci., 15:497-501 (1992)). Members of the transient receptor potential (TRP) family, and nerve growth factor (NGF) are both known to play a role in itch and pain, and clinically, both maladies are treated with therapeutic agents such as gabapentin and antidepressants—as such, it continues to be accepted that the underlying mechanisms of pain and itch are highly interwoven and complex, and distinguishing pan-selective or itch-selective pathways remains ambiguous (see Ikoma et. al., Nature Reviews Neuroscience, 7:535-547 (2006)).

Itch, both chronic and acute, can arise from many different insults and diseases and may be classified as dermal or pruriceptive, neurogenic, neuropathic, or psychogenic: itch can arise from both systemic disorders, skin disorders, as well as physical or chemical insult to the dermis. Pathologically, conditions such as dry skin, eczema, psoriasis, varicella zoster, urticaria, scabies, renal failure, cirrhosis, lymphoma, iron deficiency, diabetes, menopause, polycythemia, uremia, and hyperthyroidism can cause itch, as can diseases of the nervous system such as tumors, multiple sclerosis, peripheral neuropathy, nerve compression, and delusions related to obsessive-compulsive disorders. In skin, pruritogens are released from keratinocytes, lymphocytes, mast cells, and eosinophils during inflammation. These molecules act directly on free nerve endings to induce itch; medicines such as opioids and chloroquine can also trigger itch (see Ikoma et. al., Nature Reviews Neuroscience, 7:535-547 (2006)). Itching following burn is also an extremely serious clinical problem as it hampers the healing process, results in permanent scaring, and negatively impacts quality of life (see Loey et. al., British Journal of Dermatology, 158:95-100 (2008)).

Gain of function mutations of $Na_v1.7$ have been found in approximately 28% of patients with idiopathic small fiber neuropathy (I-SFN); these mutations were found to render dorsal root ganglia neurons hyperexcitable, reducing the threshold of activation and increasing the frequency of evoked firing (see Waxman et. al., Neurology, 78(21): 1635-1643 (2012)). Severe, uncontrollable itch has also been genetically linked to a gain-of-function mutation (1739V) in the sodium channel $Na_v1.7$ in man (see Devigili et. al., Pain, 155(9); pp 1702-7 (2014)). Additionally, the sea-anemone toxin ATX-II has been found to elicit pain and itch in human volunteers after intradermal injection on the forearm; electrophysiology studies revealed that ATX-II enhanced $Na_v1.7$ and $Na_v1.6$ resurgent currents (see Klinger et. al., Molecular Pain, 8:69 (2012)). It has been demonstrated in animal models that selective blockade of $Na_v1.7$ channels can effectively suppress both inflammatory and neuropathic pain, as well as acute and chronic itch, thus blockade of $Na_v1.7$ channels is believed to represent a rational approach to treatment of pain and itch disorders (see Lee et. al., Cell, 157:1-12 (2014)).

Because voltage gated sodium ion channels are ubiquitous in the central and peripheral nervous system, as well as in both cardiac and skeletal muscle, and conservation of structures in the various Alpha-subunits characterizing voltage-gated sodium ion channels implicates the potential for producing serious side effects when utilizing therapeutic agents having a mechanism of action that target inhibition of voltage-gated sodium ion channels, for example, therapeutic agents suitable for use in addressing nociception, cough, or itch disorders, requires therapeutic agents having specificity in their action, for example, discriminating between action upon $Na_v1.5$ sodium ion channels, thought to be important in regulation of cardiac function and action upon $Na_v1.7$ sodium ion channels, thought to be central in inflammatory nociception, cough, or itch and disorders arising from dysfunctional $Na_v1.7$ sodium ion channels.

There remains a need for additional compounds having high potency for inhibiting $Na_v1.7$ sodium ion channels and selective activity for Na$_v$ 1.7 sodium ion channels providing structural variety to facilitate rational development of therapeutic agents for use as a selective Na$_v$ 1.7 sodium ion channel inhibitor.

SUMMARY OF THE INVENTION

In one aspect, the invention provides compounds having selective activity as Na$_v$ 1.7 sodium ion channel inhibitors which have the structure of Formula A-1, or a salt thereof:

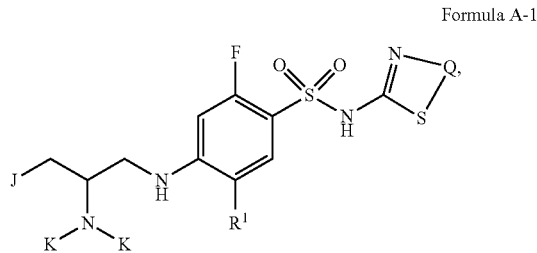

Formula A-1 wherein:
$R^1$ is —CN, —Cl, —Br, or —F;
Q is: (i) —(CH=CR$^2$)—, where $R^2$ is H, or —F; or (ii) —(C=N)—
K is independently for each occurrence, —H or a linear, branched, or cycloalkyl moiety comprising up to 6 carbon atoms; and
J is:
  (a) linear, or branched alkyl of up to 6 carbon atoms which is optionally substituted with: (i) a cycloalkyl of up to 6 carbon atoms; or (ii) aryl which is optionally substituted with one or more halogen or a linear, branched, or cycloalkyl moiety comprising up to 6 carbon atoms;
  (b) trimethylsilyl;
  (c) cycloalkyl of up to 6 carbon atoms which is optionally substituted on one or more carbon atoms thereof with, independently for each occurrence: (i) a linear, branched, or cycloalkyl moiety comprising up to 6 carbon atoms which is optionally substituted with a halogen; or (ii) halogen;
  (d) a bridged-cyclo alkyl of the formula:

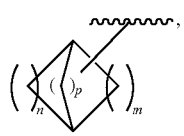

where n, m and p are independently 1 to 3 and the sum of n+m+p is 6 or less, and wherein any of the ring carbon atoms may optionally be substituted with a linear, branched, or cycloalkyl moiety comprising up to 6 carbon atoms; or
  (e) aryl of the formula:

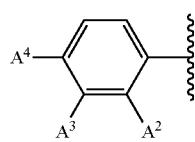

wherein, independently:
$A^2$ is —H, —Br, or —F;
$A^3$ is —H, —Cl, —Br, or —F;
$A^4$ is —H, —Cl, —CH$_3$, —Br, or —F.

In some embodiments it is preferred for the alkyl selected for substituent K to be deuterated.

In some embodiments, it is preferred to select Q in a compound of Formula A-1 to be —C=C(F)—, yielding, along with the remainder of the heterocyclic structure into which Q is bonded, a heterocycle moiety of the structure:

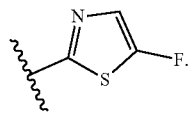

In some embodiments, it is preferred to select Q in a compound of Formula A-1 to be —C=C—, yielding, along with the remainder of the heterocyclic structure into which Q is bonded, a heterocycle moiety of the structure:

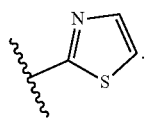 [SMILES: *c1nccs1]

In some embodiments, it is preferred to select Q in a compound of Formula A-1 to be —C=N—, yielding, along with the remainder of the heterocyclic structure into which Q is bonded, a heterocycle of the structure:

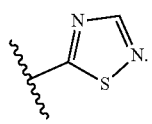

In some embodiments, it is preferred for the compound of Formula A-1 to have the structure of Formula A-2:

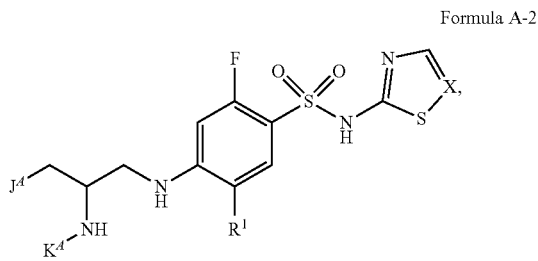

Formula A-2 wherein:
X is N or =C—R$^{2A}$, wherein R$^{2A}$ is —F or —H;
$K^A$ is methyl; and
$J^A$ is a linear, branched or cyclic alkyl of up to 4 carbon atoms which is optionally substituted on one carbon thereof with a linear, branched, or cycloalkyl moiety comprising up to 6 carbon atoms.

In some embodiments, preferably compounds of Formula A have the structure of Formula A-3:

Formula A-3

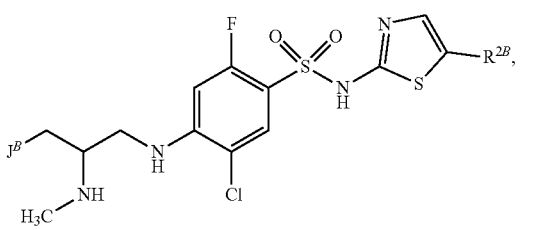

wherein:
R[2B] is —H or —F; and
J[B] is branched alkyl of up to 5 carbon atoms or cyclic alkyl of up to 5 carbon atoms which is optionally substituted on one or more ring carbon atoms with a linear, branched, or cycloalkyl moiety comprising up to 6 carbon atoms, and in some embodiments is preferably tertiary butyl or 1-methyl-cyclopropane.

In some embodiments of the compound of Formula A-3, preferably R[2B] is —F.

In some embodiments it is preferred for the inventive compound to be:
(S)-5-chloro-2-fluoro-4-((2-(methylamino)-3-phenylpropyl) amino)-N-(thiazol-2-yl)benzenesulfonamide;
(S)-5-chloro-2-fluoro-4-((2-(methylamino)-3-phenylpropyl) amino)-N-(1,2,4-thiadiazol-5-yl)-benzenesulfonamide;
(S)-5-chloro-2-fluoro-N-(5-fluorothiazol-2-yl)-4-((2-(methylamino)-3-phenylpropyl)amino)-benzenesulfonamide;
(S)-5-chloro-2-fluoro-4-((3-(4-fluorophenyl)-2-(methylamino)propyl)amino)-N-(thiazol-2-yl)benzenesulfonamide;
(S)-5-chloro-4-((3-cyclohexyl-2-(methylamino)propyl) amino)-2-fluoro-N-(thiazol-2-yl)benzenesulfonamide;
(S)-5-chloro-4-((3-(3-chlorophenyl)-2-(methyl-amino)propyl)-amino)-2-fluoro-N-(thiazol-2-yl)-benzenesulfonamide;
(S)-5-chloro-2-fluoro-4-((2-(methylamino)-3-(p tolyl)propyl)amino)-N-(thiazol-2-yl)-benzenesulfonamide;
(S)-5-chloro-2-fluoro-4-((2-(methylamino)-4-phenylbutyl) amino)-N-(thiazol-2-yl)-benzenesulfonamide;
(S)-5-chloro-2-fluoro-N-(5-fluorothiazol-2-yl)-4-((2-(methylamino)-4-phenylbutyl)amino)-benzenesulfonamide;
(S)-4-((3-(3-bromo-phenyl)-2-(methylamino)-propyl) amino)-5-chloro-2-fluoro-N-(thiazol-2-yl)-benzenesulfonamide;
(S)-4-((3-(2-bromo-phenyl)-2-(methylamino)-propyl) amino)-5-chloro-2-fluoro-N-(thiazol-2-yl)-benzenesulfonamide;
(S)-4-((3-(4-bromo-phenyl)-2-(methylamino)-propyl) amino)-5-chloro-2-fluoro-N-(thiazol-2-yl)-benzenesulfonamide;
(S)-5-chloro-2-fluoro-4-((3-(3-fluorophenyl)-2-(methylamino)-propyl)-amino)-N-(thiazol-2-yl)-benzenesulfonamide;
(S)-5-chloro-2-fluoro-4-((3-(2-fluorophenyl)-2-(methylamino)-propyl)-amino)-N-(thiazol-2-yl)-benzenesulfonamide;
(S)-5-chloro-4-((3-(3,5-difluorophenyl)-2-(methyl-amino)-propyl)amino)-2-fluoro-N-(thiazol-2-yl)-benzenesulfonamide;
(S)-5-chloro-4-((3-(3,4-difluorophenyl)-2-(methyl-amino)propyl)amino)-2-fluoro-N-(thiazol-2-yl)-benzenesulfonamide;
(S)-4-((3-(2-bromo-4-fluorophenyl)-2-(methyl-amino)propyl)-amino)-5-chloro-2-fluoro-N-(thiazol-2-yl)-benzenesulfonamide;
(S)-4-((3-(2-bromo-3-fluorophenyl)-2-(methyl-amino)propyl)-amino)-5-chloro-2-fluoro-N-(thiazol-2-yl)-benzenesulfonamide;
(S)-5-chloro-4-((3-(4-chlorophenyl)-2-(methyl-amino)propyl)amino)-2-fluoro-N-(thiazol-2-yl)-benzenesulfonamide;
(S)-5-chloro-4-((4,4-dimethyl-2-(methylamino)pentyl) amino)-2-fluoro-N-(5-fluorothiazol-2-yl)benzenesulfonamide;
(S)-5-chloro-4-((3-cyclobutyl-2-(methylamino)propyl) amino)-2-fluoro-N-(5-fluorothiazol-2-yl)benzenesulfonamide;
(S)-4-((3-(bicyclo[1.1.1]pentan-1-yl)-2-(methylamino)propyl)-amino)-5-chloro-2-fluoro-N-(5-fluorothiazol-2-yl)-benzenesulfonamide;
(S)-5-chloro-2-fluoro-N-(5-fluorothiazol-2-yl)-4-((2-(methylamino)-3-(1-(trifluoromethyl)cyclopropyl)-propyl) amino)benzenesulfonamide;
(S)-5-chloro-4-((5,5-dimethyl-2-(methylamino)hexyl) amino)-2-fluoro-N-(5-fluorothiazol-2-yl)-benzenesulfonamide;
(S)-5-chloro-2-fluoro-4-((2-(methylamino)-3-(1-(trifluoromethyl)cyclopropyl)-propyl)amino)-N-(thiazol-2-yl)-benzenesulfonamide;
(R)-5-chloro-2-fluoro-N-(5-fluorothiazol-2-yl)-4-((2-(methylamino)-3-(trimethylsilyl)propyl)-amino)benzenesulfonamide;
(S)-5-chloro-4-((3-cyclopropyl-2-(methylamino)propyl) amino)-2-fluoro-N-(5-fluorothiazol-2-yl)-benzenesulfonamide;
(S)-5-chloro-4-((4-cyclopropyl-2-(methylamino)butyl) amino)-2-fluoro-N-(5-fluorothiazol-2-yl)-benzenesulfonamide;
5-chloro-4-(((2S)-3-(2,2-dimethylcyclopropyl)-2-(methylamino)propyl)amino)-2-fluoro-N-(5-fluorothiazol-2-yl)-benzenesulfonamide;
5-chloro-4-(((2S)-3-(2,2-dichlorocyclopropyl)-2-(methylamino)propyl)amino)-2-fluoro-N-(5-fluorothiazol-2-yl)-benzenesulfonamide;
5-chloro-4-(((2S)-3-(2,2-difluorocyclopropyl)-2-(methylamino)propyl)amino)-2-fluoro-N-(5-fluorothiazol-2-yl)-benzenesulfonamide;
(S)-5-chloro-4-((3-cyclopentyl-2-(methylamino)propyl) amino)-2-fluoro-N-(5-fluorothiazol-2-yl)benzenesulfonamide;
(R)-5-chloro-4-((3-cyclopentyl-2-(methylamino)propyl) amino)-2-fluoro-N-(5-fluorothiazol-2-yl)benzenesulfonamide;
(S)-5-chloro-4-((4-cyclobutyl-2-(methylamino)butyl) amino)-2-fluoro-N-(5-fluorothiazol-2-yl)-benzenesulfonamide;
(S)-5-chloro-4-((4,4-dimethyl-2-((methyl-d3)amino)pentyl) amino)-2-fluoro-N-(5-fluorothiazol-2-yl)-benzenesulfonamide;
(S)-5-chloro-2-fluoro-4-((3-(1-(fluoromethyl)cyclopropyl)-2-(methylamino)propyl)amino)-N-(5-fluorothiazol-2-yl) benzenesulfonamide;
(S)-5-chloro-2-fluoro-N-(5-fluorothiazol-2-yl)-4-((2-(methylamino)-3-(1-methylcyclopropyl)propyl)amino)benzenesulfonamide;
(S)-5-chloro-2-fluoro-N-(5-fluorothiazol-2-yl)-4-((2-(methylamino)-4-(1-methylcyclopropyl)butyl)amino)benzenesulfonamide;

(S)-5-chloro-4-((2-(dimethylamino)-3-(1-methylcyclopropyl)propyl)amino)-2-fluoro-N-(5-fluorothiazol-2-yl)benzenesulfonamide;

(R)-5-chloro-4-((2-(ethylamino)-3-(trimethylsilyl)propyl)amino)-2-fluoro-N-(5-fluorothiazol-2-yl)benzenesulfonamide;

(S)-5-chloro-2-fluoro-N-(5-fluorothiazol-2-yl)-4-((2-(propylamino)hexyl)amino) benzenesulfonamide;

(S)-5-chloro-2-fluoro-N-(5-fluorothiazol-2-yl)-4-((2-(isopropylamino)hexyl)amino)-benzenesulfonamide; or (S)-5-cyano-4-((4,4-dimethyl-2-(methylamino)pentyl)amino)-2-fluoro-N-(5-fluorothiazol-2-yl)benzenesulfonamide, or a pharmaceutically acceptable salt of any thereof.

In one aspect the invention provides a pharmaceutical composition comprising at least one compound of Formula A-1, Formula A-2, or Formula A-3, or a salt thereof, and at least one pharmaceutically acceptable excipient adapted for administration to a patient via any pharmaceutically acceptable route, including dosage forms for oral, intravenous, infusion, subcutaneous, transcutaneous, intramuscular, intradermal, transmucosal, or intramucosal routes of administration.

In one aspect this invention provides also a pharmaceutical composition comprising a pharmaceutical carrier, an effective amount of at least one compound of Formula A-1, Formula A-2, or Formula A-3, or a salt thereof, an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

In one aspect the invention provides also a method of treatment, management, alleviation or amelioration of conditions or disease states which can be treated, managed, alleviated or ameliorated by specific inhibiting of $Na_v$ 1.7 channel activity, the method comprising administering to a patient in need thereof a composition comprising at least one compound of Formula A-1, Formula A-2, or Formula A-3, or a salt thereof, in an amount providing a serum level of at least one said compound sufficient to effect said treatment, management, alleviation or amelioration of said conditions or disease states. Preferably the condition or disease state to be treated, managed, alleviated or ameliorated include itch, cough, or pain, for example, acute pain or a chronic pain disorder. In some embodiments, the condition is preferably pain, more preferably, chronic pain.

DETAILED DESCRIPTION OF THE INVENTION

As mentioned above, the invention provides compounds believed to have selective activity as $Na_v$ 1.7 sodium ion channel inhibitors which have the structure of Formula A, or a salt thereof:

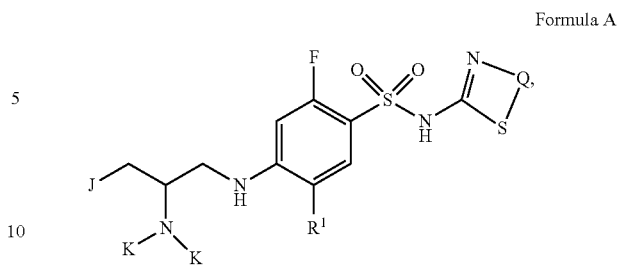

Formula A wherein Q, J, K and $R^1$ are defined herein above.

Compounds of the invention exhibit a potency ($IC_{50}$) for $Na_v$ 1.7 sodium channels of less than about 2000 nanomolar when assayed in accordance with IonWorks® assay technique described herein. In some embodiments it is preferred for compounds of the invention to exhibit a potency for $Na_v$ 1.7 sodium channels of less than about 1000 nanomolar, more preferably less than about 500 nanomolar when assayed in accordance with IonWorks® assay technique described herein.

Compounds of the invention exhibit at least 10-fold selectivity for $Na_v$ 1.7 sodium channels over $Na_v$ 1.5 sodium channels when functional potency for each channel are compared using the IonWorks® assay technique described herein. In some embodiments, it is preferred for compounds of the invention to have at least a 30-fold selectivity for $Na_v$ 1.7 sodium channels over $Na_v$ 1.5 sodium channels when functional potency for each channel are compared using the IonWorks® assay technique described herein, more preferably at least about a 50-fold selectivity for $Na_v$ 1.7 sodium channels over $Na_v$ 1.5 sodium channels when functional potency for each channel are compared using the IonWorks® assay technique described herein.

Compounds of the invention and formulations comprising compounds of the invention are believed to be useful in providing treatment, management, alleviation or amelioration of conditions or disease states which can be treated, managed, alleviated or ameliorated by specific inhibiting of $Na_v$ 1.7 channel activity. Examples of disease states which are believed to be desirably affected using such therapy include, but are not limited to, inhibiting acute pain, peri-operative, post-operative and neuropathic pain, for example, postherpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias, pruritis or cough.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

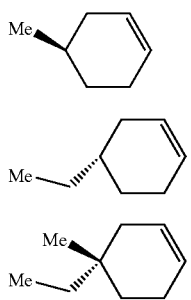

Illus-1

Illus-2

Illus-3

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents on a compound or moiety appended to the core structure of a compound means that one substituent of the group of substituents specified is present, and more than one substituent may be bonded to any of the chemically accessible bonding points of the core.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula A-1, Formula A-2, or Formula A-3, that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula A-1, Formula A-2, or Formula A-3 to a compound of Formula A-1, Formula A-2, or Formula A-3, respectively, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

The term "substituted" means that one or more of the enumerated substituents can occupy one or more of the bonding positions on the substrate typically occupied by "—H", provided that such substitution does not exceed the normal valency rules for the atom in the bonding configuration presented in the substrate, and that the substitution ultimately provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated substituents for the specified substrate can be present on the substrate in a bonding position normally occupied by the default substituent normally occupying that position. For example, a default substituent on the carbon atoms of an alkyl moiety is a hydrogen atom, an optional substituent can replace the default substituent.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, an "acyl" substituent may be equivalently described herein by the term "acyl", by typographical representations "R'—(C=O)—" or "R'—C(O)—", or by a structural representation:

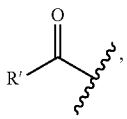

equally, with no differentiation implied using any or all of these representations;

alkyl" (including the alkyl portions of other moieties, such as trifluoromethyl-alkyl- and alkoxy-) means an aliphatic hydrocarbon moiety comprising up to about 20 carbon atoms (for example, a designation of "$C_{1-20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms and may also be designated herein "$C_{1-8}$-alkyl". The term "alkyl" is further defined by "Linear", "Branched" or "Cyclic. Where the term "alkyl" is indicated with two hyphens (i.e., "-alkyl-" it indicates that the alkyl moiety is bonded in a manner that the alkyl moiety connects the substituents on either side of it, for example, "-alkyl-Cl" indicates an alkyl moiety connecting a chloride substituent to the moiety to which the alkyl is bonded on the other end; it will be appreciated that the term alkyl includes alkyls in which one or more, up to all, of the hydrogen atoms therein have been replaced with deuterium.

The term "linear-alkyl" includes alkyl moieties which comprise a hydrocarbon chain with no aliphatic hydrocarbon "branches" appended to it, although other substituents may replace a C—H bond on the hydrocarbon chain. Examples of linear alkyl include, but are not limited to, methyl-, ethyl-, n-propyl-, n-butyl-, n-pentyl- or n-hexyl-.

The term "branched-alkyl" is a moiety comprising a main hydrocarbon chain of up to the maximum specified number of carbon atoms with a lower-alkyl chain appended to one or more of the carbon atoms comprising, but not terminating, the main hydrocarbon chain. A branched alkyl moiety therefore comprises at least 3 carbon atoms in the main chain. Examples of branched alkyl moieties include, but are not limited to, t-butyl-, neopentyl-, or 2-methyl-4-ethyl-hexyl- The term "cyclic-alkyl" (equivalently "cycloalkyl") means a moiety having a main hydrocarbon chain forming a mono- or bicyclo-cyclic aliphatic moiety comprising at least 3 carbon atoms (the minimum number necessary to provide a monocyclic moiety) up to the maximum number of specified carbon atoms, generally 8 for a monocyclic moiety and 10 for a bicyclic moiety. Examples of cycloalkyl moieties include, but are not limited to, cyclopropyl, cyclobutyl, cyclopentyl or cyclohexyl. The term cyclic-alkyl (equivalently "cycloalkyl") also includes non-aromatic, fused multicyclic ring system comprising up to 20 carbon atoms which may optionally be substituted;

The term "bridged-cyclo alkyl" means a cycloalkyl comprising 4 or more carbon atoms which has an alkyl bridge spanning two non-adjacent carbon atoms (thus forming a bicyclic structure), which bridged-cyclo alkyl may be bonded to a substrate via any ring carbon atom, thus having the structure:

where n, m and p are independently 1 to 3, the sum of n+m+p is 6 or less, and wherein any of the ring carbon atoms may optionally be substituted with a linear, branched, or cycloalkyl moiety comprising up to 6 carbon atoms;

The term "lower cyclic alkyl" means a cycloalkyl comprising less than 6 carbon atoms, e.g., cyclopropyl, cyclobutyl, cyclopentyl, cyclohexyl;

As used herein, when the term "alkyl" is modified by "substituted" or "optionally substituted", it means that one or more C—H bonds in the alkyl moiety group is substituted, or optionally may be substituted, by a substituent bonded to the alkyl substrate which is called out in defining the moiety.

"lower alkyl" means a linear, branched, or cycloalkyl moiety comprising up to 6 carbon atoms; non-limiting examples of suitable lower alkyl groups include methyl, ethyl, n-propyl, isopropyl, n-butyl, t-butyl, n-pentyl, isopentyl, neopentyl, n-hexyl, and the like;

Heterocycloalkyl—means a non-aromatic saturated monocyclic or multicyclic ring system comprising 3 to 10 ring atoms, preferably 5 to 10 ring atoms, in which one or more of the atoms in the ring system is an element other than carbon, for example nitrogen (e.g. piperidyl- or pyrrolidinyl), oxygen (e.g. furanyl and tetrahydropyranyl) or sulfur (e.g. tetrahydrothiopheneyl and tetrahydrothiopyranyl); and wherein the heteroatoms can be alone or in combination provided that the moiety does not contain adjacent oxygen and/or sulfur atoms present in the ring system, for example:

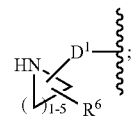

where a structural formula represents bonding between a moiety and a substrate using a the bonding line that terminates in the middle of the structure, for example the following representations:

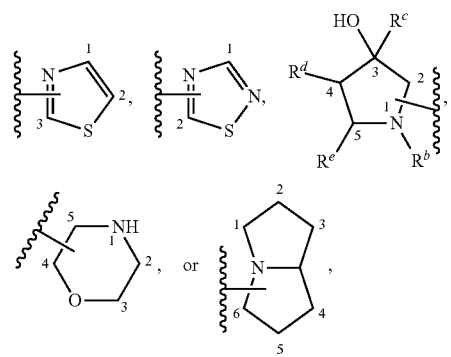

whether or not numbered the structure indicates that unless otherwise defined the moiety may be bonded to the substrate through any available ring atom, for example, the numbered atoms of the example moieties;

"halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —CF$_3$; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

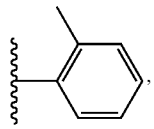

indicates that the methylphenyl moiety is bonded to a substrate through a carbon atom ortho to the methyl substituent, while a bond representation terminated with a wavy line and drawn into a structure without any particular indication of a atom to which it is bonded indicates that the moiety may be bonded to a substrate via any of the atoms in the moiety which are available for bonding as described in the examples above.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPSPharmSciTech.*, 5, article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

This invention also includes the compounds of this invention in isolated and purified form obtained by routine techniques. Polymorphic forms of the compounds of Formula A-1, Formula A-2, or Formula A-3, and of the salts, solvates and prodrugs thereof, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

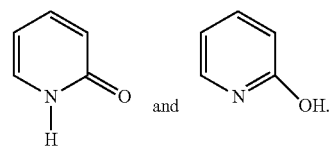 [SMILES: O=c1cccc[nH]1 ; Oc1ccccn1]

In particular, compounds of the invention presented herein having a portion of their structure represented by the structural drawing A is intended to include all other tautomeric forms, for example the tautomeric form presented by structural drawing B in the following two examples:

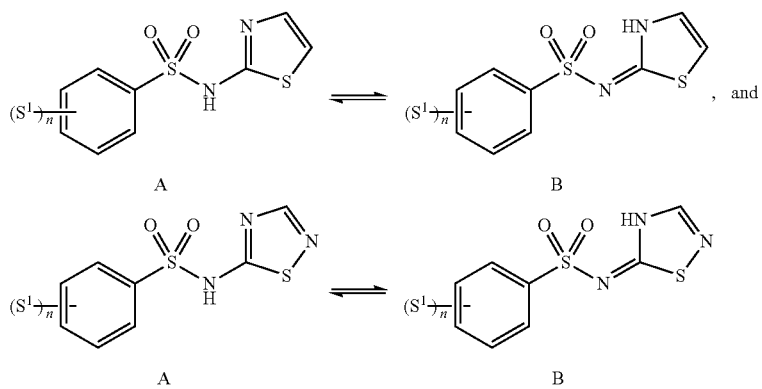

where (S1)n is one to five substituents on the aryl ring, thus, any structural drawing representation where tautomerism is possible is intended to include all tautomeric forms within the scope of the structures represented thereby.

Oxygen and nitrogen atoms in a structure may be represented equivalently as protonated on a lone pair of electrons or in unprotonated form, and both forms are contemplated where either structure is presented, for example, the protonated form A and unprotonated form B of the amine illustrated below:

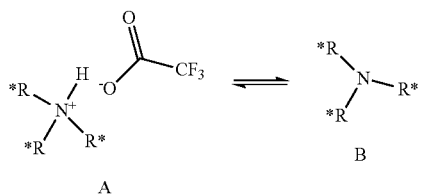

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

In general, salts of compounds are intended to be pharmaceutically acceptable salts within the scope of the invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups are known, for example, as by reference to standard textbooks, for example, T. W. Greene et al, Protective Groups in organic Synthesis (1991), Wiley, New York.

When a variable (e.g., aryl, cycloalkyl, $R^{XY}$ etc.) appears more than once in any moiety or in any compound of the invention, the selection of moieties defining that variable for each occurrence is independent of its definition at every other occurrence unless specified otherwise in the local variable definition.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^2H$, $^3H$, $^{11}C$, $^{13}C$, $^{14}C$, $^{13}N$, $^{15}N$, $^{15}O$, $^{17}O$, $^{18}O$ $^{31}P$, $^{32}P$, $^{35}S$, $^{18}F$, and $^{36}Cl$, $^{123}I$ and $^{125}I$. It will be appreciated that other isotopes may be incorporated by known means also.

Certain isotopically-labeled compounds of the invention (e.g., those labeled with $^3H$, $^{11}C$ and $^{14}C$) are recognized as being particularly useful in compound and/or substrate tissue distribution assays using a variety of known techniques. Tritiated (i.e., $^3H$) and carbon-14 (i.e., $^{14}C$) isotopes are particularly preferred for their ease of preparation and detection. Further, substitution of a naturally abundant isotope with a heavier isotope, for example, substitution of protium with deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

As used herein, the term "pharmaceutical composition" comprises at least one pharmaceutically active compound and at least one excipient, and is intended to encompass both the combination of the specified ingredients in the specified amounts, and any product which results, directly or indirectly, from combination of the specified ingredients in the specified amounts. As will be appreciated by the ordinarily skilled artisan, excipients are any constituent which adapts the composition to a particular route of administration or aids the processing of a composition into a dosage form without itself exerting an active pharmaceutical effect. A bulk composition is material that has not yet been formed into individual units for administration As mentioned above, in one aspect the invention provides compositions suitable for use in selectively inhibiting $Na_v$ 1.7 sodium channels found in sensory and sympathetic neurons, comprising at least one compound of the invention (as defined herein, for example one or more compounds of Formula A-1, Formula A-2, or Formula A-3, or a salt thereof) and at least one pharmaceutically acceptable carrier (described below). It will be appreciated that pharmaceutical formulations of the invention may comprise more than one compound of the invention, for example, the combination of two or three compounds of the invention, each present by adding to the formulation the desired amount of the compound in a pharmaceutically acceptably pure form. It will be appreciated that compositions of the invention may comprise, in addition to one or more of the compounds of the invention, one or more additional compounds which also have pharmacological activity, for example, as described herein below. Such formulations are believed to have utility in the treatment, management, amelioration or in providing therapy for diseases or conditions related to pain, for example, acute pain, chronic pain, inflammatory pain, or neuropathic pain disorders, or related to pruritic disorders, or cough disorders.

In one aspect this invention provides also pharmaceutical compositions which comprise in addition to at least one pharmaceutically acceptable carrier and an effective amount of at least one compound of the invention (e.g, a compound of Formula A-1, Formula A-2, or Formula A-3, or a salt thereof), an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

While compositions of the invention may be employed in bulk form, it will be appreciated that for most applications compositions will be incorporated into a dosage form suitable for administration to a patient, each dosage form comprising an amount of the selected composition which contains an effective amount of said one or more compounds of Formula A-1, Formula A-2, or Formula A-3. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for administration through tissues of the oral cavity, for example, a rapidly dissolving tablet, a lozenge, a solution, a gel, a sachet or a needle array suitable for providing intramucosal administration; (iii) a dosage form adapted for administration via the mucosa of the nasal or upper respiratory cavity, for example a solution, suspension or emulsion formulation for dispersion in the nose or airway; (iv) a dosage form adapted for transdermal administration, for example, a patch, cream or gel; (v) a dosage form adapted for intradermal administration, for example, a microneedle array; (vi) a dosage form adapted for intravenous (IV) infusion, for example, over a prolonged period using an I.V. infusion pump; (vii) a dosage form adapted for intramuscular administration (IM), for example, an injectable solution or suspension, and which may be adapted to form a depot having extended release properties; (viii) a dosage form adapted for drip intravenous administration (IV), for example, a solution or suspension, for example, as an IV solution or a concentrate to be injected into a saline IV bag; (ix) a dosage form adapted for subcutaneous administration; or (x) a dosage form adapted for delivery via rectal or vaginal mucosa, for example, a suppository.

For preparing pharmaceutical compositions containing compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier". Typically formulations may comprise up to about 95 percent active ingredient, although formulations with greater amounts may be prepared.

For preparing pharmaceutical compositions containing compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or for example, solution stablizing or emulsifying agents which may adapt the formulation to a desired route of administration, for example, which provide a formulation for injection, for example, intramuscular or intravenous routes of administration or administration via IV or diffusion pump infusion or other form parenteral administration, or for oral administration, for example, via absorption from the gastrointestinal tract, or for transdermal or transmucosal administration, for example, via adhesive skin "patch" or buccal administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid, semi-solid and liquid form preparations can be adapted to a variety of modes of administration, examples of which include, but are not limited to, powders, dispersible granules, mini-tablets, beads, which can be used, for example, for tableting, encapsulation, or direct administration. In addition, liquid form preparations include, but are not limited to, solutions, suspensions and emulsions which for example, but not exclusively, can be employed in the preparation of formulations intended for ingestion, inhalation or intravenous administration (IV), for example, but not limited to, administration via drip IV or infusion pump, intramuscular injection (IM), for example, of a bolus which is released over an extended duration, direct IV injection, or adapted to subcutaneous routes of administration.

Other routes of administration which may be contemplated include intranasal administration, or for administration to some other mucosal membrane. Formulations prepared for administration to various mucosal membranes may also include additional components adapting them for such administration, for example, viscosity modifiers.

Although in some embodiments, compositions suitable for use in a solid oral dosage form, for example, a tablet or quick-melt mouth-dissolving formulation are preferable routes of administration for a compound of the invention or a salt thereof, a composition of the invention may be formulated for administration via other routes mentioned above. Examples include Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

For example, the compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, $20^{th}$ Edition, (2000), Lippincott Williams & Wilkins, Baltimore, Md.

The actual dosage employed may be varied depending upon the requirements of the patient and the severity of the condition being treated. Determination of the proper dosage regimen for a particular situation is within the skill in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, $56^{th}$ Edition, 2002 (published by Medical Economics company, Inc. Montvale, N.J. 07645-1742), or the Physician's Desk Reference, $57^{th}$ Edition, 2003 (published by Thompson PDR, Montvale, N.J. 07645-1742); the disclosures of which is incorporated herein by reference thereto. For convenience, the total daily dosage may be divided and administered in portions during the day as required or delivered continuously.

In another embodiment the present invention is believed to provide for treatment, management, prevention, alleviation or amelioration of conditions or disease states which can be treated, managed, prevented, alleviated or ameliorated by specific inhibition of $Na_v$ 1.7 channel activity. Some examples are pain conditions, pruritic conditions and cough conditions. Examples of pain conditions include, but are not limited to, acute pain, perioperative pain, preoperative pain, postoperative pain, neuropathic pain, for example, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associated with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmennorhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain, pruritic conditions, and cough conditions.

In some embodiments in which it is desired to treat a pain disorder, preferably the disorder is a chronic pain disorder.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during the treatment cycle.

In accordance with the present invention, treatment, alleviation, amelioration, or management of a disease state amenable to treatment by inhibiting $Na_v1.7$ channel activity, for example, one or more of the conditions or disease states mentioned above, comprises administering to a patient in need thereof an effective amount of one or more compounds of the invention, as defined herein, for example, a compound of Formula A-1, Formula A-2, or Formula A-3, or a pharmaceutically acceptable salt thereof. In some embodiments, as mentioned above, it is preferred for the compound of the invention to be present in a pharmaceutical composition.

In general, in whatever form administered, the dosage form administered will contain an amount of at least one compound of the invention, or a salt thereof, which will provide a therapeutically effective serum level of the compound meeting or exceeding the minimum therapeutically effective serum level on a continuous basis throughout the period during which treatment is administered. As mentioned above, a composition of the invention can incorporate additional pharmaceutically active components or be administered simultaneously, contemporaneously, or sequentially with other pharmaceutically active compositions as may be additionally needed in the course of providing treatment.

In one aspect this invention provides also a pharmaceutical composition comprising a pharmaceutical carrier, an effective amount of at least one compound of the invention, for example, a compound of Formula A-1, Formula A-2, or Formula A-3, and an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during the treatment cycle.

In the examples that follow certain of the exemplified compounds, or salts thereof, are prepared as pure enantiomers, or prepared from enantiopure precursors, or are isolated using chiral separation methods after synthesis, for example, chiral chromatography. After isolation of chiral compounds the absolute stereochemistry of the isolated compound was not determined in every example. Accordingly, where pure isomers have been prepared but the absolute configuration has not been verified, the enantiomer isolated in pure form is specified by the following convention.

Unless indicated otherwise in the text, where present, isomers of example compounds were not separated. Unless indicated otherwise in the text, where isomers were separated into fractions containing an excess of a particular isomer, for example, a fraction containing an excess of an optical isomer, which separation may be accomplished, for example, by super critical fluid chromatography, absolute stereochemistry of separated isomers was not determined unless indicated otherwise.

Where a reaction scheme appearing in an example employs a compound having one or more stereocenters, the stereocenters are indicated with an asterisk, as shown below in illustration compound Def-1.

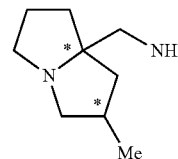

Def-1

Accordingly, Def-1 consists of the following pairs of isomers: (i) Trans-isomers ((2R,7aS)-2-methylhexahydro-1H-pyrrolizin-7a-yl)methanamine (Compound ABC-1) and ((2S,7aR)-2-methylhexahydro-1H-pyrrolizin-7a-yl)methanamine (Compound ABC-2); and (ii) Cis-isomers ((2R,7aR)-2-methylhexahydro-1H-pyrrolizin-7a-yl)methanamine (Compound ABC-3) and ((2S,7aS)-2-methylhexahydro-1H-pyrrolizin-7a-yl)methanamine (Compound ABC-4).

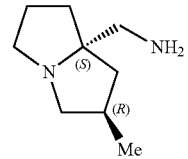

ABC-1

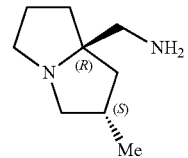

ABC-2

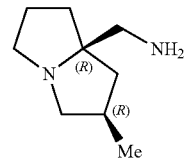

ABC-3

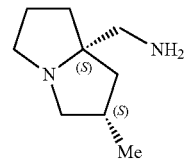

ABC-4

When the compound is prepared and separated into pure enantiomers, albeit without determining the absolute configuration of each enantiomer of the compound, the product will be identified in the title using both enantiomer names, e.g., where ABC-1 and ABC-2 are prepared and separated into pure enantiomers, the title will read "preparation of ((2R,7aS)-2-methylhexahydro-1H-pyrrolizin-7a-yl)methanamine and ((2S,7aR)-2-methylhexahydro-1H-pyrrolizin-7a-yl)methanamine. In some instances where enantiomeric compounds are prepared the designation (Cis) or (Trans) may be appended to the name to clarify the relationship of the stereo centers present in the two stereoisomers. As will be appreciated, identification of each product in the experimental preparation as "ABC-enantiomer A" or "ABC-enantiomer B" is not an association of the enantiomer prepared and isolated with any stereospecific name, only that both said enantiomers were prepared and isolated in increased enantiopurity without determination of the absolute configuration of either compound thus prepared.

Where isomeric compounds are prepared in a racemic mixture, asterisks will be inserted into the structural representation to indicate the stereocenters, but the title will reference the preparation of both enantiomers, e.g., where ABC-3 and ABC-4 are prepared as a racemate, the title will read "preparation of ((2R,7aR and 2S,7aS)-2-methylhexahydro-1H-pyrrolizin-7a-yl)methanamine".

Those skilled in the art will appreciate that treatment protocols utilizing at least one compound of the invention, as described herein, may be varied according to the needs of the patient. Thus, compounds of the invention used in the methods of this invention may be administered in variations of the protocols described above. For example, the compounds of this invention may be administered discontinuously rather than continuously during the treatment cycle.

The following examples are presented to further illustrate compounds of the invention, but, with reference to the general formula presented above, they are not presented as limiting the invention to these specifically exemplified compounds.

EXAMPLES

Examples of the preparation of compounds of the invention are shown next. In each of the Examples, the identity of the compounds prepared were confirmed by a variety of techniques. In all cases the compounds were analyzed by LC/MS or HPLC.

Where utilized, Prep HPLC was carried out on a Gilson 281 equipped with a Phenomenexd Synergi C18, 100 mm×21.2 mm×5 micron column. Conditions included a flow rate of 25 mL/min., eluted with a 0-40% acetonitrile/water eluent comprising 0.1% v/v TFA.

LC/MS determinations used either an Agilent YMC J'Sphere H-80 (3×50 mm) 5 µm column using mobile phase containing A: 0.1% Trifluoroacetic acid in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer or an Agilent TC-C18 (2.1×50 mm) 5 m column using mobile phase containing A: 0.0375% Trifluoroacetic acid in water and B: 0.01875% Trifluoroacetic acid in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

For some compounds, the identity of the compound was verified by proton NMR. Proton NMR was were acquired using a Varian Unity-Inova 400 MHz NMR spectrometer equipped with a either a Varian 400 ATB PFG 5 mm, Nalorac DBG 400-5 or a Nalorac IDG 400-5 probe in accordance with standard analytical techniques, unless specified otherwise, and results of spectral analysis are reported.

Throughout the Examples section, the following abbreviations are used to indicate various reagents, substituents and solvents: ACN=acetonitrile; AcOH=acetic acid; Boc=tert-butoxycarbonyl; $Boc_2O$=di-tert-butyl carbonate; Bn=Benzyl; DABCO=1,4-diazabicyclo[2.2.2]octane; DAST=diethylaminosulfur trifluoride; DCE=dichloroethane; DCM=dichloromethane; DEAD=diethylazodicarboxylate; DIAD=diisopropylazodicarboxylate; DIPEA=diisopropylamine; DMAP=4-dimethylaminopyridine; DMB (2,4-dimethoxybenzyl-); DMF=dimethylformamide; DMP=Dess-Martin Periodinane; DMS=dimethylsulfide; DMSO=dimethylsulfoxide; DPPA=diphenylphosphoryl azide; dppf=1,1'-bis(diphenylphosphino)-ferrocene; DTAD=di-tert-butylazodicarboxylate; EtOAc=ethyl acetate; EtOH=ethanol; Fmoc=fluorenyloxycarbonyl; HATU=1-[Bis(dimethylamino)methylene]-1H-1,2,3-triazolo[4,5-b]pyridinium-3-oxide-hexafluorophosphate; Hex=hexanes; HMPA=hexamethylphosphoramide; HPLC=high-performance liquid chromatography; IPA=isopropyl alcohol; LC/MS=liquid chromatography/mass spectrometry; LDA=lithium diisopropylamide; LG=leaving group; LiHMDS=lithium bis(trimethylsilyl)amide; MeOH=methanol; LRMS=low resolution mass spectrometry; MOM=methoxymethyl; MOMCl=methyl chloromethyl ether; MsCl=methanesulfonyl chloride; NMP=N-methylpyrrolidone; Pd/C=palladium on carbon; $Pd_2(dba)_3$=tris(dibenzylideneacetone)dipalladium(0); PE=petroleum ether; PG=protecting group; PMB=para-methoxybenzyl; PMBCl=para-methoxybenzyl chloride; Prep-TLC=preparative thin layer chromatography; Py=pyridine; Selectfluor=1-(chloromethyl)-4-fluoro-1,4-diazoniabicyclo[2.2.2]octane ditetrafluoroborate; SFC=Supercritical Fluid Chromatography; TBS=tert-butyldimethylsilyl; TBS-Cl=tert-butyldimethylsilyl chloride; THF=Tetrahydrofuran; TFA=trifluoroacetic acid; TFAA=trifluoroacetic acid anhydride; TsOH=para-toluenesulfonic acid; UV=ultraviolet; Xantphos=4,5-Bis(diphenylphosphino)-9,9-dimethylxanthene.

As illustrated in Scheme G-A, in general, compounds of the invention can be prepared by acylation of protected aryl-substituted or heteroaryl-substituted amines (A-2, PG=protecting group which is, for example, but not limited to, Boc, DMB, PMB, MOM) or unprotected aryl-substituted or heteroaryl-substituted amines (A-2, PG=H) with the appropriately functionalized sulfonyl chloride (A-1, LG=leaving group, which is, for example, but not limited to, F, Cl, Br) to afford intermediates of type A-3. Intermediates of type A-3 can undergo nucleophilic aromatic substitution reactions with protected diamines (A-4, wherein $R^2$ contains protected amine functionality, see Scheme C, below) to afford final compounds of type A-5, which are in turn deprotected to yield A-6. Amines of type A-4 can be commercially available or synthesized as demonstrated in Schemes 1 to 4 and as generally illustrated in Scheme G-B.

Scheme G-A

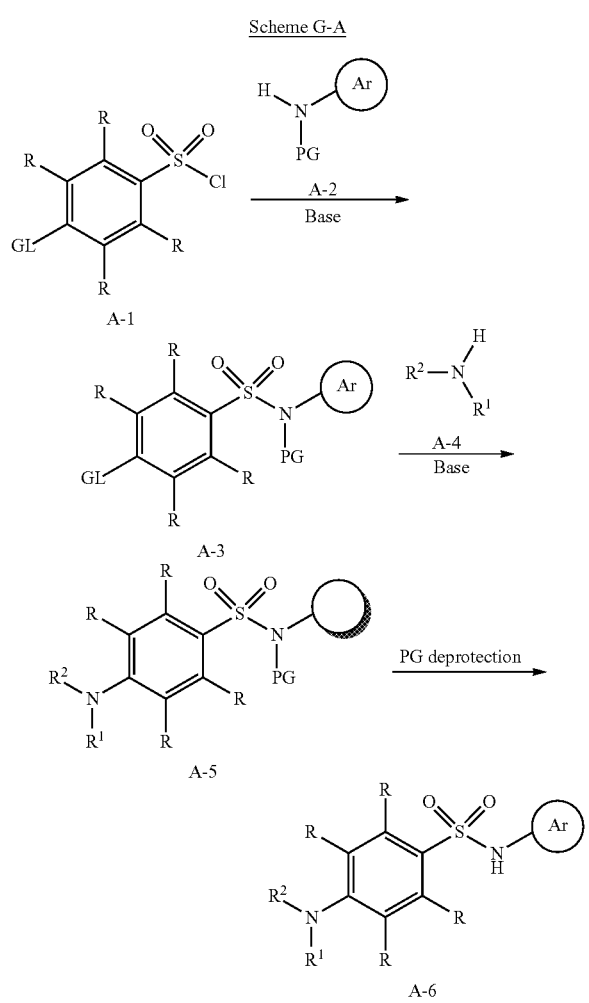

As illustrated in Schemes G-B, G-C, and G-D, below, suitable diamine precursors for use in preparing compounds of the invention can be prepared, starting by alkylation under basic conditions using R—X reagents of protected aminoacetonitriles of type B-1 (wherein PG is a protecting group on the amine nitrogen, for example, but not limited to, Boc, Cbz, Bn) to afford intermediates of type B-2. These B-2 intermediates are subsequently reduced to afford protected diamines of type B-3, which can be used as "A-4" reagents illustrated in Scheme G-A.

Scheme G-B

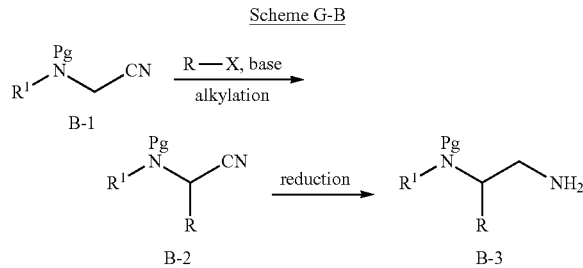

Using an alternative method, suitable diamines can be prepared in accordance with the general procedure shown in Scheme C, wherein reduction of protected amino acids of type C-1 (where PG is a protecting group on the amine portion of the amino acid, which is, for example, but not limited to, Boc, Cbz, Bn) to afford intermediates of type C-2. Intermediates of type C-2 can be transformed into amines of type C-3 (i.e., by employing a phthalimide Mitsunobu reaction followed by treatment with hydrazine). Thus prepared, these C-3 amines can be used as the A-4 reagent in the substitution reactions depicted in Scheme G-A.

Scheme G-C

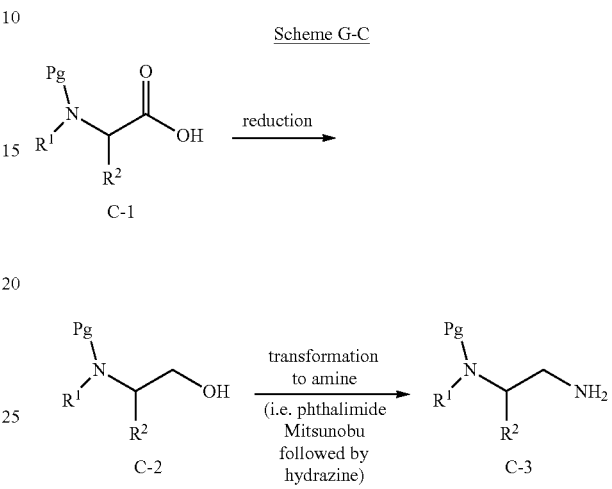

Suitable diamines can be prepared also in accordance with the general procedure shown in Scheme G-D. Scheme G-D illustrates condensation of aldehydes with phosphonates of type D-1 (where PG is a protecting group on the amine portion of the amino acid, for example, but not limited to, Boc, Cbz, Bn and Y=cyano or ester) to afford intermediate olefins of type D-2. Type D-2 intermediates are converted to amines of type D-3 through direct reduction of the cyano group and olefin or reduction of the olefin and ester followed by alcohol to amine interconversion. Thus prepared, these D-3 amines can be used as the A-4 reagent in the substitution reactions depicted in Scheme G-A.

Scheme G-D

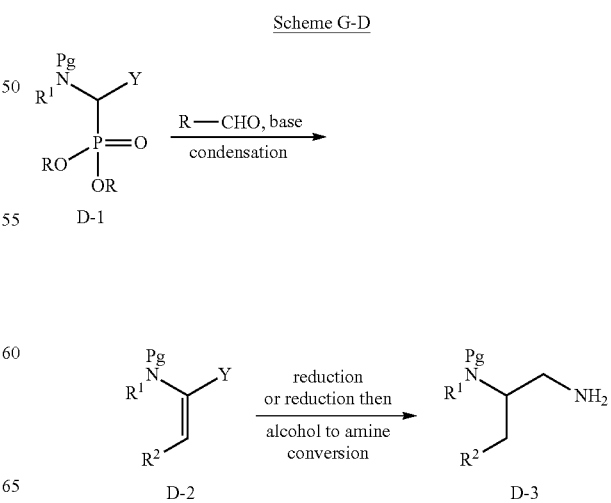

Example 1A (S)-5-chloro-2-fluoro-4-((2-(methyl-amino)-3-phenylpropyl)amino)-N-(thiazol-2-yl)benzenesulfonamide (1-7, Method A)

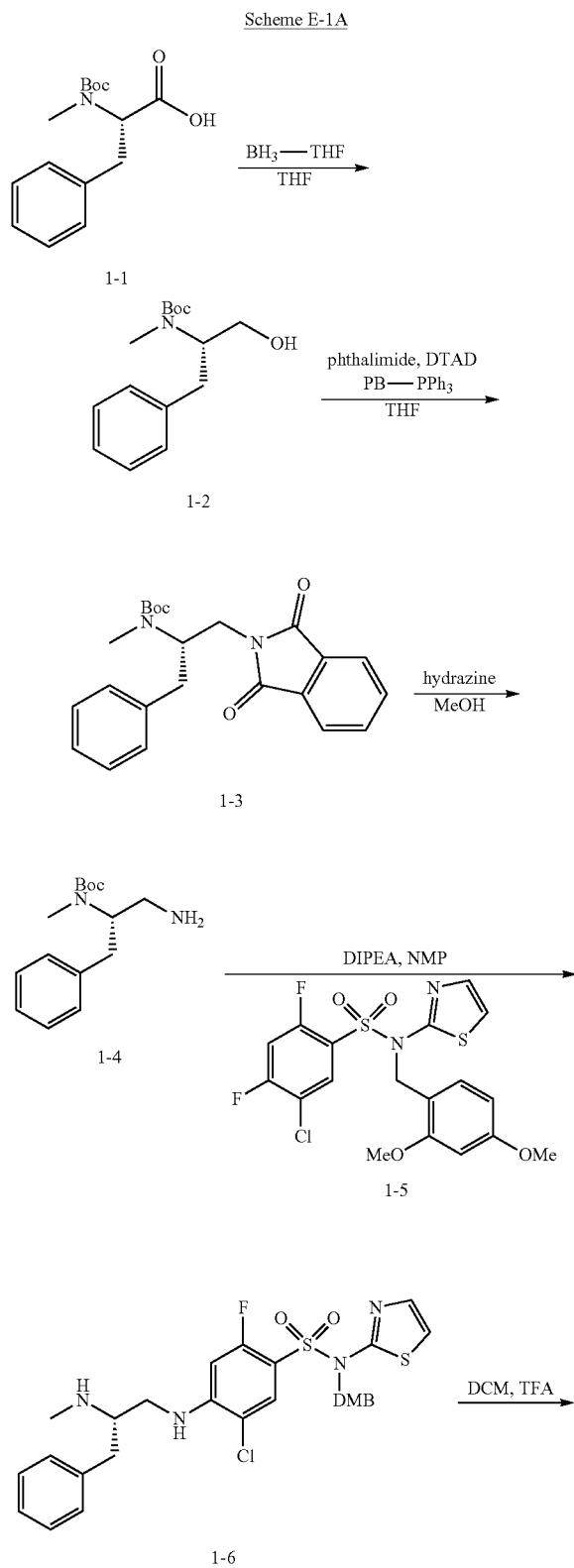

Scheme E-1A

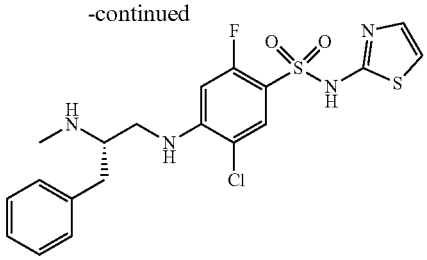

1-7

Preparation of (S)-tert-butyl (1-hydroxy-3-phenylpropan-2-yl)(methyl)carbamate (1-2)

To a flask containing commercially available BOC—N-ME-PHE-OH (1-1) (1 g, 3.58 mmol) was added anhydrous THF (10 mL) then cooled to 0° C. (ice water bath) while stirring under an atmosphere of nitrogen. Then added a 1N solution of Borane/Tetrahydrofuran complex (12 mL, 12.00 mmol). The reaction mixture was then permitted to stir at 0° C. for 10 minutes, then warmed to room temperature. Reaction progress was followed by LC/MS. After 30 min at room temperature, the reaction mixture was cooled to 0° C. (ice water bath) then uncapped & quenched by slow addition of a saturated solution of NH$_4$Cl. The reaction mixture was then warmed to room temperature, stirred for 15 minutes then suspended in EtOAc. Organics were separated and the separated material was washed with saturated NaHCO$_3$ (2×), then H$_2$O, then brine; and dried over Na$_2$SO$_4$. The resultant collected organics were filtered and concentrated to provide (1-2); [M+H]+m/z: observed=266.2; calculatd=266.3.

Preparation of (S)-tert-butyl (1-(1,3-dioxoisoindolin-2-yl)-3-phenylpropan-2-yl)(methyl)carbamate (1-3)

To a flask containing (S)-tert-butyl (1-hydroxy-3-phenylpropan-2-yl)(methyl)carbamate (1-2) (640 mg, 2.412 mmol), resin bound (PS resin) triphenylphosphine (1.32 g, 3.96 mmol), & phthalimide (468 mg, 3.18 mmol), was added anhydrous THF (5 mL), then added DTAD (760 mg, 3.30 mmol). The reaction mixture was then stirred at room temperature. The reaction progress was followed by LC/MS. After 30 minutes at room temperature the reaction mixture was diluted with DCM, then filtered. The filtrate was suspended in EtOAc, washed with saturated NaHCO$_3$, then H$_2$O, then brine; and the organics thus collected were dried over Na$_2$SO$_4$, filtered & concentrated. Purification was accomplished by silica gel chromatography (0-50% EtOAc/Hex; 80 g ISCO). The desired fractions thus collected were concentrated under reduced pressure and the resulting residue was suspended in mixed MeCN/DMSO and purified (without workup) by reverse phase chromatography (2 injections) (10-90% MeCN/H2O; 0.1% TFA in AQ; 20 min gradient; Waters 30×150 mm Sunfire 5 micron C18 column; Flow=40 mL/min); desired fractions free based (suspended in EtOAc, washed with saturated NaHCO$_3$, then H$_2$O, then brine; organics dried over Na$_2$SO$_4$, filtered & concentrated) to yield (1-3); [M+H]+m/z: observed=395.3; calculated=395.5.

Preparation of (S)-tert-butyl (1-amino-3-phenylpropan-2-yl)(methyl)carbamate (1-4)

To a flask containing (S)-tert-butyl (1-(1,3-dioxoisoindolin-2-yl)-3-phenylpropan-2-yl)(methyl)carbamate (1-3)

(740 mg, 1.876 mmol) was added MeOH (10 mL) followed by water (5 mL), and hydrazine hydrate (1 mL, 20.56 mmol). This reaction mixture was heated to reflux (95° C., under atmosphere). The reaction progress was followed by LC/MS. After 2 hrs the reaction mixture was cooled to room temperature, then partially concentrated and the residue suspended in EtOAc. The resulting mixture was washed with saturated NaHCO$_3$, then H$_2$O, then brine; and dried over Na$_2$SO$_4$. Thus obtained, the organics were filtered and concentrated to yield (1-4); [M+H]+m/z: observed=265.4; calculated=265.3.

Preparation of (S)-tert-butyl (1-((2-chloro-4-(N-(2, 4-dimethoxybenzyl)-N-(thiazol-2-yl)sulfamoyl)-5-fluorophenyl)amino)-3-phenylpropan-2-yl)(methyl)carbamate (1-6)

To a microwave vial containing (S)-tert-butyl (1-amino-3-phenylpropan-2-yl)(methyl)carbamate (1-4) (480 mg, 1.816 mmol) in anhydrous NMP (10 mL) was added 5-chloro-N-(2,4-dimethoxybenzyl)-2,4-difluoro-N-(thiazol-2-yl)benzenesulfonamide (1-5) (882 mg, 1.914 mmol) followed by DIPEA (0.8 mL, 4.58 mmol). The reaction mixture was then capped and heated at 100° C. in the microwave for 20 minutes. The reaction was followed by LC/MS. The reaction mixture was then diluted with MeCN/drops of H$_2$O/DMSO, then was purified (without workup) by reverse phase chromatography (2 injections) (25-100% MeCN/H2O; 0.1% TFA in AQ; 20 min gradient; Waters 30×150 mm Sunfire 5 micron C18 column; Flow=40 mL/min); desired fractions concentrate under reduced pressure. The resulting residue was then dissolved in MeOH/DCM and concentrated to yield (1-6); [M+H]+m/z=observed=705.3, 707.3; calculated=706.2. This material used as is in the deprotection step.

Preparation of (S)-5-chloro-2-fluoro-4-((2-(methylamino)-3-phenylpropyl)amino)-N-(thiazol-2-yl)benzenesulfonamide (1-7)

To a flask containing (S)-tert-butyl (1-((2-chloro-4-(N-(2, 4-dimethoxybenzyl)-N-(thiazol-2-yl)sulfamoyl)-5-fluorophenyl)amino)-3-phenylpropan-2-yl)(methyl)carbamate (1-6) (986 mg, 1.398 mmol) in DCM (5 mL) was added TFA (1 mL, 12.98 mmol). The reaction mixture was then stirred at room temperature (open to the atmosphere). The reaction was followed by LC/MS. After approximately 3 hours the reaction mixture was then diluted/quenched with DMSO, then MeOH, then filtered through a celite filter. The filtrate was concentrated (to remove DCM), then diluted with MeOH/DMSO & purified (without workup) by reverse phase chromatography (2 injections) (5-50% MeCN/H2O; 0.1% TFA in AQ; 15 min gradient; Waters 30×150 mm Sunfire 5 micron C18 column; Flow=40 mL/min); desired fractions concentrated under reduced pressure.

The resulting residue was then dissolved in MeOH/DCM and concentrated to yield (1-7); [M+H]+ m/z=observed=455.2; calculated=455.9. $^1$H NMR (400 MHz, CD3OD): δ 2.80 (s, 3H); 2.93-2.87 (m, 1H); 3.22-3.17 (m, 1H); 3.55-3.39 (m, 2H); 3.74-3.67 (m, 1H); 6.09 (d, J=12.3 Hz, 1H); 6.73 (d, J=4.7 Hz, 1H); 7.11 (d, J=4.7 Hz, 1H); 7.40-7.31 (m, 5H); 7.71 (d, J=7.1 Hz, 1H).

Example 1B (S)-5-chloro-2-fluoro-4-((3-(4-fluorophenyl)-2-(methylamino)propyl)amino)-N-(thiazol-2-yl)benzenesulfonamide (1-12, Method B)

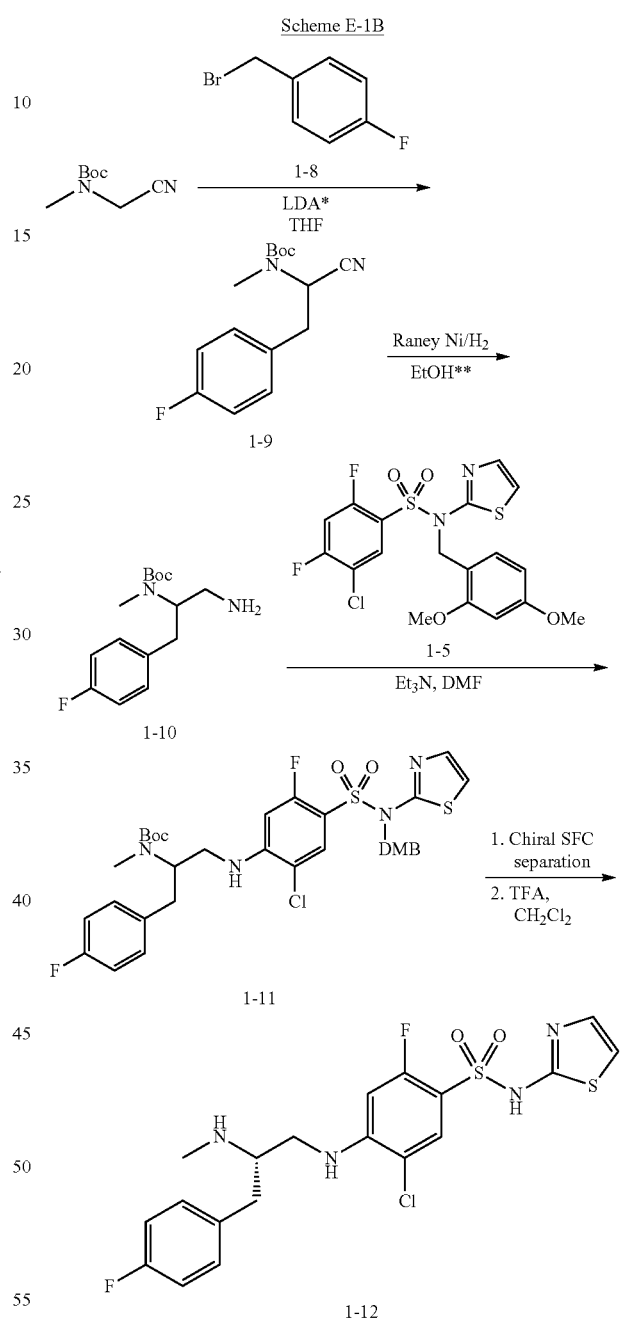

*LiHMDS can also be utilized for this alkylation
**NOTE: This reduction can also be performed with BH$_3$•DMS in THF.

Preparation of tert-butyl (1-cyano-2-(4-fluorophenyl)ethyl)(methyl)carbamate 1-9

A mixture of tert-butyl (cyanomethyl)(methyl)carbamate (500 mg, 2.94 mmol) in THF (3 mL) was stirred at −78° C. under N$_2$. LDA (2.203 ml, 4.41 mmol) and DMPU (1.417 ml, 11.75 mmol) were added dropwise at −78° C. The reaction mixture was stirred at this temperature for 1 h. 1-8 (833 mg, 4.41 mmol) was added dropwise at −78° C. The mixture was stirred at −78° C. for 1 h. The mixture was diluted with EtOAc (100 mL), washed with aq. NH$_4$Cl (100 mL), dried over Na$_2$SO$_4$, filtered and the solvent was evaporated under reduced pressure. The residue was purified by prep-TLC (PE:EA=10:1) to give 1-9.

$^1$H NMR (CDCl$_3$, 400 MHz) δ 7.17~7.02 (m, 2H), 7.00~6.98 (m, 2H), 5.35~5.02 (m, 1H), 3.11~2.90 (m, 5H), 1.56~1.42 (m, 9H).

Preparation of tert-butyl (1-amino-3-(4-fluorophenyl)propan-2-yl)(methyl)carbamate (1-10)

A mixture of 1-9 (100 mg, 0.36 mmol) and Raney Ni containing NH$_3$.H$_2$O (0.5 mL) in EtOH (15 mL) was stirred under H$_2$ (15 psi) at 25° C. for 15 h. The reaction progress was followed by LCMS. After the reaction was completed, the solid was filtered and the filtrate was concentrated in vacuo to give 1-10 which was used in next step directly.

Preparation of tert-butyl (1-((2-chloro-4-(N-(2,4-dimethoxybenzyl)-N-(thiazol-2-yl)-sulfamoyl)-5-fluorophenyl)amino)-3-(4-fluorophenyl)propan-2-yl)(methyl)carbamate (1-11)

A mixture of 1-10 (80 mg, 0.28 mmol), 1-5 (142 mg, 0.33 mmol) and Et$_3$N (143 mg, 1.4 mmol) in DMF was stirred for 15 h at 50° C. under N$_2$. After completion of the reaction, the mixture was concentrated by vacuo to give a residue, which was purified by prep-TLC (PE:EA=1:1) to give the product of 1-11. The product was resolved by SFC (Column: Chiralpak AD-3 150×4.6 mm I.D., 3 um Mobile phase: isopropanol (0.05% DEA) in CO$_2$ from 5% to 40%; Flow rate: 2.5 mL/min; Wavelength: 280 nm, t$_1$=8.32, t$_2$=9.91) to give the enantiomer A and enantiomer B.

$^1$H NMR (CDCl$_3$, 400 MHz) δ 7.72 (br. s., 1H), 7.38 (d, J=3.6 Hz, 1H), 7.22~7.11 (m, 3H), 7.03~6.98 (m, 2H), 6.95 (d, J=3.6 Hz, 1H), 6.39~6.34 (m, 2H), 6.23 (d, J=12.4 Hz, 1H), 5.19 (s, 2H), 4.70~4.47 (m, 1H), 3.75 (s, 6H), 3.30~3.13 (m, 2H), 2.96~2.78 (m, 2H), 2.66 (s, 3H), 1.43~1.25 (m, 9H).

Preparation of (S)-5-chloro-2-fluoro-4-((3-(4-fluorophenyl)-2-(methylamino)propyl) amino)-N-(thiazol-2-yl)benzenesulfonamide (1-12)

A mixture of 1-11 (enantiomer A, 30 mg, 0.04 mmol) and TFA (1 mL) in DCM (4 mL) was stirred at 20° C. for 1 h. After the reaction was completed, the mixture was concentrated in vacuo to give the crude product which was purified by prep-HPLC to give the product 1-12A.

1-12A: $^1$H NMR (CD$_3$OD, 400 MHz) δ 7.69 (d, J=7.2 Hz, 1H), 7.37~7.33 (m, 2H), 7.12~7.07 (m, 3H), 6.73 (d, J=4.8 Hz, 1H), 6.10 (d, J=12.4 Hz, 1H), 3.68 (dd, J=4.2, 8.4 Hz, 1H), 3.57~3.51 (m, 1H), 3.44~3.39 (m, 1H), 3.18 (dd, J=4.8, 14.0 Hz, 1H), 2.92~2.86 (m, 1H), 2.79 (s, 3H). LRMS m/z (M+H) 473.0 found, 473.1 required.

1-12B: $^1$H NMR (CD$_3$OD, 400 MHz) δ 7.72 (br. s., 1H), 7.40~7.35 (m, 2H), 7.13 (d, J=4.8 Hz, 3H), 6.75 (d, J=4.4 Hz, 1H), 6.13 (br. s., 1H), 3.70 (br. s., 1H), 3.59~3.53 (m, 1H), 3.46~3.40 (m, 1H), 3.23~3.15 (m, 1H), 2.92 (dd, J=9.6, 14.0 Hz, 1H), 2.81 (s, 3H). LRMS m/z (M+H) 473.0 found, 473.1 required.

Example 1C (S)-5-chloro-4-((3-cyclohexyl-2-(methylamino)propyl)amino)-2-fluoro-N-(thiazol-2-yl)benzenesulfonamide (1-18, Method C)

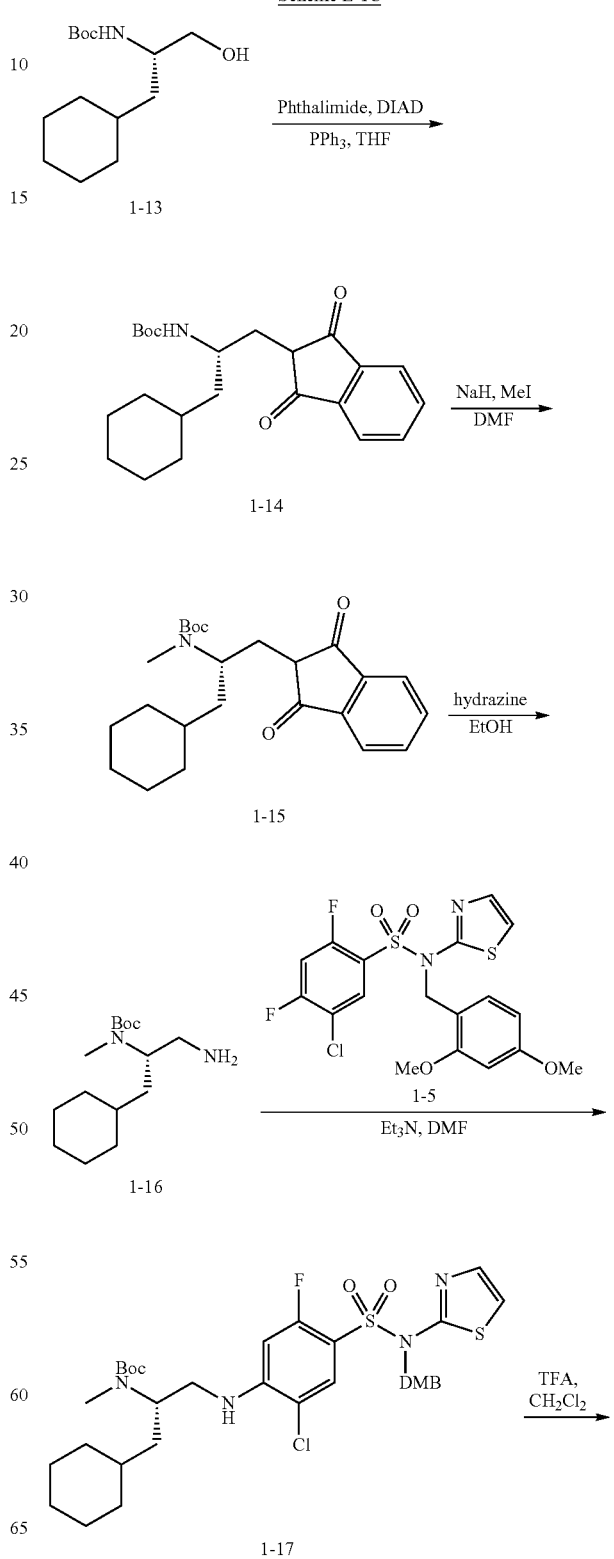

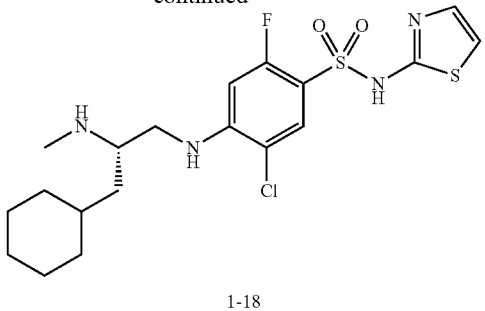

1-18

Preparation of (S)-tert-butyl (1-cyclohexyl-3-(1,3-dioxoisoindolin-2-yl)propan-2-yl)carbamate (1-14)

To a solution of 1-13 (2.4 g, 9.33 mmol), Ph₃P (4.89 g, 18.65 mmol) and isoindoline-1,3-dione (2.74 g, 18.65 mmol) in THF (30 mL) was added DIAD (3.63 mL, 18.65 mmol) at 0° C. Then the reaction was stirred at 20° C. for 14 h. Completion of the reaction was detected by TLC (PE:EA=3:1). After completion of the reaction, the mixture was quenched by H₂O (50 mL), extracted by 3 aliquots of EtOAc (30 mL). The organic was washed with two aliquots of 15% NaOH (30 mL) and brine (50 mL), dried over Na₂SO₄. The product was filtered and concentrated in vacuo. The residue was purified by column chromatography on silica gel (PE:EA=5:1) to give 1-14.

¹H NMR (CDCl₃, 400 MHz) δ 7.82 (s, 2H), 7.68 (s, 2H), 4.57-4.46 (m, 1H), 3.81-3.71 (m, 2H), 3.66 (d, J=9.8 Hz, 1H), 3.54-3.44 (m, 1H), 1.84-1.76 (m, 5H), 1.73-1.61 (m, 4H), 1.45 (s, 9H), 1.22-0.80 (m, 2H)

Preparation of (S)-tert-butyl (1-cyclohexyl-3-(1,3-dioxoisoindolin-2-yl)propan-2-yl)(methyl)carbamate (1-15)

To a solution of 1-14 (1 g, 2.59 mmol) in THF (20 mL) was added NaH (0.207 g, 5.17 mmol) at 0° C. The reaction mixture was stirred at 0° C. for 1 h. Then to the reaction mixture was added MeI (0.647 mL, 10.35 mmol). The reaction mixture was stirred at 20° C. for 12 h. The reaction progress was followed by TLC (PE:EA=3:1). After completion of reaction, the mixture was quenched by H₂O (50 mL), extracted by 3 aliquots of EtOAc (30 ml). The organic phase was washed with brine (50 mL), dried over Na₂SO₄. The mixture was filtered and the filtrate was concentrated in vacuo. The residue was purified by column chromatography on silica gel (PE:EA=5:1) to give 1-15 as a powder.

¹H NMR (CDCl₃, 400 MHz) δ 7.87-7.77 (m, 2H), 7.74-7.62 (m, 2H), 4.73-4.52 (m, 1H), 3.83-3.66 (m, 1H), 3.53-3.39 (m, 1H), 2.76-2.67 (m, 3H), 1.86-1.76 (m, 2H), 1.75-1.61 (m, 5H), 1.58 (s, 9H), 1.44 (br. s., 1H), 1.35-1.18 (m, 5H).

Preparation of (S)-tert-butyl (1-amino-3-cyclohexyl-propan-2-yl)(methyl)carbamate (1-16)

To a solution of 1-15 (250 mg, 0.647 mmol) in EtOH (5 mL) was added N₂H₄·H₂O (1 mL, 0.647 mmol). Then the reaction was stirred at 80° C. for 1 h. The reaction progress was followed using TLC (PE:EA=3:1). Upon completion of the reaction the mixture was filtered and concentrated in vacuo to give 1-16.

¹H NMR (CDCl₃, 400 MHz) δ 3.14-2.98 (m, 1H), 2.77-2.51 (m, 5H), 1.95-1.84 (m, 1H), 1.75-1.55 (m, 4H), 1.46 (s, 9H), 1.27-1.09 (m, 6H), 1.01-0.72 (m, 2H)

Preparation of (S)-tert-butyl (1-((2-chloro-4-(N-(2,4-dimethoxybenzyl)-N-(thiazol-2-yl)sulfamoyl)-5-fluorophenyl)amino)-3-cyclohexlpropan-2-yl)(methyl)carbamate (1-17)

To a solution of 1-16 (150 mg, 0.555 mmol) and 1-5 (307 mg, 0.666 mmol) in DMF (5 mL) was added Et₃N (0.387 mL, 2.77 mmol). The mixture was stirred at 20° C. for 14 h. Completion of the reaction was determined by TLC (PE:EA=3:1). Upon completion the reaction was quenched with water (20 mL), extracted with 3 aliquots of EtOAc (20 mL), washed with brine (50 mL), dried over Na₂SO₄, filtered and concentrated in vacuo. The residue was purified by column chromatography on silica gel (PE:EA=4:1) to give 1-17.

¹H NMR (CDCl₃, 400 MHz) δ 7.78-7.66 (m, 1H), 7.41-7.34 (m, 1H), 7.23-7.15 (m, 1H), 6.98-6.90 (m, 1H), 6.36 (s, 2H), 6.29-6.19 (m, 1H), 5.19 (s, 2H), 3.75 (s, 6H), 3.13-2.97 (m, 2H), 2.68 (d, J=11.7 Hz, 3H), 1.85-1.78 (m, 5H), 1.69 (m, 5H), 1.47-1.39 (s, 9H), 1.28-1.14 (m, 4H). LRMS m/z (M+H) 711.2 found, 711.2 required.

Preparation of (S)-5-chloro-4-((3-cyclohexyl-2-(methylamino)propyl)amino)-2-fluoro-N-(thiazol-2-yl)benzenesulfonamide (1-18)

To a solution of 1-17 (100 mg, 0.141 mmol) in DCM (4 mL) was added TFA (1 mL). The mixture was stirred at 20° C. for 1 h. Then the reaction was detected by LCMS. The reaction mixture was concentrated in vacuo and the residue was purified by prep-HPLC (TFA) to give 1-18.

¹H NMR (CD₃OD, 400 MHz) δ 7.76-7.68 (m, 1H), 7.14-7.07 (m, 1H), 6.73 (s, 1H), 6.62 (d, J=12.5 Hz, 1H), 3.51 (br. s., 3H), 2.70 (s, 3H), 1.81-1.68 (m, 5H), 1.61-1.50 (m, 2H), 1.50-1.36 (m, 1H), 1.32-1.10 (m, 3H), 0.95 (d, J=11.7 Hz, 2H). LRMS m/z (M+H) 461.1 found, 461.1 required.

The compounds in TABLE 1 were prepared using the methodology described in synthesis method A herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE 1

| Example | Structure | Name | Data |
|---------|-----------|------|------|
| EX 1-26 | 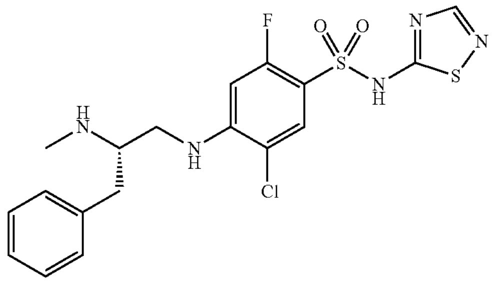 [SMILES: CN[C@H](CNc1cc(F)c(S(=O)(=O)Nc2ncns2)cc1Cl)Cc1ccccc1] | (S)-5-chloro-2-fluoro-4-((2-(methylamino)-3-phenylpropyl)amino)-N-(1,2,4-thiadiazol-5-yl)-benzenesulfonamide | LRMS m/z (M + H) 456.3 found, 456.1 required. |
| EX 1-27 | 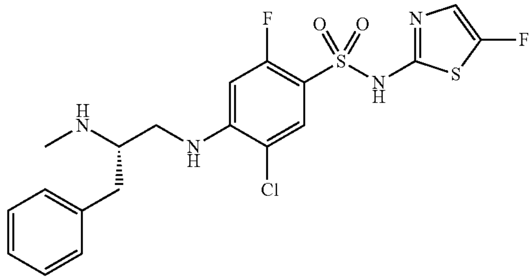 [SMILES: CN[C@H](CNc1cc(F)c(S(=O)(=O)Nc2ncc(F)s2)cc1Cl)Cc1ccccc1] | (S)-5-chloro-2-fluoro-N-(5-fluorothiazol-2-yl)-4-((2-(methylamino)-3-phenylpropyl)amino)-benzenesulfonamide | LRMS m/z (M + H) 473.0 found, 473.1 required. |

The following compounds were prepared using the methodology described in synthesis method B herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE 1A

| Example | Structure | Name | Data |
|---------|-----------|------|------|
| EX 1-19 | 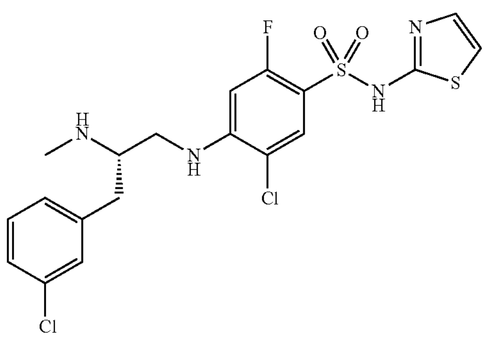 [SMILES: CN[C@H](CNc1cc(F)c(S(=O)(=O)Nc2nccs2)cc1Cl)Cc1cccc(Cl)c1] | (S)-5-chloro-4-((3-(3-chlorophenyl)-2-(methylamino)propyl)-amino)-2-fluoro-N-(thiazol-2-yl)-benzenesulfonamide | LRMS m/z (M + H) 489.0 found, 489.0 required. |
| EX 1-20 | 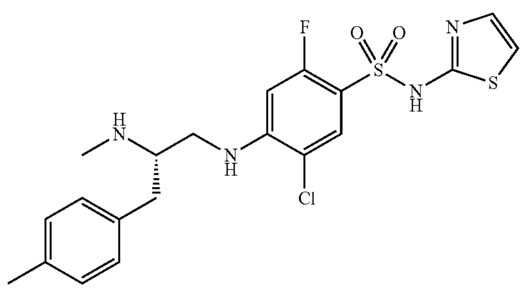 [SMILES: CN[C@H](CNc1cc(F)c(S(=O)(=O)Nc2nccs2)cc1Cl)Cc1ccc(C)cc1] | (S)-5-chloro-2-fluoro-4-((2-(methylamino)-3-(p-tolyl)propyl)amino)-N-(thiazol-2-yl)-benzenesulfonamide | LRMS m/z (M + H) 469.1 found, 469.1 required. |

TABLE 1A-continued

| Example | Structure | Name | Data |
|---|---|---|---|
| EX 1-21 | 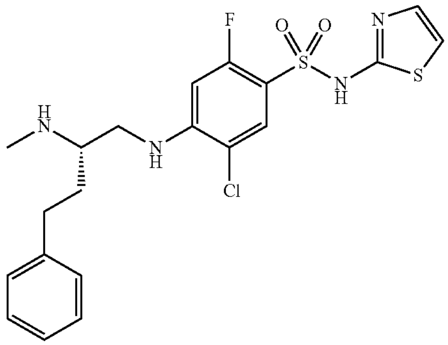 [SMILES: CN[C@@H](CCc1ccccc1)CNc1cc(F)c(S(=O)(=O)Nc2nccs2)cc1Cl] | (S)-5-chloro-2-fluoro-4-((2-(methylamino)-4-phenylbutyl)amino)-N-(thiazol-2-yl)-benzenesulfonamide | LRMS m/z (M + H) 469.1 found, 469.1 required. |
| EX 1-22 | 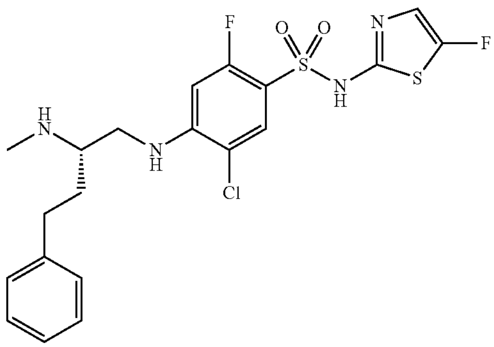 [SMILES: CN[C@@H](CCc1ccccc1)CNc1cc(F)c(S(=O)(=O)Nc2ncc(F)s2)cc1Cl] | (S)-5-chloro-2-fluoro-N-(5-fluorothiazol-2-yl)-4-((2-(methylamino)-4-phenylbutyl)amino)-benzenesulfonamide | LRMS m/z (M + H) 487.0 found, 487.1 required. |
| EX 1-23 | 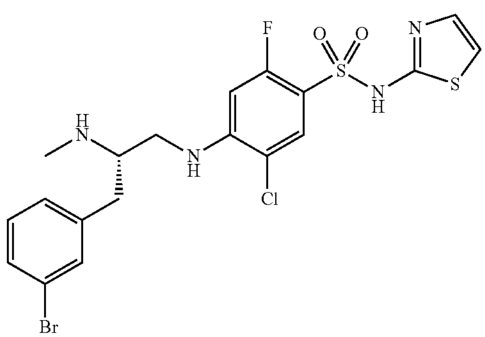 [SMILES: CN[C@H](CNc1cc(F)c(S(=O)(=O)Nc2nccs2)cc1Cl)Cc1cccc(Br)c1] | (S)-4-((3-(3-bromo-phenyl)-2-(methylamino)-propyl)amino)-5-chloro-2-fluoro-N-(thiazol-2-yl)-benzenesulfonamide | LRMS m/z (M + H) 535.0 found, 535.0 required. |
| EX 1-24 | 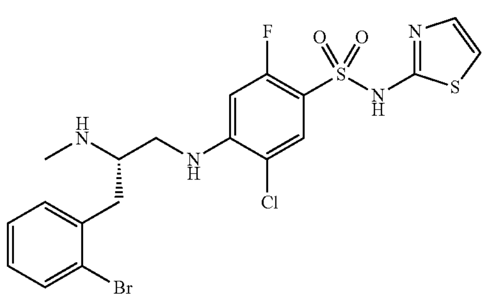 [SMILES: CN[C@H](CNc1cc(F)c(S(=O)(=O)Nc2nccs2)cc1Cl)Cc1ccccc1Br] | (S)-4-((3-(2-bromo-phenyl)-2-(methylamino)-propyl)amino)-5-chloro-2-fluoro-N-(thiazol-2-yl)-benzenesulfonamide | LRMS m/z (M + H) 535.0 found, 535.0 required. |

TABLE 1A-continued

| Example | Structure | Name | Data |
|---|---|---|---|
| EX 1-25 | 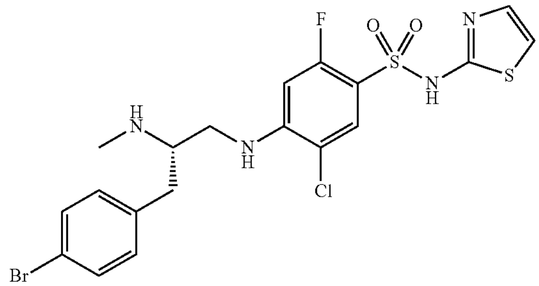 | (S)-4-((3-(4-bromo-phenyl)-2-(methylamino)-propyl)amino)-5-chloro-2-fluoro-N-(thiazol-2-yl)-benzenesulfonamide | LRMS m/z (M + H) 535.0 found, 535.0 required. |
| EX 1-28 | 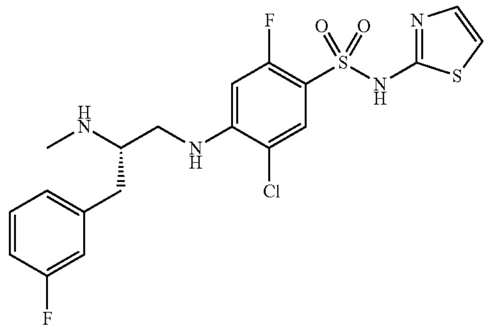 [SMILES: CN[C@H](CNc1cc(F)c(S(=O)(=O)Nc2nccs2)cc1Cl)Cc1cccc(F)c1] | (S)-5-chloro-2-fluoro-4-((3-(3-fluorophenyl)-2-(methylamino)-propyl)-amino)-N-(thiazol-2-yl)-benzenesulfonamide | LRMS m/z (M + H) 473.0 found, 473.1 required. |
| EX 1-29 | 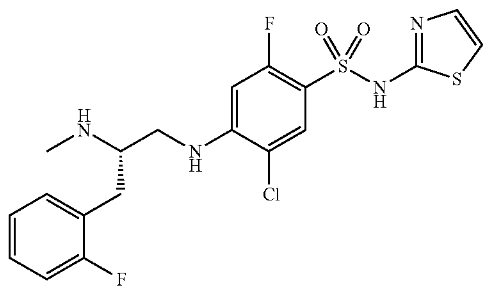 [SMILES: CN[C@H](CNc1cc(F)c(S(=O)(=O)Nc2nccs2)cc1Cl)Cc1ccccc1F] | (S)-5-chloro-2-fluoro-4-((3-(2-fluorophenyl)-2-(methylamino)-propyl)-amino)-N-(thiazol-2-yl)-benzenesulfonamide | LRMS m/z (M + H) 473.0 found, 473.1 required. |
| EX 1-30 | 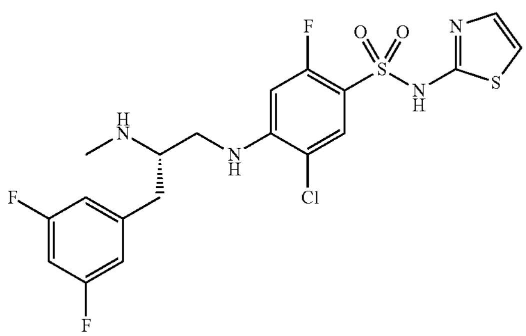 [SMILES: CN[C@H](CNc1cc(F)c(S(=O)(=O)Nc2nccs2)cc1Cl)Cc1cc(F)cc(F)c1] | (S)-5-chloro-4-((3-(3,5-difluorophenyl)-2-(methyl-amino)-propyl)amino)-2-fluoro-N-(thiazol-2-yl)-benzenesulfonamide | LRMS m/z (M + H) 490.9 found, 491.1 required. |
| EX 1-31 | 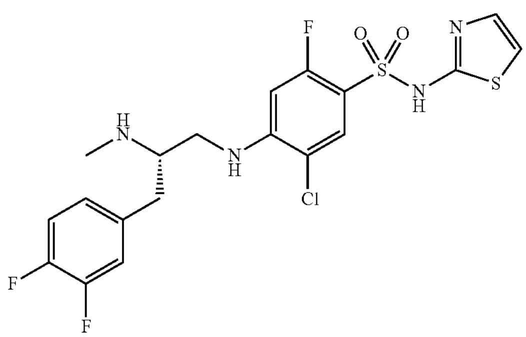 [SMILES: CN[C@H](CNc1cc(F)c(S(=O)(=O)Nc2nccs2)cc1Cl)Cc1ccc(F)c(F)c1] | (S)-5-chloro-4-((3-(3,4-difluorophenyl)-2-(methyl-amino)propyl)amino)-2-fluoro-N-(thiazol-2-yl)-benzenesulfonamide | LRMS m/z (M + H) 491.1 found, 491.1 required. |

TABLE 1A-continued

| Example | Structure | Name | Data |
|---|---|---|---|
| EX 1-32 | 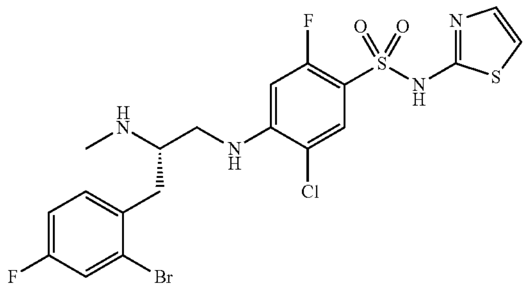 [SMILES: CN[C@H](CNc1cc(F)c(S(=O)(=O)Nc2nccs2)cc1Cl)Cc1ccc(F)cc1Br] | (S)-4-((3-(2-bromo-4-fluorophenyl)-2-(methyl-amino)propyl)-amino)-5-chloro-2-fluoro-N-(thiazol-2-yl)-benzenesulfonamide | LRMS m/z (M + H) 553.0 found, 553.0 required. |
| EX 1-33 | 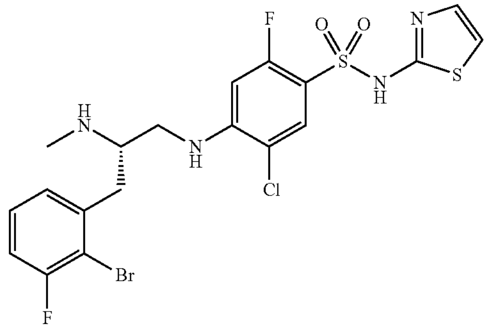 [SMILES: CN[C@H](CNc1cc(F)c(S(=O)(=O)Nc2nccs2)cc1Cl)Cc1cccc(F)c1Br] | (S)-4-((3-(2-bromo-3-fluorophenyl)-2-(methyl-amino)propyl)-amino)-5-chloro-2-fluoro-N-(thiazol-2-yl)-benzenesulfonamide | LRMS m/z (M + H) 552.9 found, 553.0 required. |
| EX 1-34 | 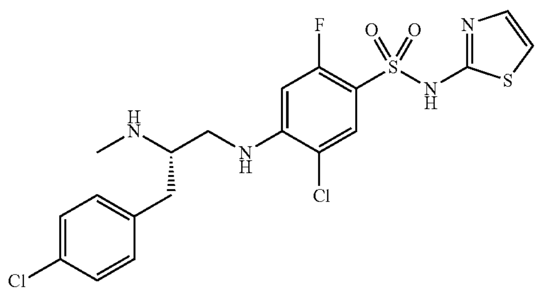 [SMILES: CN[C@H](CNc1cc(F)c(S(=O)(=O)Nc2nccs2)cc1Cl)Cc1ccc(Cl)cc1] | (S)-5-chloro-4-((3-(4-chlorophenyl)-2-(methyl-amino)propyl)amino)-2-fluoro-N-(thiazol-2-yl)-benzenesulfonamide | LRMS m/z (M + H) 489.0 found, 489.0 required. |

Example 2 (S)-5-chloro-4-((4,4-dimethyl-2-(methyl-amino)pentyl)amino)-2-fluoro-N-(5-fluorothiazol-2-yl)benzenesulfonamide (2-11)

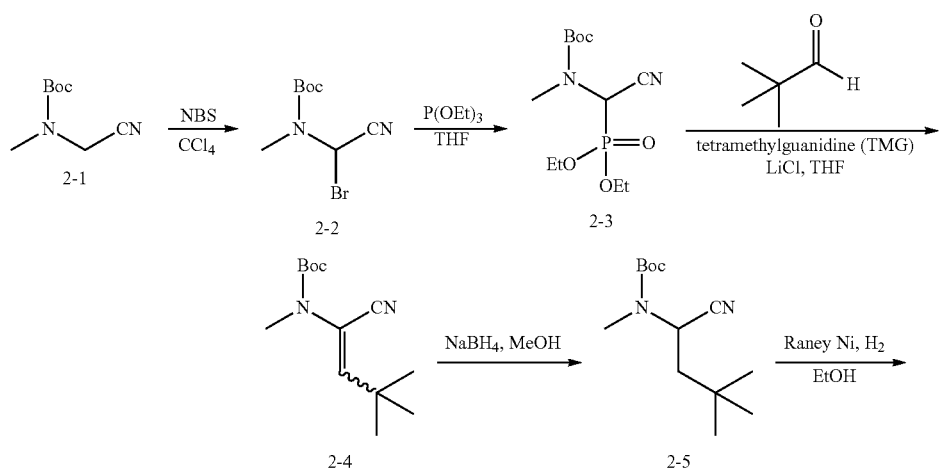

Scheme 2

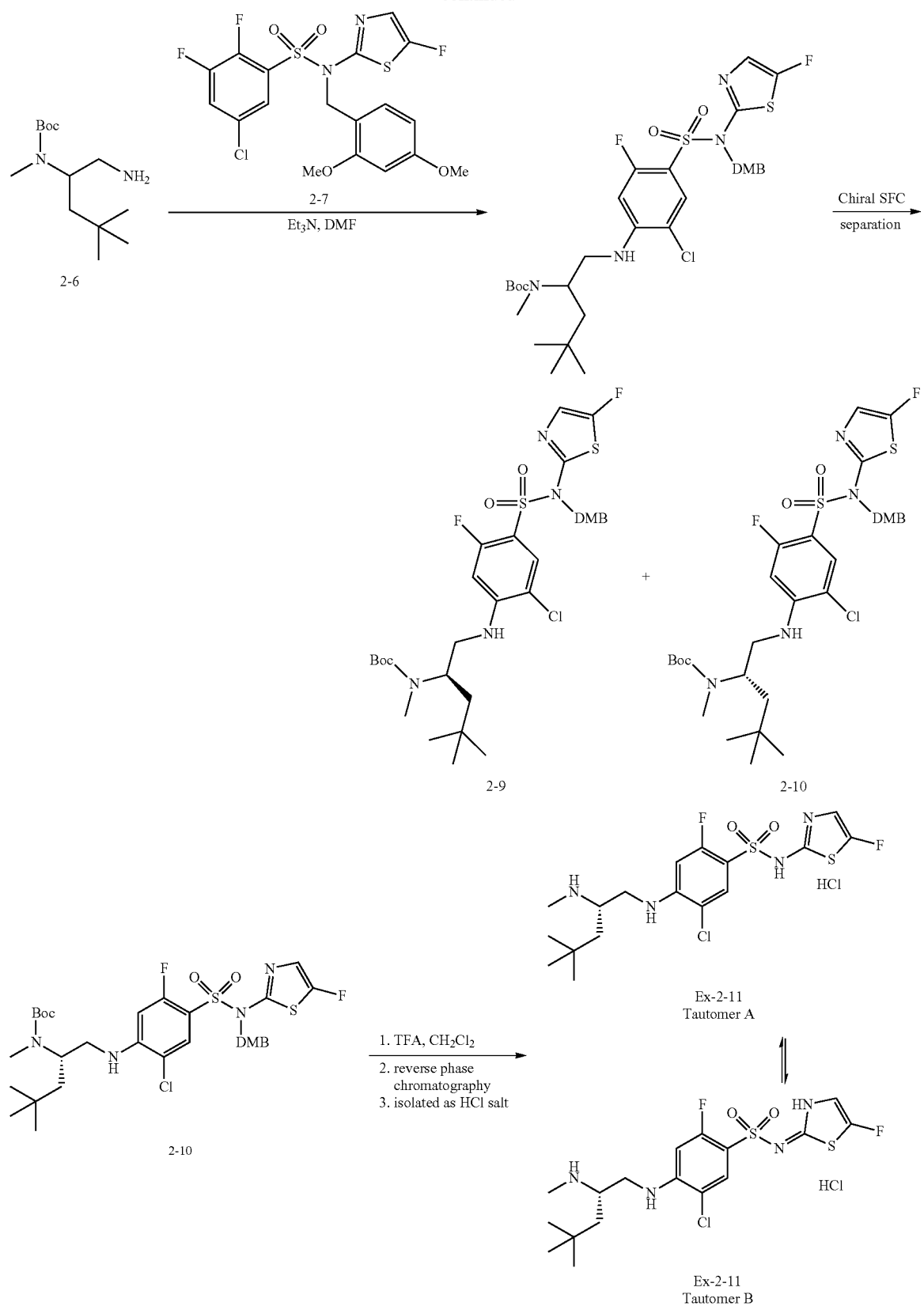

Preparation of tert-butyl (bromo(cyano)methyl)(methyl)carbamate (2-2)

To a solution of 2-1 (1 g, 5.88 mmol) in CCl$_4$ (15 mL) was added NBS (1.150 g, 6.46 mmol). The mixture was refluxed at 80° C. for 2 h, at which time TLC analysis indicated the reaction was complete (PE:EA=5:1). Then the reaction was cooled down to 0° C. and stirred for 0.5 h, then filtered and concentrated in vacuo to give 2-2 as a yellow oil which was used in next step that without further purification.

Preparation of tert-butyl (cyano(diethoxyphosphoryl)methyl)(methyl)carbamate (2-3)

To a solution of 2-2 (1 g, 4.01 mmol) in THF (15 mL) was added triethyl phosphite (0.734 g, 4.42 mmol). The mixture was stirred at 75° C. under N$_2$ for 16 h, at which time TLC analysis indicated the reaction was complete (PE:EA=2:1). Then the reaction was filtered and concentrated in vacuo. The residue was purified by silica gel chromatography (SiO$_2$, PE:EA=5:1) to give 2-3 as a colorless oil.

$^1$H NMR (CDCl$_3$, 400 MHz) δ 4.53-4.34 (m, 1H), 4.26 (d, J=7.5 Hz, 4H), 3.08 (s, 3H), 1.48 (s, 9H), 1.41-1.32 (m, 6H)

Preparation of tert-butyl (1-cyano-3,3-dimethylbut-1-en-1-yl)(methyl)carbamate (2-4)

To a mixture of 2-3 (50 g, 163 mmol), LiCl (3.46 g, 82 mmol) and TMG (37.6 g, 326 mmol) in THF (500 mL) was added pivalaldehyde (28.1 g, 326 mmol) in THF (100 mL) at −78° C. The mixture was stirred for 2 h at −78° C. and then at 30° C. for 9 h, at which time TLC analysis indicated the reaction was complete (PE:EA=3:1). The reaction mixture was quenched with water (100 mL), extracted with EtOAc (200 mL*3), washed with brine (100 mL), dried over Na$_2$SO$_4$, filtered and concentrated in vacuo. The residue was purified by column chromatography on silica gel (SiO$_2$, PE:EA=15:1) to give the product 2-4 as a yellow oil.

$^1$H NMR (400 MHz, CDCl$_3$) δ 6.19 (s, 1H), 3.00 (s, 3H), 1.44 (s, 9H), 1.23 (s, 9H).

Preparation of tert-butyl (1-cyano-3,3-dimethylbutyl)(methyl)carbamate (2-5)

To a solution of 2-4 (25 g, 105 mmol) in MeOH (300 ml) was added NaBH$_4$ (15.87 g, 420 mmol). Then the mixture was stirred for 2 h. The reaction progress was followed by LCMS. When the starting material was consumed the mixture was concentrated in vacuo and dissolved in 20 ml DCM. The mixture was filtered and concentrated to give 2-5 as a yellow oil used in the next step without the further purification. LRMS m/z (M+H): 241.1 found, 241.1 required.

Preparation of tert-butyl (1-amino-4,4-dimethylpentan-2-yl)(methyl)carbamate (2-6)

To a solution of 2-5 (10 g, 41.6 mmol)) in EtOH (200 ml) was added Raney Ni (2.442 g, 41.6 mmol). Then the mixture was stirred under H$_2$ at 25° C. for 2 h. The reaction progress was followed by LCMS. When LCMS indicated the starting material was consumed the mixture was filtered and concentrated in vacuo to give 2-6 as a yellow oil. LRMS m/z (M+H): 245.2 found, 245.1 required.

Preparation of tert-butyl (1-((2-chloro-4-(N-(2,4-dimethoxybenzyl)-N-(5-fluorothiazol-2-yl)sulfamoyl)-5-fluorophenyl)amino)-4,4-dimethylpentan-2-yl)(methyl)carbamate (2-8)

To a mixture of 2-6 (7.96 g, 32.6 mmol) and 2-7 (13 g, 27.1 mmol) in DMF (300 ml) was added TEA (8.24 g, 81 mmol). Then the mixture was stirred at 25° C. for 16 h. The reaction progress was monitored by TLC. When TLC results indicated the starting material was consumed the mixture was quenched by H$_2$O (100 mL), and extracted by EtOAc (two aliquots of 200 mL). The organic layer was dried over Na$_2$SO$_4$, filtered and concentrated by vacuo to give a residue which was purified by column chromatography on silica gel (PE:EA=5:1) to give the product 2-8. Compound 2-8 was resolved under SFC condition below:

Column: Chiralpak AD-3 150×4.6 mm I.D., 3 um Mobile phase:iso-propanol (0.05% DEA) in CO$_2$ from 5% to 40%;

Flow rate: 2.4 mL/min; Wavelength: 220 nm"

Enantiomer 2-10 (P1) (peak 1: Rt=4.99 min, 99% ee) as a colourless oil and Enantiomer 2-9 (P2) (peak 2: Rt=5.42 min, 99% ee) as a colourless oil were obtained.

Preparation of (S)-5-chloro-4-((4,4-dimethyl-2-(methylamino)pentyl)amino)-2-fluoro-N-(5-fluorothiazol-2-yl)benzenesulfonamide (2-11)

To a solution of enantiomer 2-10 (P1) (5 g, 7.11 mmol) in 80 ml DCM was added TFA (10 ml). The mixture was stirred at 25° C. under N$_2$ for 1 h. The reaction progress was followed by LCMS. When LCMS indicated that the starting material had been consumed the mixture was concentrated and dissolved in 100 mL DMF and filtered. The filtrate was purified by prep-HPLC (HCl) to give 2-11 as a white solid. LRMS m/z (M+H): 453.1 found, 453.0 required.

Preparative HPLC was carried out on an instrument fitted with a Phenomenex Synergi Max-RP 250 mm column packed with 80A pore/10 um particle size and eluted at a flow rate of 120 ml/min. using as a mobile phase A: 0.05% HCl water; and Mobile phase B: acetonitrile as the eluents. A gradient was run according to the following schedule: (i) 19% to 39% B, 0-10.0 min; (ii) 100% B, 10.1-12.0 min; 10% B fixed, 12.1-15 min.

$^1$H NMR (400 MHz, CD$_3$OD) δ 7.74 (d, J=6.2 Hz, 1H), 7.00 (s, 1H), 6.70 (d, J=12.6 Hz, 1H), 3.60-3.43 (m, 3H), 2.73 (s, 3H), 1.64 (s, 2H), 1.02 (s, 9H).

The absolute configuration was determined from single crystal X-ray diffraction. The pure material prepared above was crystallized as the anhydrous HCl salt from methanol using slow solvent evaporation technique to provide crystals. Details of the equipment and conditions are given in the table below (R=4.4%):

| Details of X-ray Diffraction on Ex 2-11 single crystals | |
|---|---|
| Formula, Formula weight | (C$_{17}$ H$_{24}$ Cl F$_2$ N$_4$ O$_2$ S$_2$)$^+$·Cl$^-$, 489.42 |
| Crystal system, Space group | monoclinic, P2$_1$ |
| Cell lengths (Å) | a = 11.5999(2), b = 7.29640(10), c = 26.9054(5) |
| Cell angles (°) | α = 90.00, β = 101.8597(9), γ = 90.00 |
| V(Å$^3$), Z, Z', D$_{calc}$ (g/cm$^3$) | 2228.60(6), 4, 2, 1.459 |

| Details of X-ray Diffraction on Ex 2-11 single crystals | |
| --- | --- |
| μ(Cu Kα) (mm$^{-1}$) | 4.713 |
| F(000) | 1016 |
| Crystal size (mm) | 0.10 × 0.08 × 0.06 |
| Temperature (K) | 100 |
| Radiation (Å) | Cu Kα (1.54184) |
| Instrument | Bruker APEXII |
| Resolution (Å$^{-3}$), max theta (°) | 0.83, 68.25 |
| Reflections: (Total, Unique, 2σ Obsd) | 24085, 8100, 7436 |
| Refined parameters | 555 |
| R, wR$_2$, S | 0.044, 0.1007, 1.02723 |
| Absolute structure parameter (Flack) | −0.008(13) |
| Max. residual density [e Å$^{-3}$] | 0.356 |

The X-ray diffraction studies confirm the absolute configuration of the compound shown above, and that in the single crystal environment studied the tautomer structure shown for Ex-2-11, Tautomer B, above, is confirmed. As will be appreciated, the nomenclature associated with Ex2-11 indicates the structure shown above as Tautomer A, but it will be appreciated that in accordance with the definitions presented herein, the nomenclature contemplates the compound and all tautomers, including the equilibrium of both tautomers shown for Ex2-11, which can exist under the proper conditions.

The compounds in Table 2 were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE 2

| Exp. No | Structure | Name | Data |
| --- | --- | --- | --- |
| Ex 2-12 | 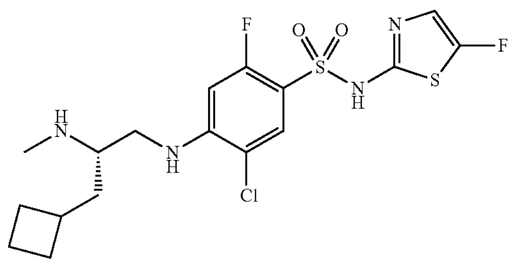 [SMILES: CN[C@H](CNc1cc(F)c(S(=O)(=O)Nc2ncc(F)s2)cc1Cl)CC1CCC1] | (S)-5-chloro-4-((3-cyclobutyl-2-(methylamino)propyl)amino)-2-fluoro-N-(5-fluorothiazol-2-yl)benzenesulfonamide | LRMS m/z (M + H) 451.0 found, 451.1 required. |
| Ex 2-13 | 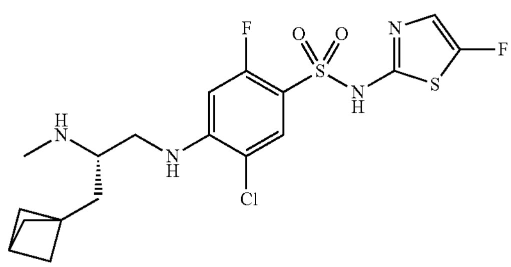 [SMILES: CN[C@H](CNc1cc(F)c(S(=O)(=O)Nc2ncc(F)s2)cc1Cl)CC12CC(C1)C2] | (S)-4-((3-(bicyclo[1.1.1]pentan-1-yl)-2-(methylamino)propyl)amino)-5-chloro-2-fluoro-N-(5-fluorothiazol-2-yl)-benzenesulfonamide | LRMS m/z (M + H) 463.1 found, 463.1 required. |
| Ex 2-14 | 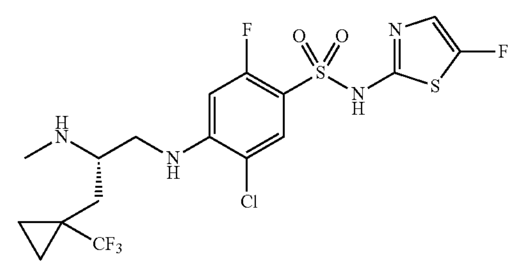 [SMILES: CN[C@H](CNc1cc(F)c(S(=O)(=O)Nc2ncc(F)s2)cc1Cl)CC1(C(F)(F)F)CC1] | (S)-5-chloro-2-fluoro-N-(5-fluorothiazol-2-yl)-4-((2-(methylamino)-3-(1-(trifluoromethyl)cyclopropyl)-propyl)amino) benzenesulfonamide | LRMS m/z (M + H) 505.0 found, 505.0 required. |

TABLE 2-continued

| Exp. No | Structure | Name | Data |
|---|---|---|---|
| Ex 2-15 | 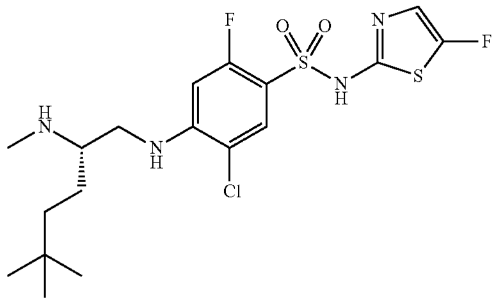 [SMILES: CN[C@@H](CCC(C)(C)C)CNc1cc(F)c(S(=O)(=O)Nc2ncc(F)s2)cc1Cl] | (S)-5-chloro-4-((5,5-dimethyl-2-(methylamino)hexyl)amino)-2-fluoro-N-(5-fluorothiazol-2-yl)-benzenesulfonamide | LRMS m/z (M + H) 467.1 found, 467.1 required. |
| Ex 2-16 | 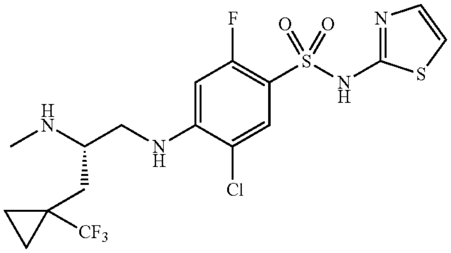 [SMILES: CN[C@H](CNc1cc(F)c(S(=O)(=O)Nc2nccs2)cc1Cl)CC1(C(F)(F)F)CC1] | (S)-5-chloro-2-fluoro-4-((2-(methylamino)-3-(1-(trifluoromethyl)cyclopropyl)-propyl)amino)-N-(thiazol-2-yl)-benzenesulfonamide | LRMS m/z (M + H) 487.0 found, 487.1 required. |
| Ex 2-17 | 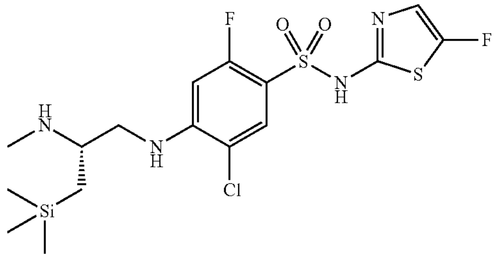 [SMILES: CN[C@H](CNc1cc(F)c(S(=O)(=O)Nc2ncc(F)s2)cc1Cl)C[Si](C)(C)C] | (R)-5-chloro-2-fluoro-N-(5-fluorothiazol-2-yl)-4-((2-(methylamino)-3-(trimethylsilyl)propyl)-amino)benzenesulfonamide | LRMS m/z (M + H) 469.0 found, 469.1 required. |
| Ex 2-18 | 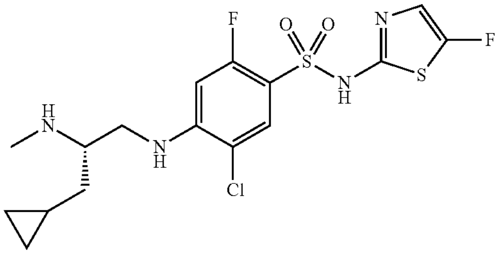 [SMILES: CN[C@H](CNc1cc(F)c(S(=O)(=O)Nc2ncc(F)s2)cc1Cl)CC1CC1] | (S)-5-chloro-4-((3-cyclopropyl-2-(methylamino)propyl)amino)-2-fluoro-N-(5-fluorothiazol-2-yl)-benzenesulfonamide | LRMS m/z (M + H) 437.0 found, 437.1 required. |
| Ex 2-19 | 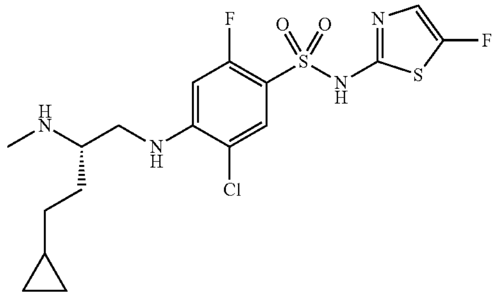 [SMILES: CN[C@@H](CCC1CC1)CNc1cc(F)c(S(=O)(=O)Nc2ncc(F)s2)cc1Cl] | (S)-5-chloro-4-((4-cyclopropyl-2-(methylamino)butyl)amino)-2-fluoro-N-(5-fluorothiazol-2-yl)-benzenesulfonamide | LRMS m/z (M + H) 451.0 found, 451.1 required. |

TABLE 2-continued

| Exp. No | Structure | Name | Data |
|---|---|---|---|
| Ex 2-20 | 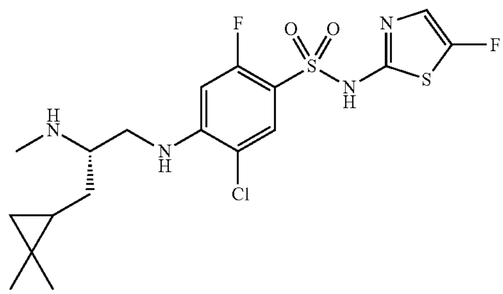 [SMILES: CN[C@H](CNc1cc(F)c(S(=O)(=O)Nc2ncc(F)s2)cc1Cl)CC1CC1(C)C] | 5-chloro-4-(((2S)-3-(2,2-dimethylcyclopropyl)-2-(methylamino)propyl)amino)-2-fluoro-N-(5-fluorothiazol-2-yl)-benzenesulfonamide | LRMS m/z (M + H) 465.0 found, 465.1 required. |
| Ex 2-21 | 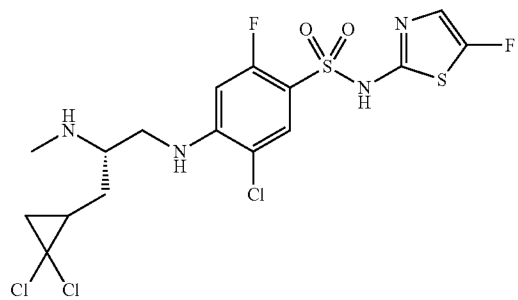 [SMILES: CN[C@H](CNc1cc(F)c(S(=O)(=O)Nc2ncc(F)s2)cc1Cl)CC1CC1(Cl)Cl] | 5-chloro-4-(((2S)-3-(2,2-dichlorocyclopropyl)-2-(methylamino)propyl)amino)-2-fluoro-N-(5-fluorothiazol-2-yl)-benzenesulfonamide | LRMS m/z (M + H) 505.0 found, 505.0 required. |
| Ex 2-22 | 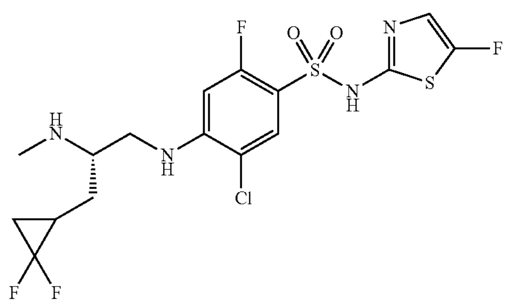 [SMILES: CN[C@H](CNc1cc(F)c(S(=O)(=O)Nc2ncc(F)s2)cc1Cl)CC1CC1(F)F] | 5-chloro-4-(((2S)-3-(2,2-difluorocyclopropyl)-2-(methylamino)propyl)amino)-2-fluoro-N-(5-fluorothiazol-2-yl)-benzenesulfonamide | LRMS m/z (M + H) 473.0 found, 473.0 required. |
| Ex 2-23 | 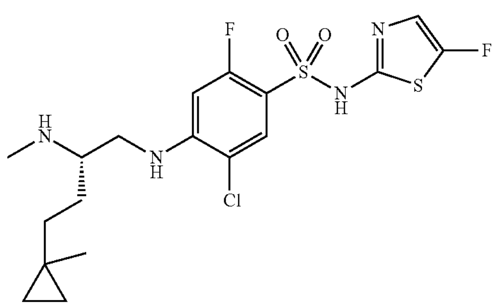 [SMILES: CN[C@@H](CCC1(C)CC1)CNc1cc(F)c(S(=O)(=O)Nc2ncc(F)s2)cc1Cl] | (S)-5-chloro-2-fluoro-N-(5-fluorothiazol-2-yl)-4-((2-(methylamino)-4-(1-methylcyclopropyl)butyl)amino)benzenesulfonamide | LRMS m/z (M + H) 464.9 found, 465.1 required. |

Example 3 (S)-5-chloro-4-((3-cyclopentyl-2-(methylamino)propyl)amino)-2-fluoro-N-(5-fluorothiazol-2-yl)benzenesulfonamide (3-11)
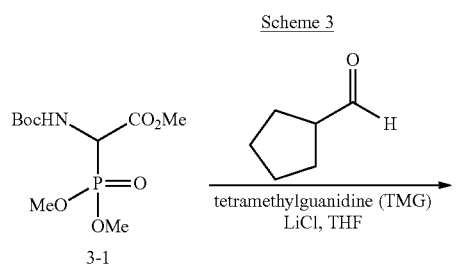
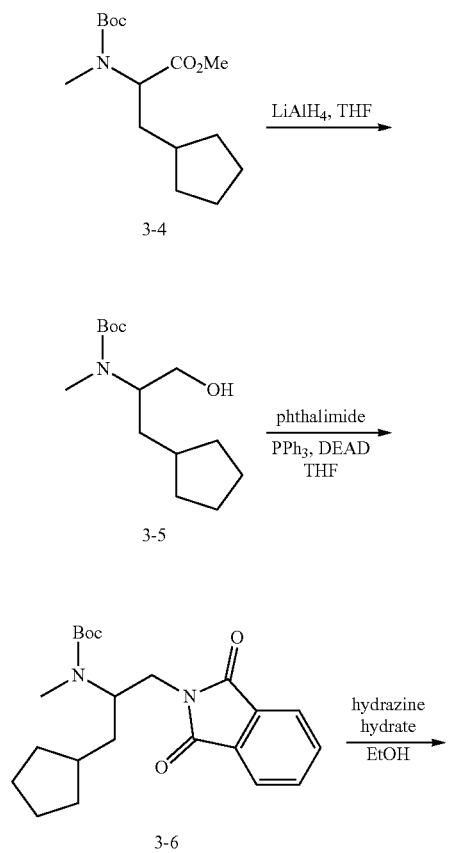
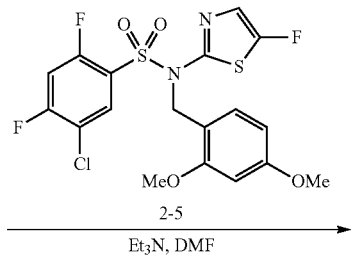
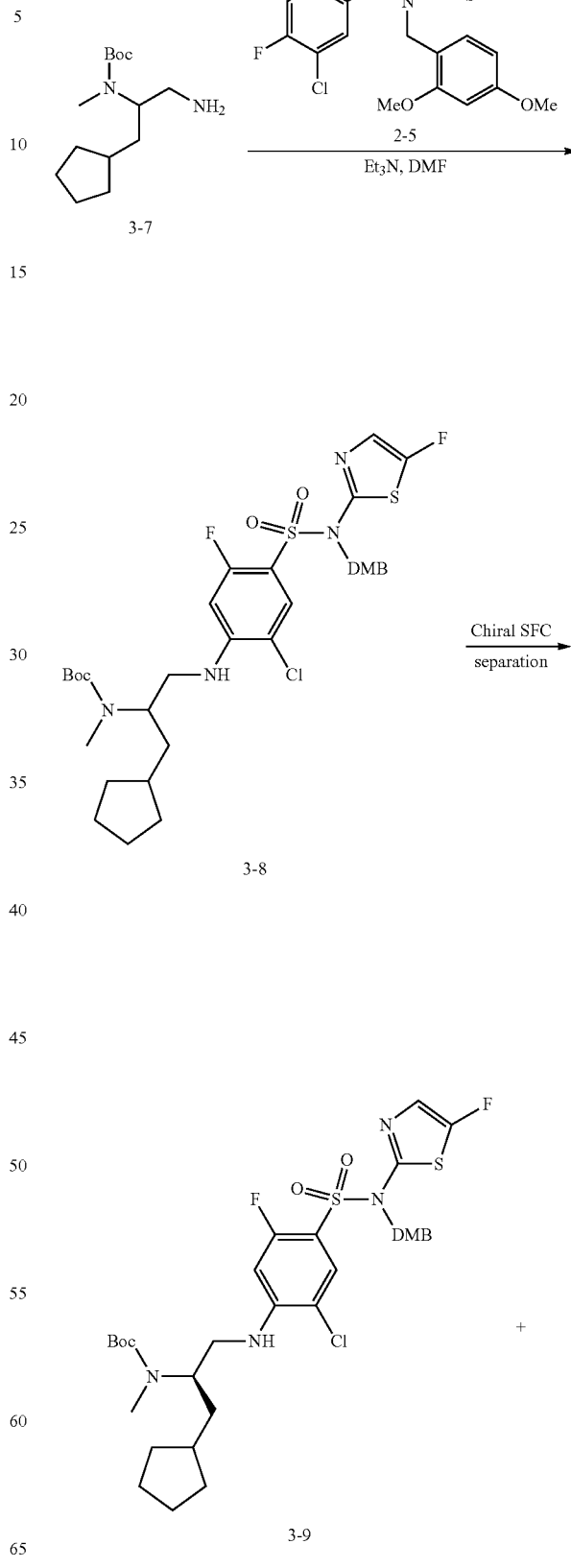

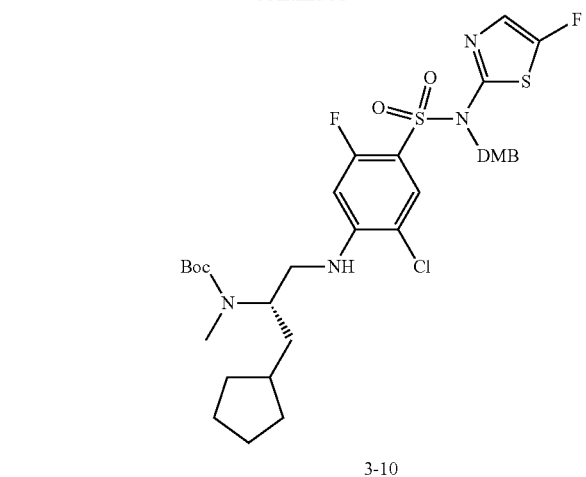

3-10

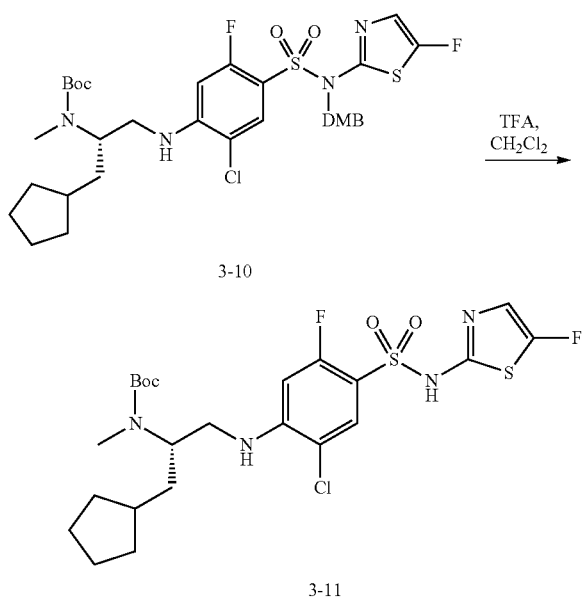

3-10

3-11

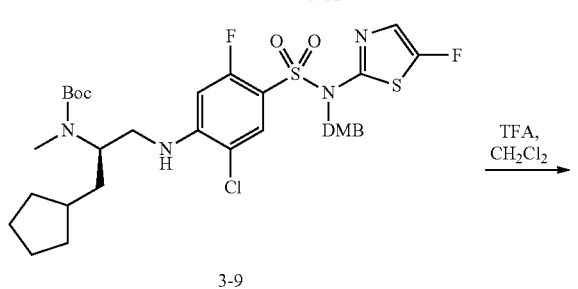

3-9

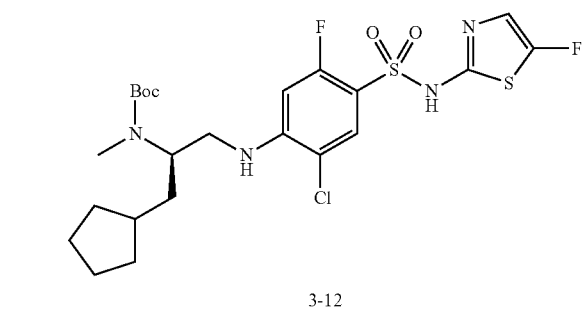

3-12

Preparation of methyl 2-((tert-butoxycarbonyl)amino)-3-cyclopentylacrylate (3-2)

Under a nitrogen atmosphere at −78° C., 1,1,3,3-tetramethylguanidine (7.75 g, 67.3 mmol) was added to a mixture of 3-1 (10 g, 33.6 mmol) and cyclopentanecarbaldehyde (33.0 g, 336 mmol) in THF (100 mL). The mixture was stirred for 4 h at −78° C. and then the mixture was warmed to 30° C. and stirred for 12 h. The progress of the reaction was monitored by TLC (petroleum ether:AcOEt=10:1) and LCMS (MS (ESI) m/z: 270.1 [M+H$^+$], $t_R$=1.02 min). Then the reaction mixture was quenched with H$_2$O (100 mL) and extracted with EtOAc (100 mL×3), dried (Na$_2$SO$_4$), filtered and concentrated. The crude material thus obtained was purified by column chromatography on silica gel (PE:EA=10:1) to give 3-2 as colorless oil.

$^1$H NMR (CDCl$_3$, 400 MHz) δ 6.50 (d, J 9.8 Hz, 1H), 5.87-5.64 (m, 1H), 3.76 (s, 3H), 2.86-2.72 (m, 1H), 1.93-1.84 (m, 2H), 1.68 (dd, J 10.4, 4.8 Hz, 6H), 1.51-1.43 (m, 9H).

Preparation of methyl 2-((tert-butoxycarbonyl)amino)-3-cyclopentylpropanoate (3-3)

A mixture of 3-2 (7 g, 23.39 mmol) and Pd/C (10% wt, 2.5 g, 2.339 mmol) in MeOH (50 mL) was stirred at 30° C. under H$_2$ (15 psi) for 12 h. The reaction was monitored by TLC and LCMS (MS (ESI) m/z: 272.1 [M+H$^+$], $T_R$=1.14 min). The mixture was filtered and concentrated to give crude material which was purified by column chromatography on silica gel (PE:EA=10:1) to give 3-3 as colorless oil.

$^1$H NMR (CDCl$_3$, 400 MHz) δ 4.94 (d, J 5.0 Hz, 1H), 4.29 (d, J 5.0 Hz, 1H), 3.73 (s, 3H), 1.91-1.75 (m, 4H), 1.70-1.59 (m, 5H), 1.45 (s, 9H), 1.19-1.05 (m, 2H).

Preparation of methyl 2-((tert-butoxycarbonyl)(methyl)amino)-3-cyclopentylpropanoate (3-4)

To a suspension of 3-3 (2 g, 7.37 mmol) and Ag$_2$O (8.54 g, 36.9 mmol) in DMF (20 mL) at 0° C. was added MeI (2.3 mL, 36.9 mmol) in several portions. The mixture was stirred for 12 h at 30° C., monitored by TLC and LCMS (MS (ESI) m/z: 286.3[M+H$^+$], $t_R$=1.38 min), then filtered and washed with EtOAc (200 mL). The organic phases were washed with 2 aliquots of water (50 mL each) then an aliquot of brine (50 mL), dried over Na$_2$SO$_4$, filtered and concentrated. The residue was purified by column chromatography on silica gel (PE:EA=10:1) to give 3-4 as colorless oil.

$^1$H NMR (CDCl$_3$, 400 MHz) δ 4.86-4.39 (m, 1H), 3.68 (d, J 2.4 Hz, 3H), 2.78 (d, J 15.2 Hz, 3H), 1.86-1.70 (m, 5H), 1.63-1.60 (m., 4H), 1.43 (d, J 8.6 Hz, 9H), 1.11 (br. s., 2H).

Preparation of tert-butyl (1-cyclopentyl-3-hydroxypropan-2-yl)(methyl)carbamate (3-5)

To a solution of LiAlH$_4$ (0.239 g, 6.31 mmol) in THF (20 mL) was added a solution of 3-4 (1.8 g, 6.31 mmol) in THF (20 mL) at 0° C. under N$_2$. Then the mixture was stirred at 30° C. for 2 h, monitored by TLC and LCMS (MS (ESI) m/z: 258.2[M+H$^+$], $t_R$=1.12 min), water (0.2 mL) was added to the mixture which was stirred for 10 min. MgSO$_4$ was added and the mixture was stirred for 30 min. The solid was removed by filtration and the solvent was removed by vacuo. The product of 3-5 (as a colorless oil) was obtained by column chromatography (SiO$_2$, PE:EtOAc=5:1).

$^1$H NMR (CDCl$_3$, 400 MHz) δ 3.54 (dd, J 10.4, 4.8 Hz, 1H), 3.21 (t, J 10.4 Hz, 1H), 2.71 (s, 1H), 2.69-2.55 (m, 1H), 2.23 (s, 3H), 2.00-1.60 (m., 9H), 1.60-1.39 (m, 9H), 1.43-1.03 (m, 2H).

Preparation of tert-butyl (1-cyclopentyl-3-(1,3-dioxoisoindolin-2-yl)propan-2-yl)(methyl)carbamate (3-6)

To a mixture of isoindoline-1,3-dione (0.926 g, 6.29 mmol), 3-5 (1.2 g, 4.20 mmol) and PPh$_3$ (1.651 g, 6.29 mmol) in THF (20 mL) was added dropwise DEAD (1 mL, 6.29 mmol) at 0° C. The mixture was stirred at 30° C. for 8 h. The reaction was monitored by TLC and LCMS (MS (ESI) m/z: 387.1 [M+H$^+$], t$_R$=1.27 min), then the mixture was quenched with water (50 mL) and extracted with EtOAc (3×50 mL). The combined organic phases were dried with Na$_2$SO$_4$ and concentrated. The residue was purified by column chromatography (SiO$_2$, PE:EtOAc=5:1) to give 3-6 as a white solid.

$^1$H NMR (CDCl$_3$, 400 MHz) δ 7.86-7.77 (m, 2H), 7.73-7.62 (m, 2H), 4.49 (br. s., 1H), 3.75 (d, J=15.6 Hz, 1H), 3.56-3.40 (m, 1H), 2.77-2.65 (m, 3H), 1.85-1.62 (m, 5H), 1.56 (s, 9H), 1.52-1.12 (m, 6H).

Preparation of tert-butyl (1-amino-3-cyclopentylpropan-2-yl)(methy)carbamate (3-7)

A mixture of 3-6 (350 mg, 0.906 mmol) and N$_2$H$_4$.H$_2$O (0.4 mL) in Ethanol (10 mL) was stirred at 80° C. under N$_2$ for 2 h. The reaction was monitored by TLC, the mixture was filtered and the filtrate was concentrated to give the product of 3-7 as a yellow oil which was used in the next step directly.

$^1$H NMR (CDCl$_3$, 400 MHz) δ 2.70-2.65 (m, 6H), 1.84-1.64 (m, 9H), 1.47 (s, 9H), 1.08 (br. s., 2H).

Preparation of 5-chloro-4-((3-cyclopentyl-2-(methylamino)propyl)amino)-N-(2,4-dimethoxybenzyl)-2-fluoro-N-(5-fluorothiazol-2-yl)benzenesulfonamide (3-8)

To a solution of 3-7 (60 mg, 234.02 umol) and 2-5 (112.07 mg, 234.02 umol) in DMF (5 mL) was added TEA (0.16 mL). The mixture was stirred at 26° C. for 12 h. The reaction progress was followed by TLC (PE:EA=5:1), and when complete the reaction was quenched with water (50 mL), extracted with EtOAc (50 mL*3), washed with brine (50 mL), dried over Na$_2$SO$_4$, filtered and concentrated in vacuo. The residue was purified by column chromatography (SiO$_2$, PE:EA=4:1) to give 3-8 (70.00 mg, 41.82% yield) as a white solid.

LRMS m/z (M+H): 715.2 found, 715.2 required.

Preparation of (R)-5-chloro-4-((3-cyclopentyl-2-(methylamino)propyl)amino)-N-(2,4-dimethoxybenzyl)-2-fluoro-N-(5-fluorothiazol-2-yl)benzenesulfonamide (3-9) and (S)-5-chloro-4-((3-cyclopentyl-2-(methylamino)propyl)amino)-N-(2,4-dimethoxybenzyl)-2-fluoro-N-(5-fluorothiazol-2-yl)benzenesulfonamide (3-10)

SFC conditions: Chiralpak AD-3 150×4.6 mm I.D., 3 um Mobile phase: ethanol (0.05% DEA) in CO$_2$ from 5% to 40%

Flow rate: 2.5 mL/min; Wavelength: 220 nm.

The 3-8 (70.00 mg) was resolved by SFC to give two enantiomers: 3-9 (peak 1) as a white solid, 3-10 (peak 2) as a white solid.

Preparation of (R)-5-chloro-4-((3-cyclopentyl-2-(methylamino)propyl)amino)-2-fluoro-N-(5-fluorothiazol-2-yl)benzenesulfonamide (3-12)

To a stirred solution of 3-9 (peak 1) (30 mg, 41.94 umol) in DCM (2 mL) was added TFA (0.5 mL), which was allowed to stirred for 1 h at 25° C. The reaction was followed by LCMS. When the reaction was complete the mixture was concentrated and purified by prep-HPLC (TFA) to give the product of 3-12 as white solid.

$^1$H NMR (CD$_3$OD, 400 MHz) δ 7.72 (d, J=7.4 Hz, 1H), 6.97 (s, 1H), 6.65 (d, J=12.4 Hz, 1H), 3.57-3.50 (m, 2H), 3.48-3.39 (m, 1H), 2.71 (s, 3H), 2.04-1.93 (m, 1H), 1.86 (d, J=5.4 Hz, 2H), 1.76-1.52 (m, 6H), 1.27-1.05 (m, 2H). LRMS m/z (M+H): 465.1 found, 465.1 required

Preparation of (S)-5-chloro-4-((3-cyclopentyl-2-(methylamino)propyl)amino)-2-fluoro-N-(5-fluorothiazol-2-yl)benzenesulfonamide (3-11)

The procedure of 3-11 was similar to that of 3-12.

$^1$H (CD$_3$OD, 400 MHz) δ 7.72 (d, J=7.4 Hz, 1H), 6.97 (s, 1H), 6.65 (d, J=12.4 Hz, 1H), 3.57-3.50 (m, 2H), 3.48-3.39 (m, 1H), 2.71 (s, 3H), 2.04-1.93 (m, 1H), 1.86 (d, J=5.4 Hz, 2H), 1.76-1.52 (m, 6H), 1.27-1.05 (m, 2H). LRMS m/z (M+H): 465.1 found, 465.1 required.

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE 3

| Exp No | Structure | Name | Data |
|---|---|---|---|
| Ex 3-13 | *(structure shown)* | (S)-5-chloro-4-((4-cyclobutyl-2-(methylamino)butyl)amino)-2-fluoro-N-(5-fluorothiazol-2-yl)-benzenesulfonamide | LRMS m/z (M + H) 465.1 found, 465.1 required |

TABLE 3-continued

| Exp No | Structure | Name | Data |
|---|---|---|---|
| Ex 3-14 | 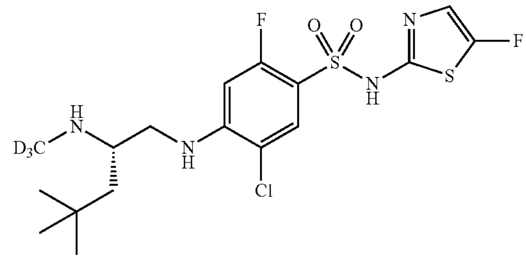 [SMILES: [2H]C([2H])([2H])N[C@H](CNc1cc(F)c(S(=O)(=O)Nc2ncc(F)s2)cc1Cl)CC(C)(C)C] | (S)-5-chloro-4-((4,4-dimethyl-2-((methyl-d3)amino)pentyl)amino)-2-fluoro-N-(5-fluorothiazol-2-yl)-benzenesulfonamide | LRMS m/z (M + H) 456.1 found, 456.1 required. |

Example 4 (S)-5-cyano-4-((4,4-dimethyl-2-(methylamino)pentyl)amino)-2-fluoro-N-(5-fluorothiazol-2-yl)benzenesulfonamide (4-3)

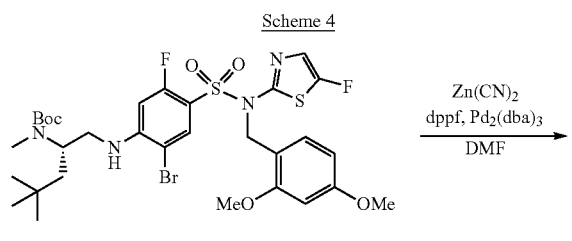

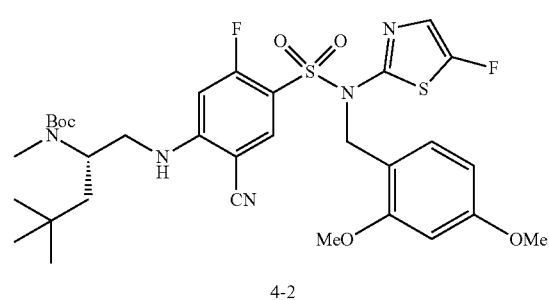

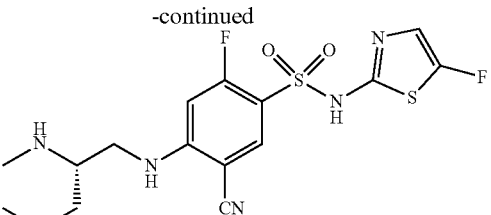

Preparation of tert-butyl (S)-(1-((2-cyano-4-(N-(2,4-dimethoxybenzyl)-N-(5-fluorothiazol-2-yl)sulfamoyl)-5-fluorophenyl)amino)-4,4-dimethylpentan-2-yl)(methyl)carbamate (4-2)

To a solution of 4-1 (prepared in analogous fashion to 2-10; 65 mg, 0.087 mmol) in DMF (8 mL) were added dicyanozinc (30.6 mg, 0.261 mmol), dppf (48.2 mg, 0.087 mmol) and Pd$_2$(dba)$_3$ (23.88 mg, 0.026 mmol). The mixture was stirred at 130° C. under N$_2$ for 2 h. The reaction progress was followed using TLC and LCMS, when LCMS and TLC showed the reaction was complete the mixture was diluted with EtOAc (20 mL) and washed with brine (20 mL), filtered and the filtrate was concentrated in vacuo. The crude product was purified by prep-TLC (SiO$_2$, PE:EA=2:1) to give 4-2 as yellow oil. LRMS m/z (M+H) 694.3 found, 694.3 required.

Preparation of (S)-5-cyano-4-((4,4-dimethyl-2-(methylamino)pentyl)amino)-2-fluoro-N-(5-fluorothiazol-2-yl)benzenesulfonamide (4-3)

A solution of 4-2 (35 mg, 0.050 mmol) in DCM/TFA (6 mL/5:1) was stirred at 20° C. for 1 h. Then the reaction was followed using LCMS. When the LCMS results showed the reaction was complete the mixture was concentrated to provide a residue. The residue was purified by HPLC (TFA) to give 4-3 as a white solid. LRMS m/z (M+H) 444.0 found, 444.1 required.

$^1$H NMR (CD$_3$OD, 400 MHz) δ 8.00 (d, J=7.6 Hz, 1H), 7.02 (s, 1H), 6.76 (d, J=12.8 Hz, 1H), 3.58-3.50 (m, 3H), 2.73 (s, 3H), 1.64-1.62 (m, 2H), 1.03 (s, 9H).

Example 5 (S)-5-chloro-2-fluoro-4-((3-(1-(fluoromethyl)cyclopropyl)-2-(methylamino)propyl)amino)-N-(5-fluorothiazol-2-yl)benzenesulfonamide (5-4)

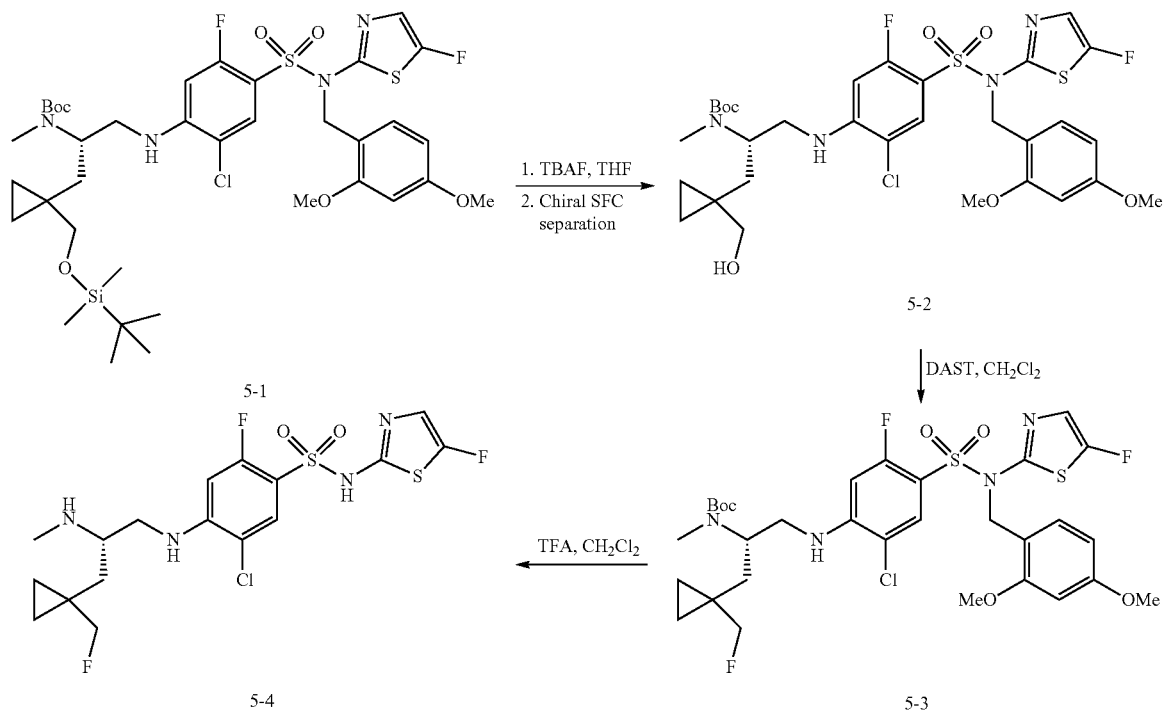

tert-butyl (S)-(1-((2-chloro-4-(N-(4-dimethoxbenzyl)-N-(5-fluorothiazol-2-yl)sulfamoyl)-5-fluorophenyl)amino)-3-(1-(hydroxymethyl)cyclopropyl)propan-2-yl)(methyl)carbamate (5-2)

A mixture of 5-1 (prepared from commercially available aldehyde and analogously to 2-10; 100 mg, 0.120 mmol) and TBAF (0.361 ml, 0.361 mmol) in THF (20 ml) was stirred for 1 h at 25° C. under $N_2$, at which time TLC analysis indicated the reaction was complete. The mixture was concentrated and purified by prep-TLC (EA:PE=1:3) to give 5-2 as yellow oil. LRMS m/z (M+H) 717.0 found, 717.0 required.

The product was separated by SFC: Column: Chiralcel OD-3 100×4.6 mm I.D.; 3 um Mobile phase: A: $CO_2$ B:methanol (0.05% DEA) Gradient: from 5% to 40% of B in 4.5 min and hold 40% for 2.5 min, then 5% of B for 1 min; Flow rate: 2.8 mL/min; Column temperature: 40° C. to give 5-2 (peak 1) (60 mg, 50%) as a yellow oil and 5-2 (peak 2) (60 mg, 50%) as a yellow oil.

Preparation of tert-butyl (S)-(1-((2-chloro-4-(N-(2,4-dimethoxybenzyl)-N-(5-fluorothiazol-2-yl)sulfamoyl)-5-fluorophenyl)amino)-3-(1-(fluoromethyl)cyclopropyl)propan-2-yl)(methyl)carbamate (5-3)

To a solution of 5-2 (peak 2) (80 mg, 0.112 mmol) in $CH_2Cl_2$ (10 ml) was added DAST (0.015 ml, 0.112 mmol) at 25° C. The reaction was stirred at 25° C. for 0.5 h under $N_2$, at which time TLC analysis indicated the reaction was complete. The mixture was quenched with MeOH (5 mL) and concentrated by vacuo to give the residue, which was purified by prep-TLC ($SiO_2$) (EtOAc:PE=1:1) to give 5-3 as a yellow oil. LRMS m/z (M+H) 719.2 found, 719.2 required.

Preparation of (S)-5-chloro-2-fluoro-4-((3-(1-(fluoromethyl)cyclopropyl)-2-(methylamino)propyl)amino)-N-(5-fluorothiazol-2-yl)benzenesulfonamide (5-4)

A mixture of 5-3 (50 mg, 0.070 mmol) and TFA (1 mL, 12.98 mmol) in $CH_2Cl_2$ (10 ml) was stirred for 0.5 h at 25° C. under $N_2$, at which time LCMS analysis indicated the reaction was complete. The reaction mixture was concentrated and purified by prep-HPLC (TFA) to give 5-4 as yellow solid. LRMS m/z (M+H) 469.1 found, 469.1 required.

$^1$H NMR (CD$_3$OD, 400 MHz) δ 7.73 (d, J=7.2 Hz, 1H), 6.98 (s, 1H), 6.66 (d, J=12.4 Hz, 1H), 3.59-3.56 (m, 3H), 2.74-2.72 (m, 1H), 2.45-2.39 (m, 2H), 2.37-2.23 (m, 4H), 2.17-1.91 (m, 1H), 1.61-1.59 (m, 3H). LRMS m/z (M+H) 469.1 found, 469.1 required.

Example 6 (S)-5-chloro-2-fluoro-N-(5-fluorothiazol-2-yl)-4-((2-(methylamino)-3-(1-methylcyclopropyl)propyl)amino)benzenesulfonamide (6-10)

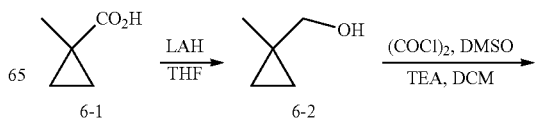

-continued
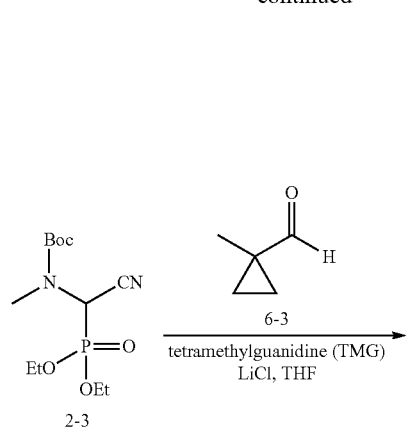
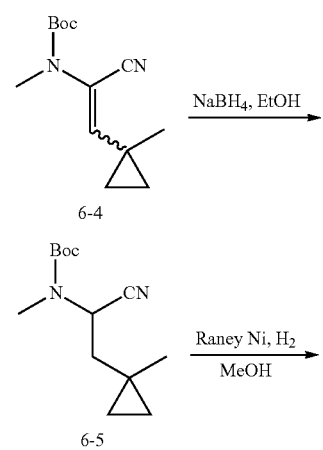
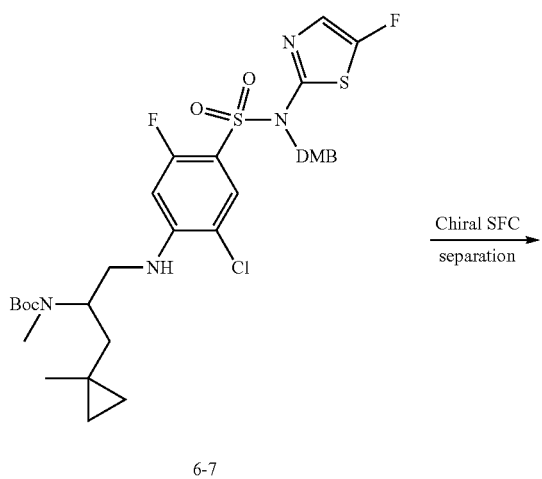
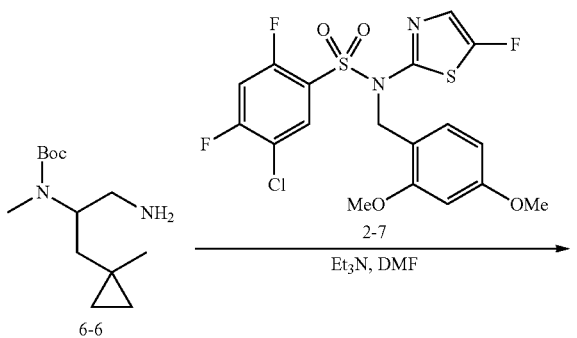
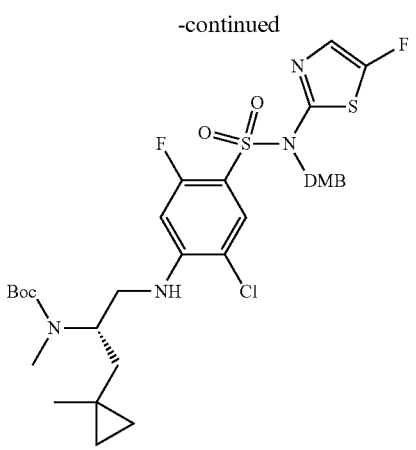
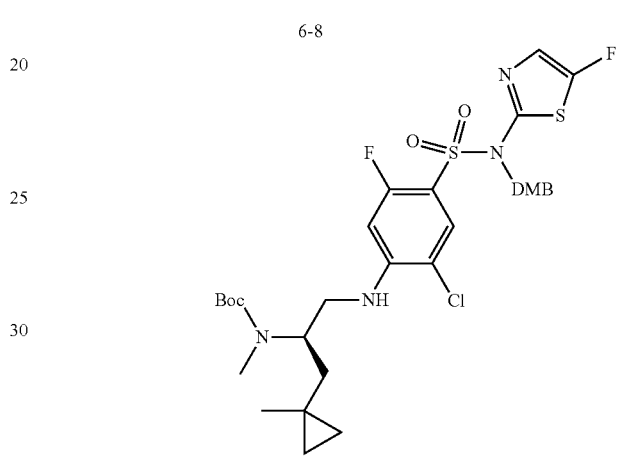
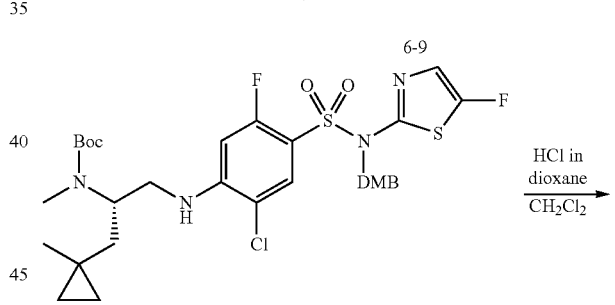
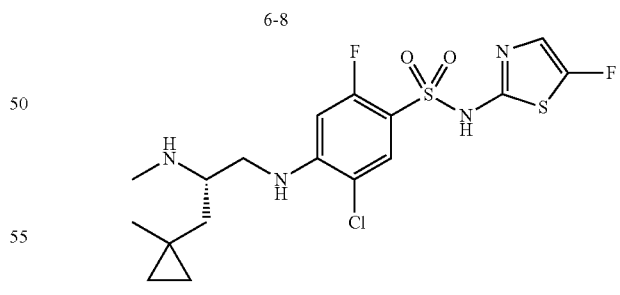
Preparation of (1-methylcyclopropyl)methanol (6-2)
To a mixture of LiAlH₄ (5.69 g, 150 mmol) in THF (50 mL) was added 6-1 (10 g, 100 mmol) in THF (100 mL) dropwise at 0° C. under N₂. The reaction mixture was stirred at 20° C. for 18 h. The reaction progress was followed using TLC. When TLC indicated the reaction was complete the reaction was quenched with H₂O (5.6 mL), followed by 15% NaOH (5.6 mL) then H₂O (16.8 mL), dried over MgSO₄, filtered and the filtrate was concentrated in vacuo to give the crude product 6-2 as a yellow oil, which was used in next step without further purification.

¹H NMR (CDCl₃, 400 MHz) δ 3.38 (s, 2H), 1.15 (s, 3H), 0.39 (s, 2H), 0.34-0.29 (m, 2H).

Preparation of 1-methylcyclopropane-1-carbaldehyde (6-3)

To a stirred solution of oxalyl dichloride (29.5 g, 232 mmol) in DCM (40 mL) was added DMSO (43.7 g, 464 mmol) at −78° C., which was allowed to stir for 0.5 h at the same temperature. 6-2 (10 g, 116 mmol) in DCM (100 mL) was added at −78° C., which was allowed to stir for 0.5 h at the same temperature. At the end of this time, TEA (94 g, 929 mmol) was added at −78° C., which was allowed to stir for 0.5 h at the same temperature. The reaction was allowed to stir for an additional 0.5 h at 0° C. and the reaction progress was followed by TLC. When TLC indicated that the starting material was consumed completely the reaction was diluted with H₂O (200 mL) and extracted with 2 aliquots of DCM (100 mL each). The organic layer was washed with aqueous 1M HCl (200 mL each), brine (200 mL) and dried over Na₂SO₄, filtered, then concentrated to give 6-3 as a yellow oil which was used in the next step directly.

¹HNMR (CDCl₃, 400 MHz) δ 8.62 (s, 1H), 1.23 (s, 3H), 1.18-1.12 (m, 2H), 0.93-0.88 (m, 2H).

Preparation of tert-butyl (1-cyano-2-(1-methylcyclopropyl)vinyl)(methyl)carbamate (6-4)

To a mixture of 2-3 (15 g, 49.0 mmol) and TMG (11.28 g, 98 mmol) in THF (200 mL) at −78° C. under N₂ was added 6-3 (10 g, 83 mmol) in THF (100 mL) dropwise. And then the mixture was stirred at 20° C. for 0.5 h. To the mixture was added LiCl (2.076 g, 49.0 mmol) and stirred at 20° C. for 20 h. The reaction progress was followed by TLC. When the TLC results indicated that the starting material had been consumed the mixture was quenched with saturated NH₄Cl aq. (300 mL), and extracted with 2 aliquots of EtOAc (200 mL each). The organic layer was washed with brine (400 mL), dried over Na₂SO₄, filtered and concentrated. The residue was purified by column chromatography on silic gel (PE:EtOAc=30:1) to give 6-4 as a colorless oil.

¹H NMR (CDCl₃, 400 MHz) δ 5.94 (s, 1H), 3.02 (s, 3H), 1.47 (s, 9H), 1.40 (s, 3H), 0.87-0.78 (m, 4H).

Preparation of tert-butyl (1-cyano-2-(1-methylcyclopropyl)ethyl)(methyl)carbamate (6-5)

To a mixture of 6-4 (1 g, 4.23 mmol) in MeOH (20 mL) was added NaBH₄ (0.800 g, 21.16 mmol) slowly at 0° C. The reaction was stirred at 20° C. for 2 h. The reaction was monitored by TLC until it indicated the starting material had been consumed. The mixture was diluted with H₂O (20 mL), and extracted with 2 aliquots of EtOAc (20 mL each). The organic layer was washed with H₂O (50 mL), brine (50 mL) and dried over Na₂SO₄, then filtered and concentrated to give a residue which was purified by column chromatography (SiO₂) (PE:EtOAc=20:1) to give 6-5 as a colorless oil.

¹H NMR (CDCl₃, 400 MHz) δ 5.42-5.16 (m, 1H), 2.92-2.81 (m, 3H), 1.78-1.66 (m, 2H), 1.48 (s, 9H), 1.12 (s, 3H), 0.50-0.44 (m, 1H), 0.43-0.37 (m, 1H), 0.37-0.27 (m, 2H).

Preparation of tert-butyl (1-amino-3-(1-methylcyclopropyl)propan-2-yl)(methyl)carbamate (6-6)

To a solution of 6-5 (530 mg, 2.224 mmol) in EtOH (20 mL) was added Raney Ni (200 mg, 2.224 mmol) and NH₃.H₂O (0.3 mL, 2.224 mmol). The reaction mixture was stirred at 20° C. for 40 min under H₂ (15 Psi). Reaction progress was followed using LCMS. When LCMS indicated the starting material had been consumed the reaction mixture was filtered to remove solids and the filtrate was concentrated under reduced pressure to afford 6-6 as a yellow oil, used in the next step directly. LRMS (M+H) m/z 243.3 found, 243.3 required.

Preparation of tert-butyl (S)-(1-((2-chloro-4-(N-(2,4-dimethoxybenzyl)-N-(5-fluorothiazol-2-yl)sulfamoyl)-5-fluorophenyl)amino)-3-(1-methylcyclopropyl)propan-2-yl)(methyl)carbamate (6-8) and tert-butyl (R)-(1-((2-chloro-4-(N-(2,4-dimethoxybenzyl)-N-(5-fluorothiazol-2-yl)sulfamoyl)-5-fluorophenyl)amino)-3-(1-methylcyclopropyl)propan-2-yl)(methyl)carbamate (6-9)

A mixture of 6-6 (3.3 g, 13.62 mmol), 5-chloro-N-(2,4-dimethoxybenzyl)-2,4-difluoro-N-(5-fluorothiazol-2-yl)benzenesulfonamide (6.52 g, 13.62 mmol) and TEA (6.89 g, 68.1 mmol) in DMF (100 mL) was stirred at 40° C. for 16 h, and the reaction was monitored by TLC. When TLC indicated the starting material had been consumed the mixture was concentrated and purified by column chromatography (SiO₂, PE:EtOAc=7: 1-5:1) to give 6-7 as a colorless oil.

The product 6-7 (8 g, 11.41 mmol) was separated by SFC (From 1000223-100-1_E1: Column: Chiralpak AD-3 150× 4.6 mm I.D., 3 um Mobile phase: A: CO₂ B:iso-propanol (0.05% DEA) Gradient: from 5% to 40% of B in 5 min and hold 40% for 2.5 min, then 5% of B for 2.5 min Flow rate: 2.5 mL/min Column temp.: 35° C.) to give 6-8 (Rt=4.378) as white solid and 6-9 (Rt=4.905, 3.7 g) as white solid.

¹H NMR (CDCl₃, 400 MHz) δ 7.41 (dd, J 13.3, 6.7 Hz, 1H), 6.91 (d, J 8.2 Hz, 1H), 6.69 (d, J 2.3 Hz, 1H), 6.15-5.94 (m, 3H), 4.76 (s, 2H), 4.42-4.24 (m, 1H), 3.65-3.30 (m, 6H), 2.99-2.79 (m, 2H), 1.40 (dd, J 14.1, 8.2 Hz, 1H), 1.29-1.05 (m, 9H), 1.05-0.96 (m, 1H), 0.88-0.60 (m, 3H), 0.20-0.09 (m, 4H).

Preparation of (S)-5-chloro-2-fluoro-N-(5-fluorothiazol-2-yl)-4-((2-(methylamino)-3-(1-methylcyclopropyl)propyl)amino)benzenesulfonamide (6-10)

A mixture of 6-8 (3.8 g, 5.42 mmol) and HCl (40 mL, 160 mmol) (4M in 1,4-dioxane) in DCM (60 mL) was stirred at 20° C. for 1 h. Reaction progress was monitored using LCMS. When LCMS indicated the starting material had been consumed the reaction mixture was filtered and purified by acidic prep-HPLC (HCl) to give 6-10 as a white solid.

Prep-HPLC condition: Preparative HPLC on a Phenomenex Synergi C18 250*80 mm*10 um using water and acetonitrile as the eluents. Mobile phase A: 0.05% HCl water. Mobile phase B: acetonitrile. Gradient: 0-10% B, 0-16.0 min; 100% B, 16.1-21.0 min; 40% B, 21.1-23.0 min. FlowRate: 120 mL/min.

¹H NMR (CD₃OD, 400 MHz) δ 7.75 (d, J=7.1 Hz, 1H), 7.00 (s, 1H), 6.69 (d, J=12.3 Hz, 1H), 3.68 (d, J=11.9 Hz, 2H), 3.54 (d, J=13.0 Hz, 1H), 2.74 (s, 3H), 1.97 (dd, J=4.1, 14.2 Hz, 1H), 1.45 (dd, J=14.0, 8.7 Hz, 1H), 1.15 (s, 3H), 0.45 (d, J=6.4 Hz, 4H). LRMS m/z (M+H) 451.0 found, 451.0 required.

Example 7 Preparation of (R)-5-chloro-4-((2-(dimethylamino)-3-(trimethylsilyl)propyl)-amino)-2-fluoro-N-(5-fluorothiazol-2-yl)benzenesulfonamide (7-2)

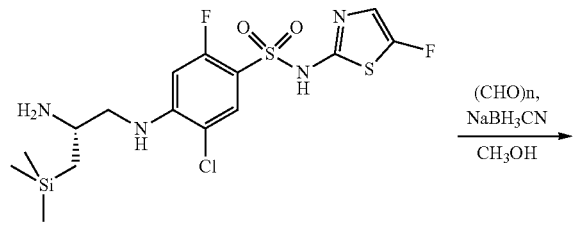

7-1

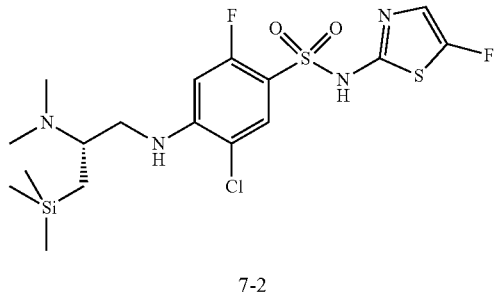

7-2

To a solution of 7-1 (20 mg, 0.044 mmol; prepared via methods in Example 2) in MeOH (10 mL) was added (CHO)$_n$ (6.38 mg, 0.220 mmol)) and NaCNBH$_3$ (5.52 mg, 0.088 mmol)). The resulting mixture was stirred at 25° C. for 16 h. Then the reaction was monitored by LCMS until no starting material was detected. The mixture was concentrated in vacuo and the residue was purified by prep-HPLC (TFA) to give crude 7-2. The crude mixture was purified using preparative HPLC under the following conditions: (i) Phenomenex Synergi C18 column (150 A pore size, 4 micon particle size×30 mm Length); (ii) 25 ml/min; (iii) eluted with 0.05% TFA/water (mobile phase A) and acetonitrile (mobile phase B) using the following eluent program: (a) gradient in B (A+54% to 74% B) 0-10 minutes; (b) 100% B, 10.1 to 12.0 min.; (c) A+10% B fixed, 12.1 to 15.0 minutes.

$^1$H NMR (CD$_3$OD, 400 MHz) δ7.57 (d, J=6.7 Hz, 1H), 6.81 (s, 1H), 6.50 (d, J=12.5 Hz, 1H), 3.69-3.57 (m, 1H), 3.42 (dd, J=15.1, 10.4 Hz, 1H), 3.19 (dd, J=15.1, 3.5 Hz, 1H), 2.62 (s, 6H), 0.97 (d, J=13.9 Hz, 1H), 0.72 (t, J=13.2 Hz, 1H), 0.00 (s, 9H). LRMS m/z (M+H) 483.1 found, 483.1 required.

TABLE 4

| Exp No | Structure | Name | Data |
|---|---|---|---|
| Ex 7-3 | 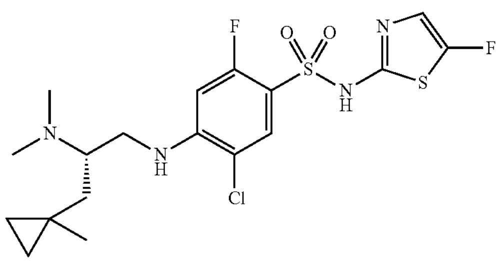 | (S)-5-chloro-4-((2-(dimethylamino)-3-(1-methylcyclopropyl)propyl)amino)-2-fluoro-N-(5-fluorothiazol-2-yl)benzenesulfonamide | LRMS m/z (M + H) 437.1 found, 437.1 required. |
| Ex 7-4 | 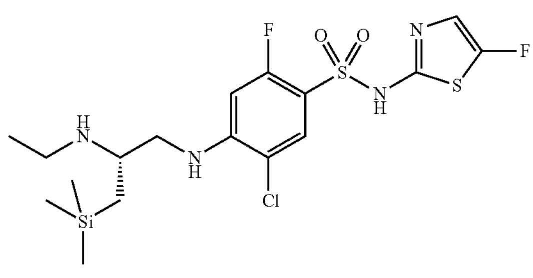 [SMILES: CCN[C@H](CNc1cc(F)c(S(=O)(=O)Nc2ncc(F)s2)cc1Cl)C[Si](C)(C)C] | (R)-5-chloro-4-((2-(ethylamino)-3-(trimethylsilyl)propyl)amino)-2-fluoro-N-(5-fluorothiazol-2-yl)benzenesulfonamide | LRMS m/z (M + H) 483.1 found, 483.1 required |
| Ex 7-5 | 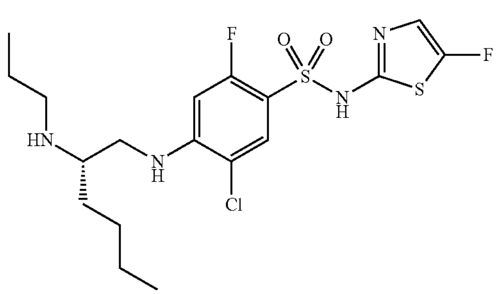 [SMILES: CCCC[C@@H](CNc1cc(F)c(S(=O)(=O)Nc2ncc(F)s2)cc1Cl)NCCC] | (S)-5-chloro-2-fluoro-N-(5-fluorothiazol-2-yl)-4-((2-(propylainino)hexyl)amino)benzenesulfonamide | LCMS m/z (M) 467.1 found, 467.1 required. |

TABLE 4-continued

| Exp No | Structure | Name | Data |
| --- | --- | --- | --- |
| Ex 7-6 | 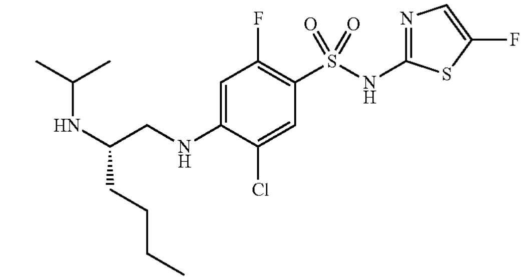 [SMILES: CCCC[C@@H](CNc1cc(F)c(S(=O)(=O)Nc2ncc(F)s2)cc1Cl)NC(C)C] | (S)-5-chloro-2-fluoro-N-(5-fluorothiazol-2-yl)-4-((2-(isopropylamino)hexyl)amino)benzenesulfonamide | LCMS m/z (M) 467.1 found, 467.1 required. |

Core Synthesis Examples (CSE-Number)

Preparation of 5-chloro-N-(2,4-dimethoxybenzyl)-2,4-difluoro-N-(thiazol-2-yl)benzene sulfonamide (CSE 1-5)

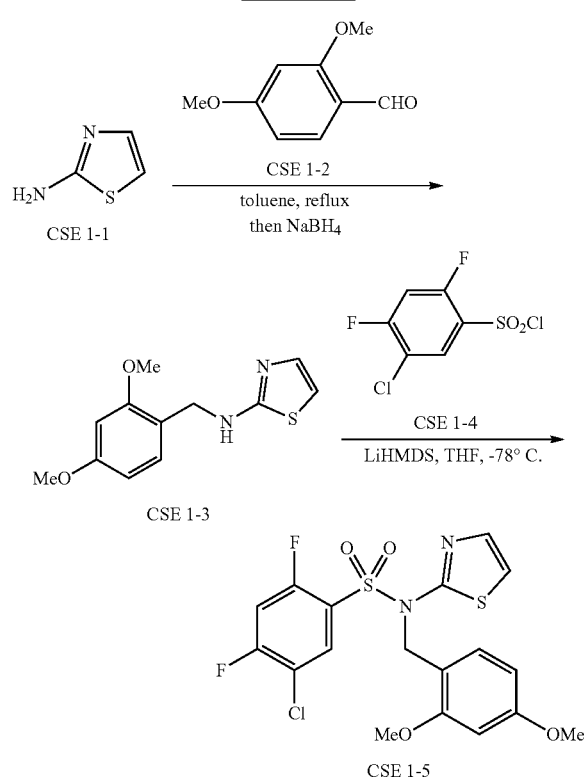

Scheme CSE-1

Preparation of N-(2,4-dimethoxybenzyl)thiazol-2-amine (CSE 1-3)

A mixture of CSE 1-1 (100 g, 1 mol) and CSE 1-2 (151 g, 0.91 mol) in 2 L of toluene was refluxed for 8 h with Dean-Stark apparatus to remove water. The mixture was cooled and the solvent was evaporated in vacuo. To the residue was added 3 L of MeOH and the resulting mixture was cooled to 0° C. NaBH$_4$ (151 g, 4 mol) was added carefully in portions. The mixture was then warmed to room temperature and stirred for 4 h. The mixture was quenched with water, then MeOH was evaporated in vacuo. The water layer was extracted with EtOAc and the combined organic layers were dried over Na$_2$SO$_4$, filtered and concentrated. The residue was purified by column chromatography on silica gel (PE:EtOAc=5:1 to 2:1) to give the product of CSE 1-3. $^1$H NMR (400 MHz CD$_3$OD) δ 7.16 (d, J=8.4 Hz, 1H), 6.97 (d, J=4.0 Hz, 1H), 6.50-6.52 (m, 2H), 6.44 (dd, J=8.0, 2.0 Hz, 1H), 4.35 (s, 2H), 3.81 (s, 3H), 3.76 (s, 3H).

Preparation of 5-chloro-N-(2,4-dimethoxybenzyl)-2,4-difluoro-N-(thiazol-2-yl)benzene sulfonamide (CSE 1-5)

Under an atmosphere of nitrogen, CSE 1-3 (5 g, 20 mmol) was dissolved in THF (100 mL) and cooled to −78° C. LiHMDS (24 mL, 24 mmol) was added dropwise keeping the temperature below −60° C. After 30 minutes, the cooling bath was removed and the reaction was warmed to room temperature for a further 30 minutes then cooled back to −78° C. A solution of CSE 1-4 (5.54 g, 22.4 mmol) in THF (10 mL) was added dropwise keeping the temperature below −60° C. and the reaction mixture was warmed to room temperature. Saturated aqueous ammonium chloride solution (50 mL) was added followed by water to dissolve the solid which had precipitated out. The aqueous layer was extracted with ethyl acetate (50 mL) and the organic extracts was dried over Na$_2$SO$_4$, filtered and concentrated. The residue was purified by column chromatography on silica gel (PE:EtOAc=10:1) to give the product of CSE 1-5. $^1$H NMR (400 MHz CDCl$_3$) δ 7.88-7.92 (m, 1H), 7.40 (d, J=4.0, 1H), 7.16-7.18 (m, 1H), 6.96-7.01 (m, 2H), 6.32-6.36 (m, 2H), 5.16 (s, 2H), 3.74 (s, 3H), 3.71 (s, 3H); MS (M+H)$^+$: 461.

The following cores were made using synthesis analogous to that shown above for CSE 1-5:

5-chloro-N-(2,4-dimethoxybenzyl)-2,4-difluoro-N-(5-fluorothiazol-2-yl)benzenesulfonamide (CSE 2)

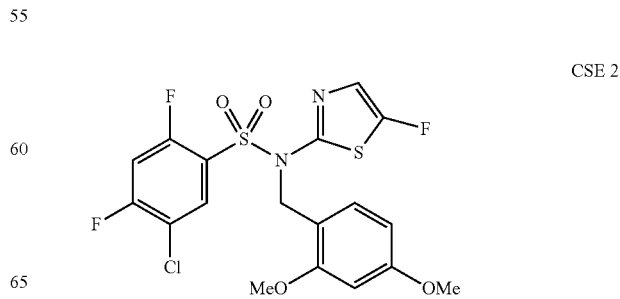

CSE 2

$^1$H NMR (400 MHz, CDCl$_3$) δ 7.87 (t, J=7.6 Hz, 1H), 7.16 (d, J=8.4 Hz, 1H), 7.01-7.06 (m, 2H), 6.38 (dd, J=8.4, 2.4 Hz, 1H), 6.33 (d, J=2.4 Hz, 1H), 5.04 (s, 2H), 3.77 (s, 3H), 3.72 (s, 3H). MS m/z (M+H): 479.

5-chloro-N-(2,4-dimethoxybenzyl)-2,4-difluoro-N-(1,2,4-thiadiazol-5-yl) benzenesulfonamide (CSE 3)

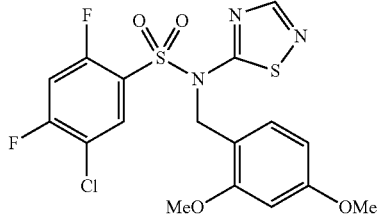

CSE 3

$^1$H NMR (400 MHz, CDCl3) δ 8.22 (s, 1H), 7.73 (t, J=7.6 Hz, 1H), 7.19 (d, J=8.4 Hz, 1H), 6.87 (t, J=8.4 Hz, 1H), 6.35 (dd, J=2.4, 6.0 Hz, 1H), 6.15 (d, J=2.0 Hz, 1H), 5.36 (s, 2H), 3.74 (s, 3H), 3.66 (s, 3H). MS m/z (M+H): 462.0

Biological Data

The various compounds shown in Examples 1 through 5 and the accompanying Tables in the above examples were assayed for activity and selectivity using the IonWorks® technique and procedure described herein. The results are reported in the following paragraph in a format expressing the identification of the compound with reference Example and compound (e.g. Ex 1-7 is Example 1, compound 7) followed by the observed potency in nM and the ratio of Na$_v$1.7 potency:Na$_v$ 1.5 potency as described here. Thus, Ex1-7: 1.7=200/ratio>165 identifies compound Ex 1-7 as having 200 nM potency for the Na$_v$ 1.7 sodium ion channel (as measured by IonWorks®) and a ratio of greater than 165 Na$_v$ 1.7:Na$_v$ 1.5 potency, determined by IonWorks® measurement. The following results are reported:

IonWorks® Data

Ex1-7: 1.7=200/ratio>165; Ex1-12: 1.7=61/ratio>541; Ex1-18: 1.7=15/ratio>2200; Ex1-19: 1.7=24/ratio>1375; Ex1-20: 1.7=280/ratio>118; Ex1-21: 1.7=200/ratio>165; Ex1-22: 1.7=140/ratio>236; Ex1-23: 1.7=36/ratio>917; Ex1-24: 1.7=440/ratio>75; Ex1-25: 1.7=110/ratio>300; Ex1-26: 1.7=200/ratio>165; Ex1-27: 1.7=190/ratio>174; Ex1-28: 1.7=32/ratio>1031; Ex1-29: 1.7=310/ratio>106; Ex1-30: 1.7=160/ratio>206; Ex1-31: 1.7=30/ratio>1100; Ex1-32: 1.7=170/ratio>194; Ex1-33: 1.7=130/ratio>254; Ex1-34: 1.7=33/ratio>1000; Ex2-12: 1.7=1030/ratio>32; Ex2-13: 1.7=54/ratio>611; Ex2-14: 1.7=170/ratio>194; Ex2-15: 1.7=670/ratio>49; Ex2-16: 1.7=120/ratio>275; Ex2-17: 1.7=14/ratio>1929; Ex2-18: 1.7=850/ratio>39; Ex2-19: 1.7=800/ratio>41; Ex2-20: 1.7=68/ratio>485; Ex2-21: 1.7=110/ratio>300; Ex2-22: 1.7=1000/ratio>23; Ex2-23: 1.7=12/ratio>2750; Ex3-11: 1.7=110/ratio>300; Ex3-13: 1.7=300/ratio>110; Ex3-14: 1.7=64/ratio>429; Ex4-3: 1.7=640/ratio>52; Ex5-4: 1.7=2000 ratio>14; Ex6-10: 1.7=340 ratio>68; Ex7-2: 1.7=18 ratio>889; Ex7-3: 1.7=150 ratio>220; Ex7-4: 1.7=3 ratio>11000; Ex7-5: 1.7=41 ratio>805; Ex7-6: 1.7=30 ratio>533.

IonWorks® Experimental Procedure

Compounds were tested on human Na$_v$1.7 and Na$_v$1.5 channels stably expressed in HEK 293 cells. Sodium current measurements on IonWorks Quattro: An automated patch-clamp assay on the IonWorks Quattro platform (Molecular Devices) was used to measure state-dependent inhibition of human Na$_v$1.7 and 1.5 channels. Cells were sealed on a planar substrate using the Population Patch Plate (PPC) technology. Electrical access was obtained using both nystatin and amphotericin. A double-pulse protocol was used for the determination of IC$_{50}$ values for inactivated state block. Na$_v$1.7 and Na$_v$1.5 expressing cells were voltage clamped at −100 mV and −110 mV, respectively. A depolarizing prepulse to −10 mV (Na$_v$1.7) or −30 mV (Na$_v$1.5) for 1000 ms followed by a 10 ms repolarization to −100 mV (Na$_v$1.7) or −110 mV (Na$_v$1.5) was given to generate fractional channel inactivation of ~50%, followed by a 10 ms test pulse to −10 mV (Na$_v$1.7) or −30 mV (Na$_v$1.5) to measure peak current in control conditions and after compound addition. The following recording solutions were used (mM). External: 150 NaCl, 2 CaCl$_2$, 5 KCl, 1 Mg Cl$_2$, 10 HEPES, 12 Dextrose; internal: 120 CsF, 30 CsCl, 10 EGTA, 5 HEPES, 5 NaF, 2 MgCl$_2$.

For all electrophysiology experiments, offline analysis was used to determine percent inhibition as a function of drug concentration. IC$_{50}$ values were determined by fitting to the Hill equation.

What is claimed is:

1. A compound of Formula A, or a pharmaceutically acceptable salt thereof:

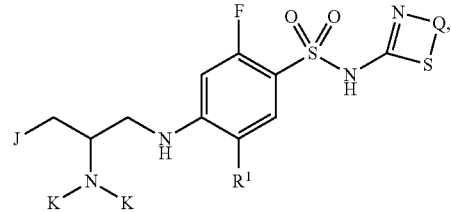

Formula A wherein:

R$^1$ is —CN; —Cl, —Br, or —F;

Q is: (i) —(CH═CR$^2$)—, where R$^2$ is H, or —F; or (ii) —(C═N)—

K is independently for each occurrance —H or a linear, branched, or cycloalkyl moiety comprising up to 6 carbon atoms; and J is:
  (a) linear, or branched alkyl of up to 6 carbon atoms which is optionally substituted with: (i) a cycloalkyl of up to 6 carbon atoms; or (ii) aryl which is optionally substituted with one or more halogen or a linear, branched, or cycloalkyl moiety comprising up to 6 carbon atoms;
  (b) trimethylsilyl;
  (c) cycloalkyl of up to 6 carbon atoms which is optionally substituted on one or more carbon atoms thereof with, independently for each occurrence: (i) a linear, branched, or cycloalkyl moiety comprising up to 6 carbon atoms which is optionally substituted with a halogen; or (ii) halogen;

(d) a bridged bicyclo alkyl of the formula:

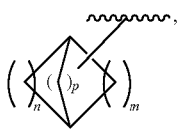

where n, m and p are independently 1 to 3 and the sum of n+m+p is 6 or less, and wherein any of the ring carbon atoms may optionally be substituted with a linear, branched, or cycloalkyl moiety comprising up to 6 carbon atoms; or (e) aryl of the formula:

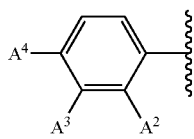

wherein, independently:
$A^2$ is —H, —Br, or —F;
$A^3$ is —H, —Cl, —Br, or —F;
$A^4$ is —H, —Cl, —CH$_3$, —Br, or —F.

2. A compound of claim 1, or a pharmaceutically acceptable salt thereof, wherein one K is selected to be a linear, branched, or cycloalkyl comprising up to 6 carbon atoms, which alkyl is partially or fully deuterated.

3. A compound of claim 1, or a pharmaceutically acceptable salt thereof, with the structure of Formula A-2:

Formula A-2

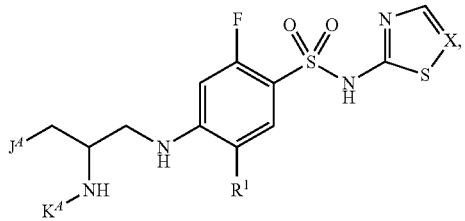

wherein:
X is N or C—$R^{2A}$, wherein $R^{2A}$ is —F or —H;
$K^A$ is —CH$_3$ or —CD$_3$; and
$J^A$ is a linear, branched or cyclic alkyl of up to 4 carbon atoms which is optionally substituted on one carbon thereof with a linear, branched, or cycloalkyl moiety comprising up to 6 carbon atoms.

4. A compound of claim 3, or a pharmaceutically acceptable salt thereof, wherein $J^A$ is a branched alkyl of up to 5 carbon atoms or a cyclic alkyl of up to 5 carbon atoms which is substituted on a ring carbon thereof with a linear, branched, or cycloalkyl moiety comprising up to 6 carbon atoms.

5. A compound of claim 1, or a pharmaceutically acceptable salt thereof, wherein Q is —(C=CF)—.

6. A compound of claim 1, or a pharmaceutically acceptable salt thereof, wherein wherein Q is —(C=CH)—.

7. A compound of claim 1, or a pharmaceutically acceptable salt thereof, wherein wherein Q is —(C=N)—.

8. A compound of claim 1, or a pharmaceutically acceptable salt thereof, wherein $R^1$ is Cl.

9. A compound which is:
(S)-5-chloro-2-fluoro-4-((2-(methylamino)-3-phenylpropyl)amino)-N-(thiazol-2-yl)benzenesulfonamide;
(S)-5-chloro-2-fluoro-4-((2-(methylamino)-3-phenylpropyl)amino)-N-(1,2,4-thiadiazol-5-yl)-benzenesulfonamide;
(S)-5-chloro-2-fluoro-N-(5-fluorothiazol-2-yl)-4-((2-(methylamino)-3-phenylpropyl)amino)-benzenesulfonamide;
(S)-5-chloro-2-fluoro-4-((3-(4-fluorophenyl)-2-(methylamino)propyl)amino)-N-(thiazol-2-yl)benzenesulfonamide;
(S)-5-chloro-4-((3-cyclohexyl-2-(methylamino)propyl)amino)-2-fluoro-N-(thiazol-2-yl)benzenesulfonamide;
(S)-5-chloro-2-fluoro-4-((2-(methylamino)-3-(p tolyl)propyl)amino)-N-(thiazol-2-yl)-benzenesulfonamide;
(S)-5-chloro-2-fluoro-4-((2-(methylamino)-4-phenylbutyl)amino)-N-(thiazol-2-yl)-benzenesulfonamide;
(S)-5-chloro-2-fluoro-N-(5-fluorothiazol-2-yl)-4-((2-(methylamino)-4-phenylbutyl)amino)-benzenesulfonamide;
(S)-4-((3-(3-bromo-phenyl)-2-(methylamino)-propyl)amino)-5-chloro-2-fluoro-N-(thiazol-2-yl)-benzenesulfonamide;
(S)-4-((3-(2-bromo-phenyl)-2-(methylamino)-propyl)amino)-5-chloro-2-fluoro-N-(thiazol-2-yl)-benzenesulfonamide;
(S)-4-((3-(4-bromo-phenyl)-2-(methylamino)-propyl)amino)-5-chloro-2-fluoro-N-(thiazol-2-yl)-benzenesulfonamide;
(S)-5-chloro-2-fluoro-4-((3-(3-fluorophenyl)-2-(methylamino)-propyl)-amino)-N-(thiazol-2-yl)-benzenesulfonamide;
(S)-5-chloro-2-fluoro-4-((3-(2-fluorophenyl)-2-(methylamino)-propyl)-amino)-N-(thiazol-2-yl)-benzenesulfonamide;
(S)-5-chloro-4-((3-(3,5-difluorophenyl)-2-(methylamino)-propyl)amino)-2-fluoro-N-(thiazol-2-yl)-benzenesulfonamide;
(S)-5-chloro-4-((3-(3,4-difluorophenyl)-2-(methylamino)propyl)amino)-2-fluoro-N-(thiazol-2-yl)-benzenesulfonamide;
(S)-4-((3-(2-bromo-4-fluorophenyl)-2-(methyl-amino)propyl)-amino)-5-chloro-2-fluoro-N-(thiazol-2-yl)-benzenesulfonamide;
(S)-4-((3-(2-bromo-3-fluorophenyl)-2-(methyl-amino)propyl)-amino)-5-chloro-2-fluoro-N-(thiazol-2-yl)-benzenesulfonamide;
(S)-5-chloro-4-((3-(4-chlorophenyl)-2-(methyl-amino)propyl)amino)-2-fluoro-N-(thiazol-2-yl)-benzenesulfonamide;
(S)-5-chloro-4-((4,4-dimethyl-2-(methylamino)pentyl)amino)-2-fluoro-N-(5-fluorothiazol-2-yl)benzenesulfonamide;
(S)-5-chloro-4-((3-cyclobutyl-2-(methylamino)propyl)amino)-2-fluoro-N-(5-fluorothiazol-2-yl)benzenesulfonamide;
(S)-4-((3-(bicyclo[1.1.1]pentan-1-yl)-2-(methylamino)propyl)-amino)-5-chloro-2-fluoro-N-(5-fluorothiazol-2-yl)-benzenesulfonamide;
(S)-5-chloro-2-fluoro-N-(5-fluorothiazol-2-yl)-4-((2-(methylamino)-3-(1-(trifluoromethyl)cyclopropyl)-propyl)amino)benzenesulfonamide;

(S)-5-chloro-4-((5,5-dimethyl-2-(methylamino)hexyl)amino)-2-fluoro-N-(5-fluorothiazol-2-yl)-benzenesulfonamide;
(S)-5-chloro-2-fluoro-4-((2-(methylamino)-3-(1-(trifluoromethyl)cyclopropyl)-propyl)amino)-N-(thiazol-2-yl)-benzenesulfonamide;
(R)-5-chloro-2-fluoro-N-(5-fluorothiazol-2-yl)-4-((2-(methylamino)-3-(trimethylsilyl)propyl)-amino)benzenesulfonamide;
(S)-5-chloro-4-((3-cyclopropyl-2-(methylamino)propyl)amino)-2-fluoro-N-(5-fluorothiazol-2-yl)-benzenesulfonamide;
(S)-5-chloro-4-((4-cyclopropyl-2-(methylamino)butyl)amino)-2-fluoro-N-(5-fluorothiazol-2-yl)-benzenesulfonamide;
5-chloro-4-(((2S)-3-(2,2-dimethylcyclopropyl)-2-(methylamino)propyl)amino)-2-fluoro-N-(5-fluorothiazol-2-yl)-benzenesulfonamide;
5-chloro-4-(((2S)-3-(2,2-dichlorocyclopropyl)-2-(methylamino)propyl)amino)-2-fluoro-N-(5-fluorothiazol-2-yl)-benzenesulfonamide;
5-chloro-4-(((2S)-3-(2,2-difluorocyclopropyl)-2-(methylamino)propyl)amino)-2-fluoro-N-(5-fluorothiazol-2-yl)-benzenesulfonamide;
(S)-5-chloro-4-((3-cyclopentyl-2-(methylamino)propyl)amino)-2-fluoro-N-(5-fluorothiazol-2-yl)benzenesulfonamide;
(R)-5-chloro-4-((3-cyclopentyl-2-(methylamino)propyl)amino)-2-fluoro-N-(5-fluorothiazol-2-yl)benzenesulfonamide;
(S)-5-chloro-4-((4-cyclobutyl-2-(methylamino)butyl)amino)-2-fluoro-N-(5-fluorothiazol-2-yl)-benzenesulfonamide;
(S)-5-chloro-4-((4,4-dimethyl-2-((methyl-d3)amino)pentyl)amino)-2-fluoro-N-(5-fluorothiazol-2-yl)-benzenesulfonamide;
(S)-5-chloro-2-fluoro-4-((3-(1-(fluoromethyl)cyclopropyl)-2-(methylamino)propyl)amino)-N-(5-fluorothiazol-2-yl)benzenesulfonamide;
(S)-5-chloro-2-fluoro-N-(5-fluorothiazol-2-yl)-4-((2-(methylamino)-3-(1-methylcyclopropyl)propyl)amino)benzenesulfonamide;
S)-5-chloro-2-fluoro-N-(5-fluorothiazol-2-yl)-4-((2-(methylamino)-4-(1-methylcyclopropyl)butyl)amino)benzenesulfonamide;
(S)-5-chloro-2-fluoro-N-(5-fluorothiazol-2-yl)-4-((2-(methylamino)-4-(1-methylcyclopropyl)butyl)amino)benzenesulfonamide;
(S)-5-chloro-4-((2-(dimethylamino)-3-(1-methylcyclopropyl)propyl)amino)-2-fluoro-N-(5-fluorothiazol-2-yl)benzenesulfonamide;
(R)-5-chloro-4-((2-(ethylamino)-3-(trimethylsilyl)propyl)amino)-2-fluoro-N-(5-fluorothiazol-2-yl)benzenesulfonamide;
(S)-5-chloro-2-fluoro-N-(5-fluorothiazol-2-yl)-4-((2-(propylamino)hexyl)amino) benzenesulfonamide;
(S)-5-chloro-2-fluoro-N-(5-fluorothiazol-2-yl)-4-((2-(isopropylamino)hexyl)amino)-benzenesulfonamide; or
(S)-5-cyano-4-((4,4-dimethyl-2-(methylamino)pentyl)amino)-2-fluoro-N-(5-fluorothiazol-2-yl)benzenesulfonamide, or a pharmaceutically acceptable salt of any thereof.

10. A composition comprising at least one compound of claim 1, or a pharmaceutically acceptable salt thereof, and at least one pharmaceutically acceptable excipient.

11. A composition of claim 10 comprising additionally at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP), and a pharmaceutically acceptable carrier.

12. A method of treating (a) a pain disorder; (b) a cough; or (c), an itch disorder selected from: i) acute itch; or (ii) chronic itch, the method comprising administering to a patient in need thereof a therapeutically effective amount of a composition of claim 10.

13. A method of treating (a) a pain disorder; (b) a cough; or (c), an itch disorder selected from: i) acute itch; or (ii) chronic itch, the method comprising administering to a patient in need thereof a therapeutically effective amount of a composition of claim 11.

14. The method of claim 12 wherein said disorder is chronic pain.

15. The method of claim 13 wherein said disorder is chronic pain.

16. A composition comprising at least one compound of claim 9, or a pharmaceutically acceptable salt thereof, and at least one pharmaceutically acceptable excipient.

17. A composition of claim 16 comprising additionally at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP), and a pharmaceutically acceptable carrier.

18. A method of treating acute pain, comprising administering to a patient in need thereof a therapeutically effective amount of a composition of claim 16.

* * * * *